(12) United States Patent
Kokeguchi et al.

(10) Patent No.: US 8,014,056 B2
(45) Date of Patent: *Sep. 6, 2011

(54) DISPLAY ELEMENT AND METHOD OF DRIVING THE SAME

(75) Inventors: Noriyuki Kokeguchi, Tokyo (JP); Kaori Ono, Tokyo (JP)

(73) Assignee: Konica Minolta Holdings, Inc. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/519,663

(22) PCT Filed: Dec. 6, 2007

(86) PCT No.: PCT/JP2007/073574
§ 371 (c)(1),
(2), (4) Date: Jun. 17, 2009

(87) PCT Pub. No.: WO2008/075565
PCT Pub. Date: Jun. 26, 2008

(65) Prior Publication Data
US 2010/0091353 A1    Apr. 15, 2010

(30) Foreign Application Priority Data

Dec. 21, 2006 (JP) ................. 2006-344050
Dec. 21, 2006 (JP) ................. 2006-344051
Feb. 21, 2007 (JP) ................. 2007-040619

(51) Int. Cl.
G02F 1/153 (2006.01)
G02F 1/15 (2006.01)
G09G 3/19 (2006.01)

(52) U.S. Cl. ................. 359/268; 359/265; 345/49

(58) Field of Classification Search .......... 359/265–277, 359/245–247, 254, 242; 345/49, 105; 250/70; 438/929

See application file for complete search history.

(56) References Cited

U.S. PATENT DOCUMENTS

| 7,619,803 B2 * | 11/2009 | Kokeguchi et al. ........... 359/265 |
| 2004/0252099 A1 * | 12/2004 | Walder et al. ................. 345/105 |
| 2006/0203535 A1 | 9/2006 | Ishii et al. |

FOREIGN PATENT DOCUMENTS

| EP | 1 699 063 A1 | 9/2006 |
| JP | 7-270831 A | 10/1995 |
| JP | 2930860 B2 | 5/1999 |
| JP | 2003-241227 A | 8/2003 |
| JP | 2003-270670 A | 9/2003 |
| JP | 2003-270672 A | 9/2003 |
| JP | 2006-243353 A | 9/2006 |
| JP | 2006-267828 A | 10/2006 |
| JP | 2006-337457 A | 12/2006 |
| WO | WO2006/129424 * | 4/2006 |

OTHER PUBLICATIONS

International Search Report for International Application No. PCT/JP2007/073574 mailed Mar. 11, 2008 with English Translation.

* cited by examiner

*Primary Examiner* — Dawayne A Pinkney
(74) *Attorney, Agent, or Firm* — Cantor Colburn LLP

(57) ABSTRACT

Provided is a novel electrochemical display element which performs bright white display, high contrast black/white display and full-color display with a simple member configuration. A method for driving such display element is also provided. The display element contains an electrochromic compound, which is colored or has its color disappear due to oxidation or reduction, a metallic salt compound, an electrolyte and a white scattered material, between opposing electrodes. The display element substantially performs multiple color display of three colors or more, i.e., black display, white display and colored display other than black, by driving operation of the opposing electrodes.

17 Claims, No Drawings

DISPLAY ELEMENT AND METHOD OF DRIVING THE SAME

This is a U.S. national stage of application No. PCT/JP2007/073574, filed on 6 Dec. 2007. Priority under 35 U.S.C. §119(a) and 35 U.S.C. §365(b) is claimed from Japanese Application Nos. 2006-344050, filed 21 Dec. 2006, 2006-344051, filed 21 Dec. 2006, and 2007-040619, filed 21 Feb. 2007, the disclosures of which are also incorporated herein by reference.

FIELD OF TECHNOLOGY

The present invention relates to a novel electrochemically display element which can display multi-color by a single layer, and a method of driving the same.

TECHNICAL BACKGROUND

Recently, chance of getting and leading information of documents and images in a form of electronic information simpler than those in a form of usual printed material on paper is more increased accompanied with increasing in the rapidness of the processing speed of personal computer, spreading of network infrastructure and capacity glowing and cost lowering of data storage.

As the means for leading such the electronic information, liquid crystal displays and CRT are usually used and light emission type displays such as an organic electroluminescent are mainly applied recently. However, it is necessary to observe such the leading means for long time, particularly, when the electronic information is information of documents. Such the action is difficultly considered as a gentle means for the human. As the problems of such the light emission type displays, it has been known that eyes are fatigued by flicker, portability is low, posture for leading is limited and focusing on the still image is necessary and electric consumption is increased accompanied with prolongation of the leading time.

Although memory type reflective displays utilizing outside light which do not consume electric power for sustaining the image have been known as the means for compensating such the defects, such the displays are difficultly considered to have sufficient properties in the present condition by the following reasons.

In the system using a polarizing plate such as a reflective liquid crystal plate, the reflectivity is low as about 40% so that display of white image is insufficiently and majority of the production methods to be used for producing the constituting parts of the display is not always simple is utilized. A polymer dispersion type liquid crystal requires high voltage and the contrast of the obtained image is not insufficient since difference of between the refractive indexes of organic compounds. A polymer network type liquid crystal has problems that high voltage is required and a complex TFT circuit is necessary for improving the memorizing ability. A displaying element using electrophoresis requires high voltage such as 10 V or more and has anxiety about lowering in the durability caused by coagulation of the electrophoresis particles.

As a method of realizing full-color display, an electrochromic method is known, which is drivable at a low voltage of at most 3V. However, when sufficient black and white contrast and further colors are displayed with bright white, 3 layers of different colors need to be layered, resulting in the possibility of high cost due to a complicated element constitution. Further, a full-color electrochromic element via level mixing is known (for example, refer to Patent Document 1). However, in this method, high density black is unrealized due to level mixing, resulting in inadequate black and white contrast. Still further, it is known that a polypyridine compound is used for an electrochromic element (for example, refer to Patent Document 2). However, in this constitution, only 2 colors can be displayed as display colors and black display is specifically unrealized.

As a method to realize black display, an electrodeposition method (hereinafter referred to as an ED method) utilizing dissolution-deposition of a metal or a metallic salt is known (for example, refer to Patent Document 3). Such an ED method is an advantageous method to realize adequate black and white contrast, but in order to display full-color, it is necessary to use color filters of B, G, and R, or Y, M, and C, whereby there has been noted the problem that adequate black and white contrast via this method is unable to be utilized.

Patent Document 1: Unexamined Japanese Patent Application Publication (hereinafter referred to as JP-A) No. 2003-270670

Patent Document 2: Japanese Patent Publication No. 2930860

Patent Document 3: JP-A No. 2003-241227

DISCLOSURE OF THE INVENTION

Problems to be Solved by the Invention

In view of the above problems, the present invention was completed. An object of the present invention is to provide a newly developed electrochromic display element enabling to realize bright white display, high-contrast black and white display, and full-color display utilizing a simple member constitution; and a method for driving the same.

Means for Solving the Problems

The above object has been attained by the following constitutions:

1. A display element comprising an electrochromic compound which is colored or decolored due to oxidation or reduction, a metallic salt compound, an electrolyte, and white scattering material incorporated between opposed electrodes, wherein multi-color display of substantially 3 or more colors comprising black display, white display and colored display other than black are carried out by a driving operation of the opposite electrodes.

2. The display element of item 1, wherein the metallic salt compound comprises a compound containing silver salt.

3. The display element of item 1 or 2, wherein the electrochromic compound is colored due to oxidation and is decolored to be transparent due to reduction.

4. The display element of item 1 or 2, wherein the electrochromic compound is colored due to reduction and is decolored to be transparent due to oxidation.

5. The display element in any one of items 1 to 3, wherein the electrochromic compound comprises a compound represented by Formula (A):

Formula (A)

wherein $R_1$ represents a substituted or unsubstantiated aryl group, $R_2$ and $R_3$ each represents a hydrogen atom or a substituent, X represents >N—$R_4$, an oxygen atom or a sulfur atom, and $R_4$ represents a hydrogen atom or a substituent.

6. The display element in any one of items 1, 2 or 4, wherein the electrochromic compound comprises a compound represented by Formula (I) or Formula (2):

Formula (1)

$$R^1\text{—}(CH_2)_{m1}\text{—}N^+\text{=}\bigcirc\text{—}\bigcirc\text{=}N^+\text{—}(CH_2)_{n1}\text{—}R^2 \quad 2X_1^-$$

wherein $R^1$ and $R^2$ each represents a hydrogen atom, an aryl group or a heteroaryl group each having 14 or less carbon atoms; a branched alkylene group or an alkenylene group each having 10 or less carbon atoms; or a cycloalkylene group; n1 and m1 each represents an integer of 0 to 10; and $X_1^-$ represents an ion which neutralizes the charge, Formula (2)

$$(HO)_2(O)P\text{—}R^3\text{—}N^+\text{=}\bigcirc\text{—}\bigcirc\text{=}N^+\text{—}R^4 \quad 2X_2^-$$

wherein $R^3$ represents: —$(CH_2)_m$— wherein m represents an integer of 0 to 10; an arylene group or a heteroarylene group each having 14 or less carbon atoms, a branched alkylene group or an alkenylene group each having 10 or less carbon atoms or a cycloalkylene group; each of the arylene group, heteroarylene group, branched alkylene group, branched alkenylene group or cycloalkylene group may have a —P(O)(OH)$_2$ group through a —$(CH_2)_n$— group or may be arbitrarily substituted, wherein n represents an integer of 0 to 10; $R^4$ represents a group represented by —$(CH_2)_p$—$R^5$ wherein p represents an integer of 0 to 10 and $R^5$ represents —P(O)(OH)$_2$ group or an aryl group or a heteroaryl group each having 14 or less carbon atoms, and an alkyl group or an alkenyl group each having 10 or less carbon atoms or a cycloalkyl group or a hydrogen atom; and $X_2^-$ represents an ion which neutralizes the charge.

7. The display element in any one of items 1, 2 or 4, wherein the electrochromic compound comprises a compound represented by Formula (I) to Formula (VI):

Formula (I)

Formula (II)

Formula (III)

Formula (IV)

Formula (V)

Formula (VI)

wherein $R^1$ and $R^2$ each represents a hydrogen atom or a substituent; $R^3$ and $R^4$ each represents a hydrogen atom or a substituent; m and p each represents an integer of 0 to 4; X represents an oxygen atom or a sulfur atom; and $A^-$ represents a counter ion to balance charge.

8. The display element of items 1 or 2, wherein the electrochromic compound comprises a compound represented by Formula [1] to Formula [8]:

Formula [1]

wherein $R_1$ and $R_2$ each represents a substituent; $R_3$ represents a hydrogen atom or a substituent and when $R_3$ represents a hydrogen atom either $R_1$ or $R_2$ represents amino group; a and b each represents an integer of 0 to 5; when a and b each is 2 or more, 2 or more $R_1$'s or 2 or more $R_2$'s each may be the same or different; and adjacent $R_1$'s or $R_2$'s each may join to form a ring, Formula [2]

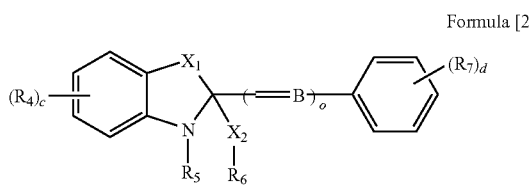

wherein $R_4$ and $R_7$ each represents a substituent; $R_5$ and $R_6$ each represents a alkyl group; $R_5$ and $R_6$ may join to form a ring or an ortho position of the phenyl group joining B and X2 may directly join to form a ring; $X_1$ represents —$CR_{30}R_{31}$—, —$NR_{32}$, —O— or —S—; $X_2$ represents —O— or —S—; B represents =CH— or =N—; c represents an integer of 0 to 4 and when c is 2 or more, 2 or more $R_4$'s each may be the same or different or adjacent $R_4$'s may join to form a ring; d is an integer of 0 to 5, and when d is 2 or more, 2 or more $R_7$'s each may be the same or different or adjacent $R_7$'s may join to form a ring; and o represents 1 or 2, Formula [3]

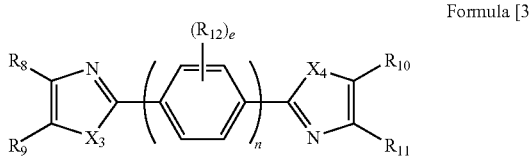

wherein $R_8$ to $R_{11}$ each represents a hydrogen atom or a substituent; $R_{12}$ represents a substituent; $X_3$ and $X_4$ each represents —$CR_{30}R_{31}$—, —$NR_{32}$, —O— or —S—; e represents an integer of 0 to 4 and when e is 2 or more, 2 or more $R_{12}$'s each may be the same or different or adjacent $R_{12}$'s may join to form a ring; and n represents 0 or 1, Formula [4]

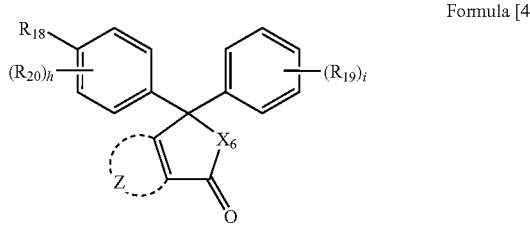

wherein $R_{18}$ represents a hydroxyl group, an alkoxy group or an amino group; $R_{19}$ and $R_{20}$ each represents a substituent; h is an integer of 0 to 4 and when h is 2 or more, 2 or more $R_{20}$'s each may be the same or different or adjacent $R_{20}$'s may join to form a ring; i is an integer of 0 to 5 and when i is 2 or more, 2 or more $R_{19}$'s each may be the same or different and adjacent $R_{19}$'s may join to form a ring, further adjacent $R_{19}$ and $R_{20}$ may join to form a ring; $X_6$ represents —O— or —$NR_{32}$; and Z represents a residual group needed to form an aromatic or heterocyclic ring, Formula [5]

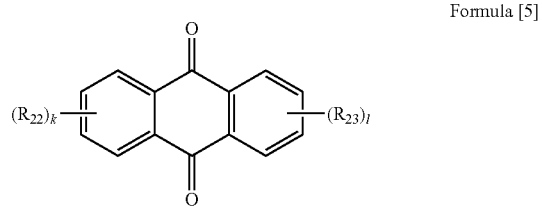

wherein $R_{22}$ and $R_{23}$ each represent a substituent; k and l each independently represent an integer of 0 to 4; when k and l represent 2 or more, 2 or more $R_{22}$'s or 2 or more $R_{23}$'s may be the same or different, and further adjacent $R_{22}$'s or $R_{23}$'s may join to form a ring, Formula [6]

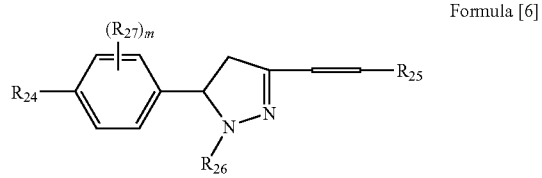

wherein $R_{24}$ represents a hydroxyl group, an alkoxy group, or an amino group; $R_{25}$ represents an aryl group or a heterocyclic group; $R_{26}$ represents a hydrogen atom, an alkyl group, an aryl group, a heterocyclic group, an acyl group, or a carbamoyl group; $R_{27}$ represents a substituent; m represents an integer of 0 to 4, when m represents 2 or more, 2 or more $R_{27}$'s each may be the same or different, and further adjacent $R_{27}$'s may join to form a ring, Formula [7]

wherein $R_{28}$ and $R_{29}$ each represent a substituent; n represents an integer of 0 to 4, when n represents 2 or more, 2 or more $R_{29}$'s each may be the same or different, and further adjacent $R_{29}$'s may join to form a ring; and Y represents an electron attractive group, Formula [8]

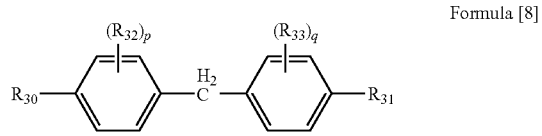

wherein $R_{90}$ and $R_{31}$ represent a hydrogen atom, a hydroxyl group, an alkoxy group, or an amino group; $R_{90}$ and $R_{31}$ do not represent a hydrogen atom simultaneously; $R_{92}$ and $R_{33}$ each represent a substituent; p and q each independently represent an integer of 0 to 4, when p and q are 2 or more, 2 or more $R_{22}$'s or 2 or more $R_{22}$'s each may be the same or different, adjacent $R_{22}$'s or $R_{22}$'s each may join to form a ring.

9. The display element in any one of items 1 to 8, wherein the electrochromic compound is chemically or physically adsorbed on a surface of at least one of the opposite electrodes.

10. The display element in any one of items 1 to 9, wherein the electrochromic compound comprises at least one of a absorption group containing $-CO_2H$, $-PO(OH)_2$, $-OPO(OH)_2$, $-SO_3H$ or $-Si(OR)_3$, wherein R represents a hydrogen atom or an alkyl group.

11. The display element in any one of items 1 to 10, wherein at least one of the opposite electrodes comprises a metal oxide porous layer and the electrochromic compound is supported on the metal oxide porous layer.

12. The display element in any one of items 1 to 11, wherein the white scattering material comprises $TiO_2$, $ZnO$ or $Al_2O_3$.

13. The display element in any one of items 1 to 12, wherein substantially black state is displayed by a cathode reaction.

14. The display element in any one of items 1 to 13, wherein a colored display other than black is conducted by a level arrangement of display areas which creates hues practically differing from one another.

15. The display element of claim 14, wherein different electrochromic compounds are supported on the metal oxide porous layer.

16. The display element of item 15, wherein different electrochromic compounds are separately coated on the metal oxide porous layer by an ink-jet method.

17. A method for driving the display element in any one of items 1 to 16, wherein the driving is carried out under conditions where the coloring overvoltage (VECW) and the decoloring overvoltage (VECE) of an electrochromic dye, and the deposition overvoltage (VAgW) and the dissolution overvoltage (VAgE) of silver of a silver salt compound satisfy all the conditions defined by following Relational expression (X):

VECW absolute value>VECE absolute value

VECW absolute value>VAgE absolute value

VAgW absolute value>VECE absolute value

VAgW absolute value>VAgE absolute value     Relational expression (X)

18. A method for driving of item 17, wherein the driving is carried out under conditions where the voltage (VW) between the opposite electrodes during the white display driving operation satisfies all the conditions defined by following Relational expression (Y):

VECW absolute value>VW>VECE absolute value

VECW absolute value>VW>VAgE absolute value

VAgW absolute value>VW>VECE absolute value

VAgW absolute value>VW>VAgE absolute value,     Relational expression (Y)

wherein VECW, VECE, VAgE, and VAgW have the same meanings as in Relational expression (X).

Effects of the Invention

According to the present invention, it was achieved a display element which is composed of simple constituting members and is drivable at low voltages exhibiting enhanced reflectance of white display and enhanced display speed, as well as having high stability for a change of environment of usage.

THE BEST EMBODIMENT FOR EMBODYING THE INVENTION

The best mode to carry out the present invention will now be detailed.

The display element of the present invention is characterized in that an electrochromic compound colored or decolored via oxidation or reduction, a metallic salt compound, an electrolyte, and a white scattering material are incorporated between opposite electrodes; and black display, white display, and multi-color display of at least 3 colors which is colored display other than black are practically carried out by a driving operation of the opposite electrodes.

Each of the components of the present invention will now be detailed.

[Metallic Salt Compounds]

With regard to metallic salt compounds according to the present invention, any compounds are usable provided that these compounds are metallic species-containing salts which can be subjected to dissolution-deposition on at least one of opposite electrodes via a driving operation of the opposite electrodes. Preferable metallic species include silver, bismuth, copper, nickel, iron, chromium, and zinc. Of these, silver and bismuth are specifically preferable.

[Compound Containing Silver]

A compound containing silver according to the present invention is common designations of a compound containing silver in their chemical structure, such as silver oxide, silver sulfide, sliver halide, silver complex compound, or a silver ion. The phase states such as a solid state, a state solubilized to liquid, a gas state, and charge state types such as neutral, anionic or cationic are not particularly considered. Preferable compound for a display element of the present invention includes a well-known compound containing silver, or a compound containing silver in their chemical structure such as silver iodide, silver chloride, silver bromide, silver oxide, silver sulfide, silver citrate, silver acetate, silver behenate, silver p-toluenesulfonate, silver trifluoromethanesulfonate, silver salts with mercapto group, silver complex with iminodiacetate. Among them, a compound which does not have halogen, carbonic acid or a nitrogen atom having coordination ability with silver, for example silver p-toluenesulfonate, is especially preferable as silver salt.

The concentration of silver ions contained in the electrolyte of the present invention is preferably, 0.2 mol/kg≦[Ag] ≦2.0 mol/kg. When the concentration of silver ions is less than 0.2 mol/kg, the silver ion solution will become so dilute that the resulting driving speed becomes delayed. When the concentration of silver ions is more than 2.0 mol/kg, the solubility of the silver ions will become so deteriorated that it may occur precipitation during storage at low temperature and it is not advantageous.

[Basic Structure of Display Element]

In the display element of the present invention, the display section is provided with a pair of opposed electrodes arranged in an opposed position to each other. Electrode 1, one of the opposed electrodes, close to the display section is provided with a transparent electrode such as an ITO electrode, and the other, electrode 2, is provided with a metal electrode such as a silver electrode. An electrolyte, incorporating silver or a compound containing silver in its chemical structure, is arranged between electrode 1 and electrode 2. By applying voltage of positive and negative polarity between the opposed electrodes, oxidation-reduction reaction of silver is performed on electrode 1 and electrode 2, whereby a black silver image in the reduction state and a transparent silver state in the oxidation state can reversibly be converted.

An electrochromic compound of the present invention is described below.

An electrochromic compound of the present invention is a compound (hereinafter also called as a EC compound) which shows a phenomenon that a properties of optical absorption of the compound (color or light transmission characteristics) changes reversibly (Electrochromism) by an electrochemical oxidation-reduction. An electrochromic compound used in the present invention is described below.

[Compound Represented by Formula (A)]

Further, an electrochromic compound in the present invention represented by foresaid Formula (A) is explained.

In Formula (A), $R_1$ represents a substituted or non-substituted aryl group, $R_2$, $R_3$ each represent a hydrogen atom or a substituent, X represents >N—$R_4$, an oxygen atom or a sulfur atom, and $R_4$ represents a hydrogen atom or a substituent.

In Formula (A), $R_1$ represents a substituted or non-substituted aryl group, $R_2$, $R_3$ each represent a hydrogen atom or a substituent. Examples of a substituent represented by $R_1$, $R_2$ or $R_3$ include: an alkyl group (for example, a methyl group, an ethyl group, a propyl group, an isopropyl group, a tert-butyl, a pentyl group and a hexyl group), a cycloalkyl group (for example, a cyclohexyl group and a cyclopentyl group), and an alkenyl group, a cycloalkenyl group, an alkynyl group (for example, a propargyl group), a glycidyl group, an acrylate group, a methacrylate group, an aromatic group (for example, a phenyl group, a naphthyl group and an anthracenyl group), a heterocycle group (for example, a pyridyl group, a thiazolyl group, an oxazolyl group, an imidazolyl group, a furyl group, a pyrrolyl group, a pyrazinyl group, a pyrimidinyl group, a pyridazinyl group, a selenazolyl group, a thryhorany group, a piperizinyl group, a pyrazolyl group and a tetrazolyl group) an alkoxy group (for example, a methoxy group, an ethoxy group, a propyloxy group, a pentyloxy group, a cyclopentyloxy group, a hexyloxy group and a cyclohexyloxy group), an aryloxy group (for example, a phenoxy group), an alkoxycarbonyl group (for example, a methyloxycarbonyl group, an ethyloxycarbonyl group and a butyloxycarbonyl group), an aryloxycarbonyl group (for example, a phenyloxycarbonyl group), a sulfonamide group (for example, a methanesulfonamide group, an ethanesulfonamide group, a butanesulfonamide group, a hexane sulfonamide group, a cyclohexane sulfonamide group and a benzenesulfonamide group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, a phenylaminosulfonyl group and 2-pyridylaminosulfonyl group), a urethane group (for example, a methylureido group, an ethylureido group, and a pentylureido group, a cyclohexylureido group, a phenylureido group and 2-pyridylureido group), an acyl group (for example, an acetyl group, a propionyl group, a butanoyl group, and a hexanoyl group, a cyclohexanoyl group, a benzoyl and a pyridinoyl group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, a phenylaminocarbonyl group and a 2-pyridylaminocarbonyl group), an acylamino group (for example, an acetylamino group, a benzoylamino group and a methylureido group), an amide group (for example, an acetamide group, a propioneamide group, a butaneamide group, a hexaneamide group and a benzamide group), a sulfonyl group (for example, a methylsulfonyl group, an ethylsulfonyl group, a butylsulfonyl group, a cyclohexylsulfonyl group, a phenylsulfonyl group and a 2-pyridyl sulfonyl group), a sulfonamide group (for example, a methylsulfonamide group, an octylsulfonamide group, a phenylsulfonamide group and a naphthylsulfonamide group), an amino group (for example, an amino group, an ethylamino group, a dimethylamino group, a butylamino group, a cyclopentylamino group, an anilino group and 2-pyridylamino group), a halogen atom (for example, a chlorine atom, a bromine atom and an iodine atom), a cyano group, a nitro group, a sulfo group, a carboxyl group, a hydroxyl group, a phosphono group (for example, a phosphonoethyl group, a phosphonopropyl group and a phosphonooxyethyl group) and an oxamoyl group. These groups may further be substituted with these groups.

$R_1$ is a substituted or unsubstituted aryl group and preferably a substituted or unsubstituted phenyl group and further preferably a substituted or unsubstituted 2-hydroxyphenyl group or 4-hydroxyphenyl group.

$R_2$ and $R_3$ each are preferably an alkyl group, a cycloalkyl group, an aromatic group or a heterocycle group, more preferably, one of $R_2$ and $R_3$ is a phenyl group and the other is an alkyl group and further more preferably, both of $R_2$ and $R_3$ are a phenyl group.

X is preferably >N—$R_4$. $R_4$ is preferably a hydrogen atom, an alkyl group, an aromatic group, a heterocycle group or an acyl group and more preferably a hydrogen atom, an alkyl group having 1 to 10 carbon atoms, an aryl group having 5 to 10 carbon atoms or an acyl group.

Example of a concrete compound of an electrochromic compound represented by Formula (A) will be shown below, however, the present invention is not limited to these exemplified compounds.

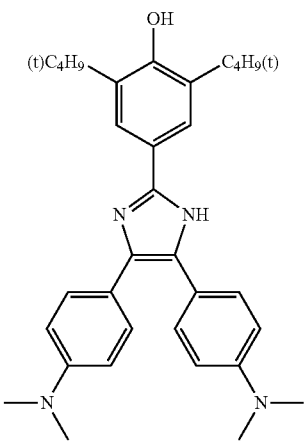

1

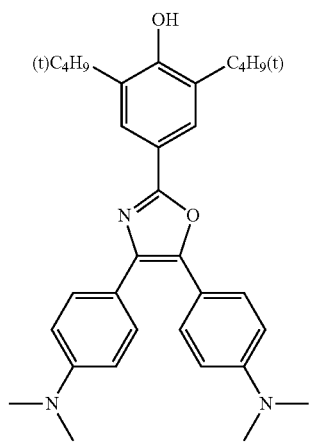

2

3
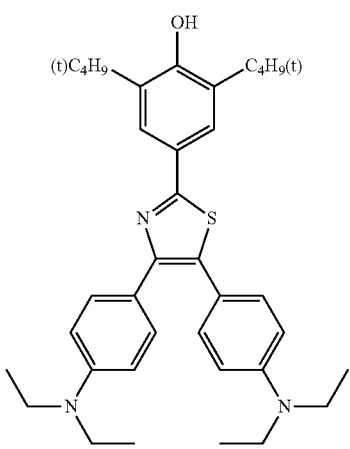
4
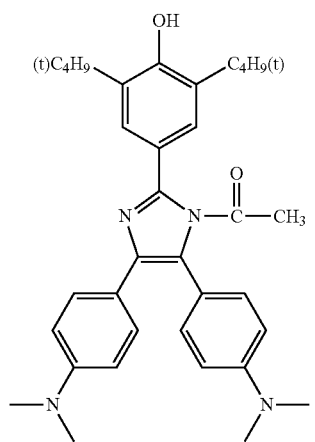
5
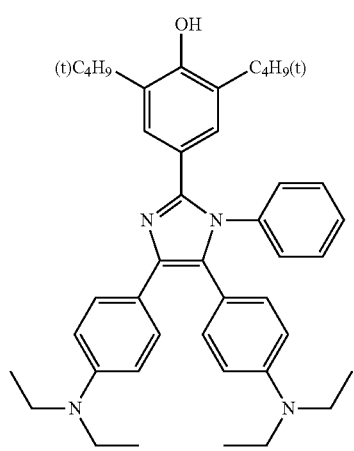
6
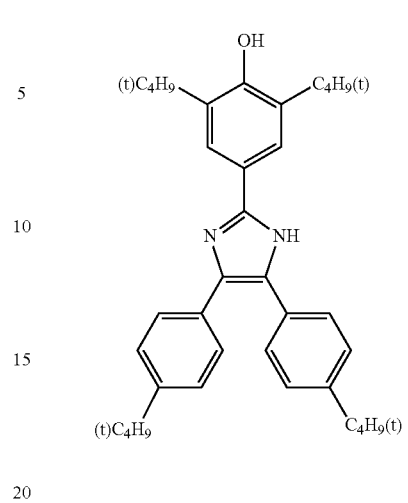
7
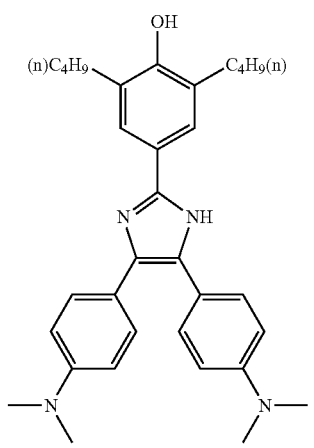
8
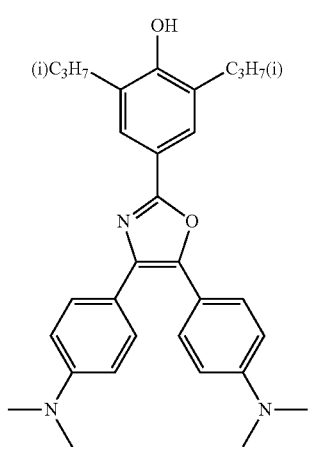

-continued
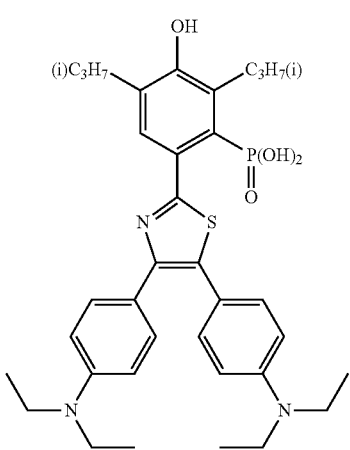
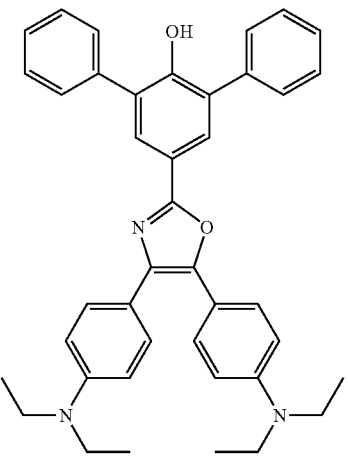
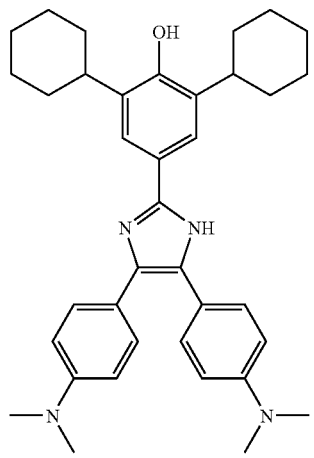
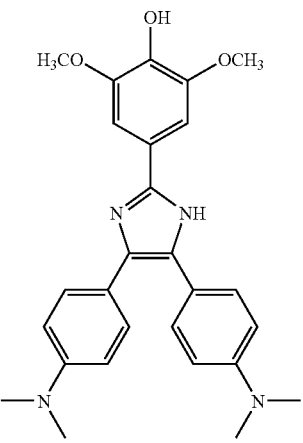
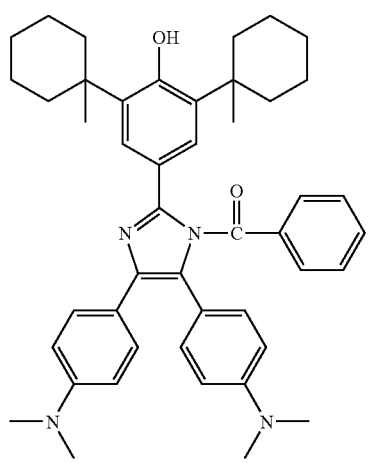
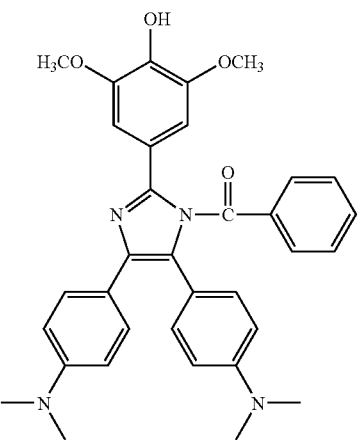

15
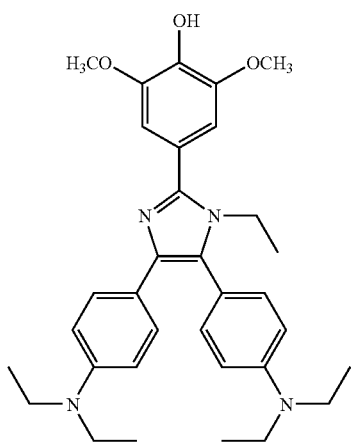
16
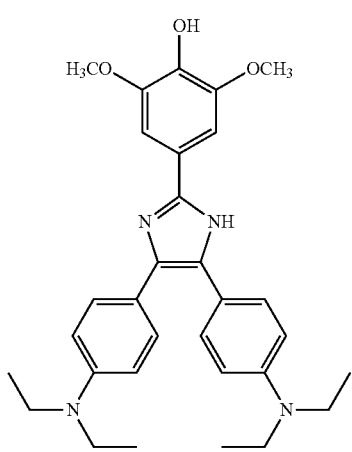
17
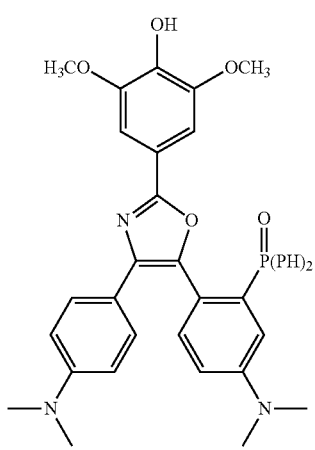
18
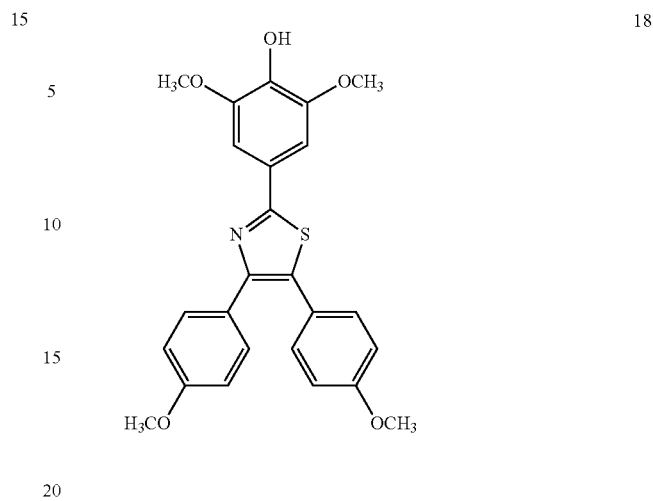
19
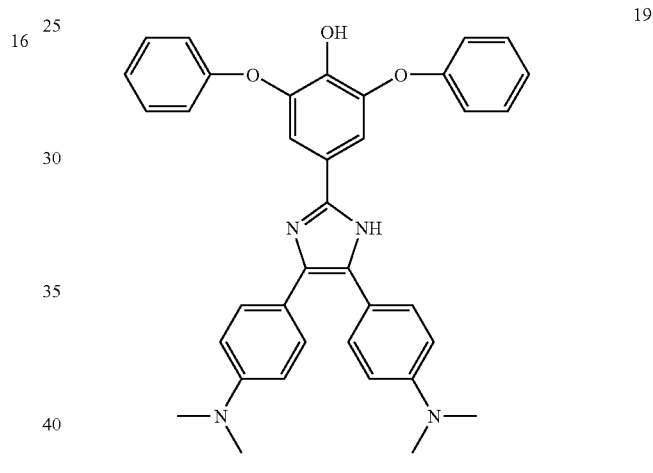
20
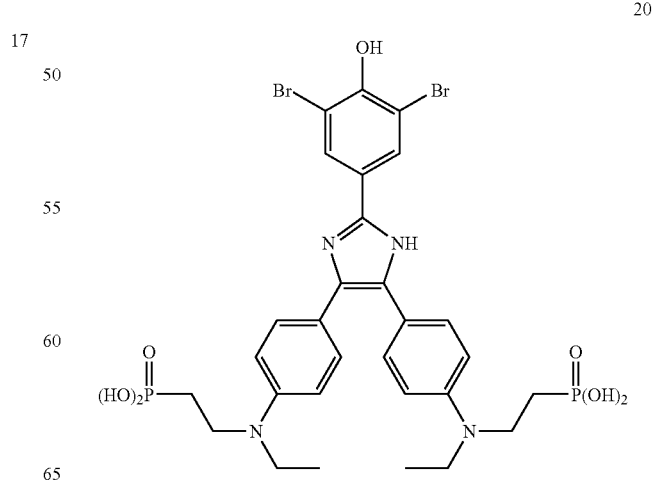

17
-continued
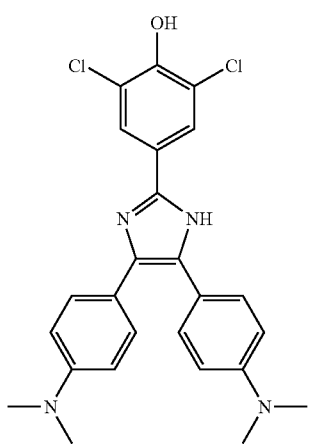
21
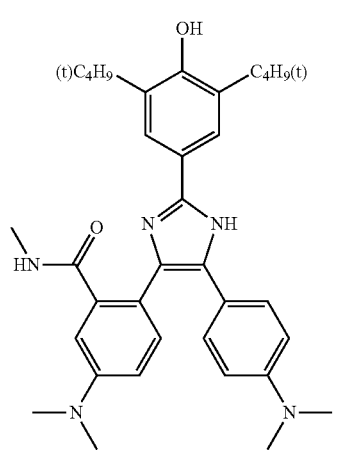
22
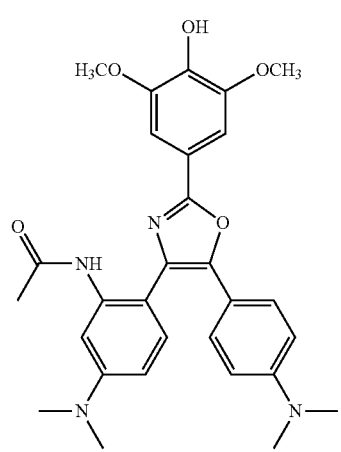
23
18
-continued
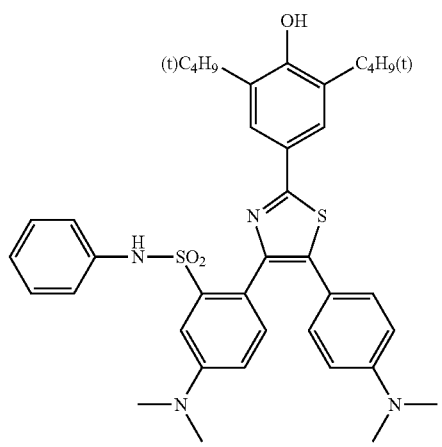
24
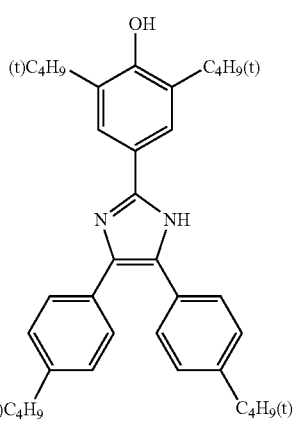
25
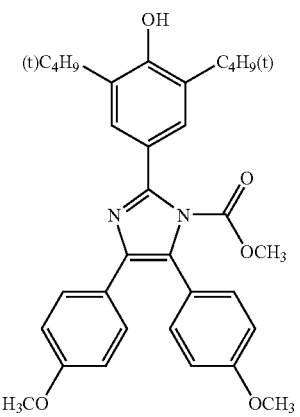
26
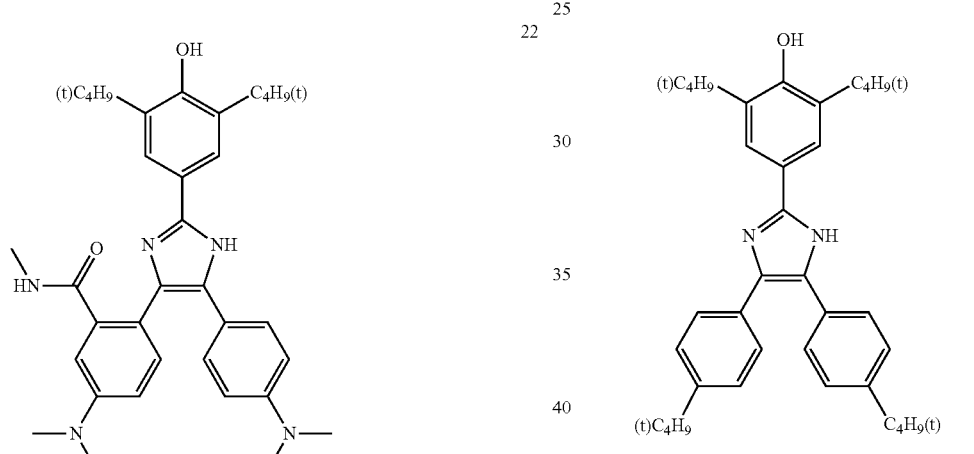

27
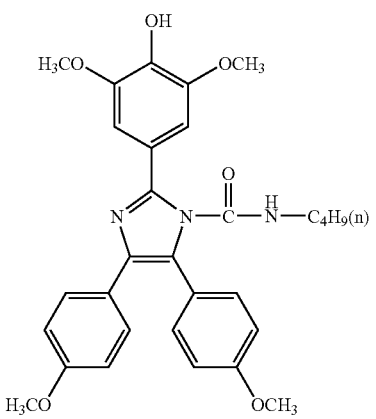
28
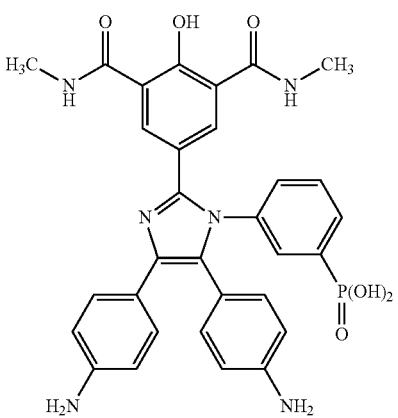
29
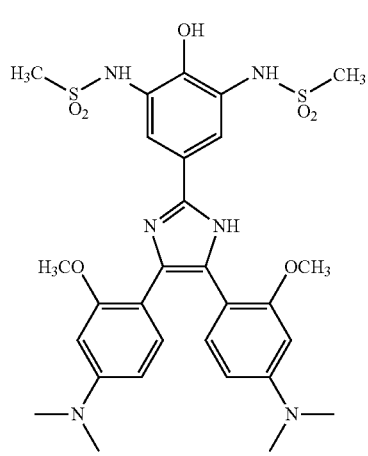
30
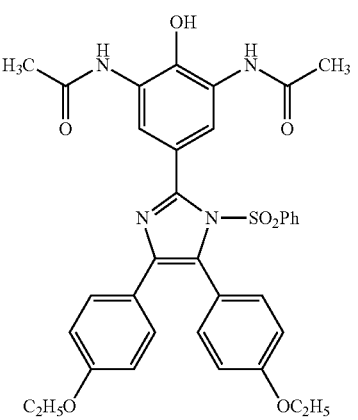
31
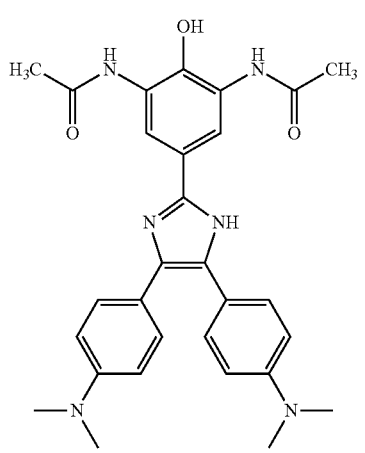
32
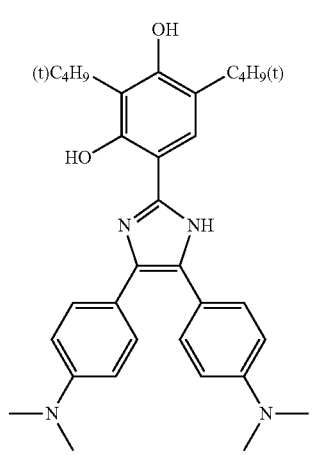

33
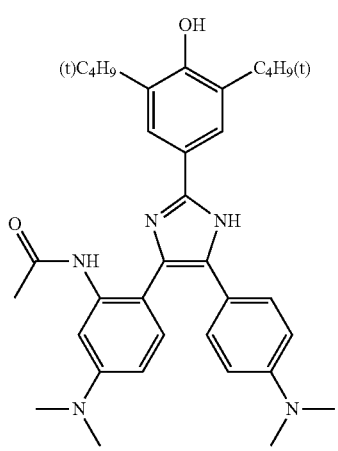
34
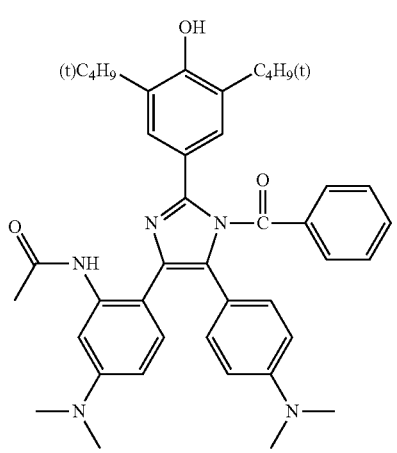
35
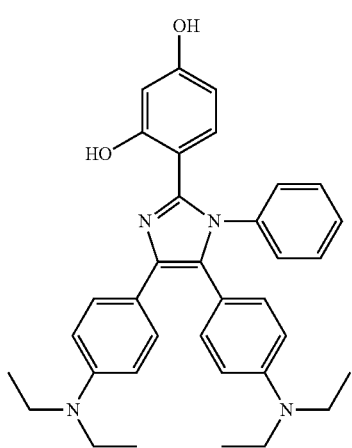
36
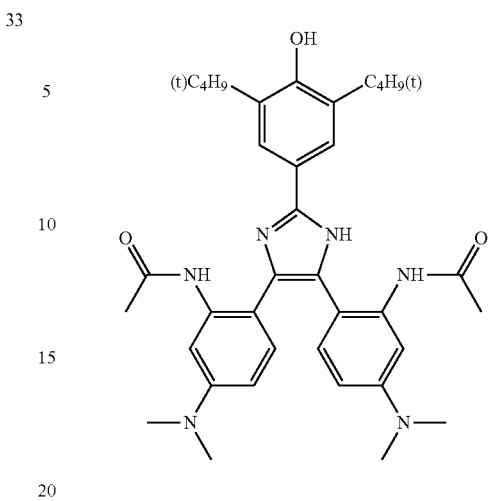
37
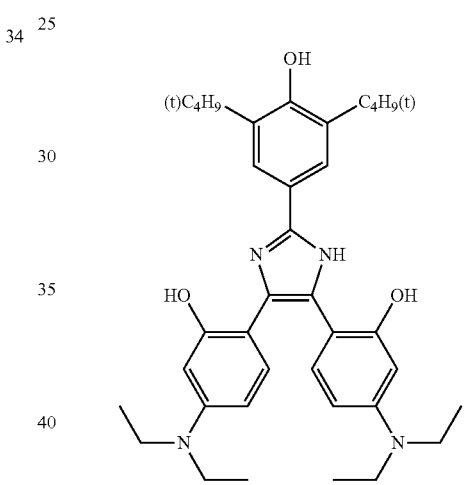
38
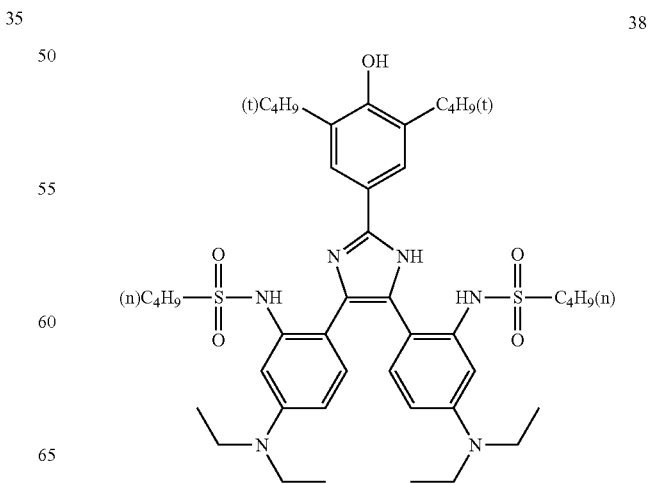

39
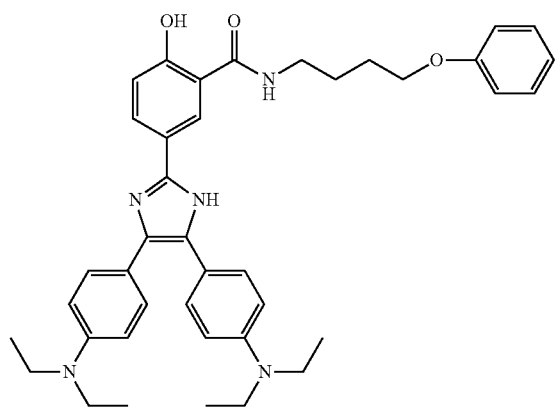
42
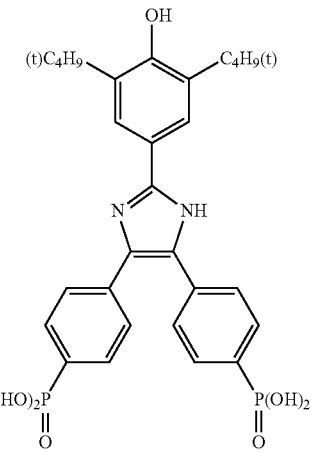
40
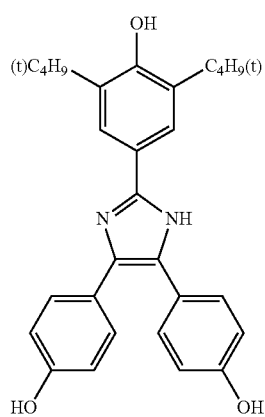
43
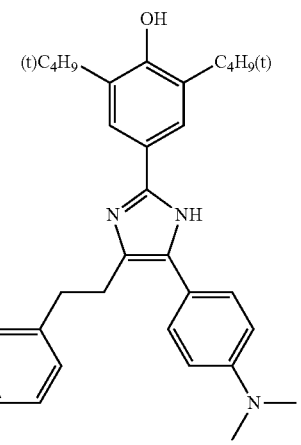
41
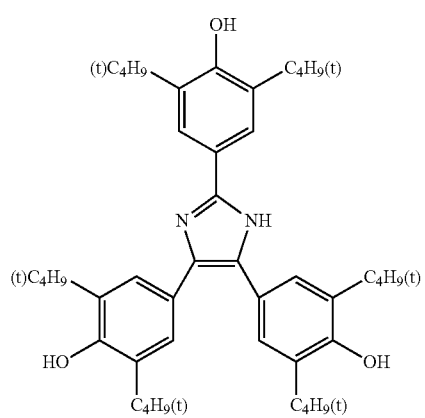
44
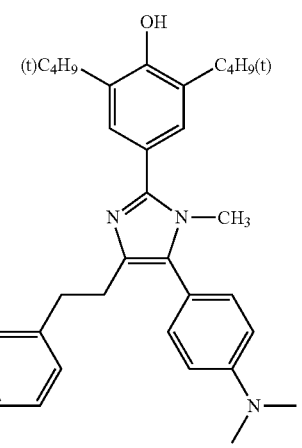

25 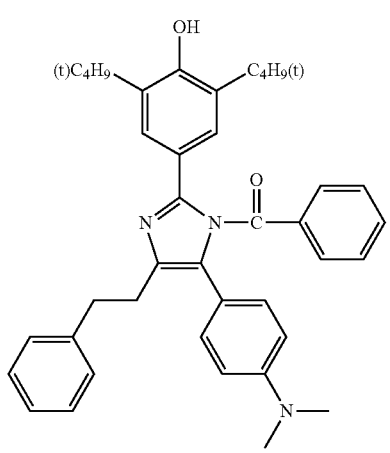
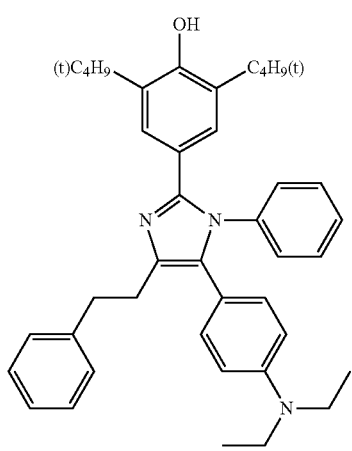 46
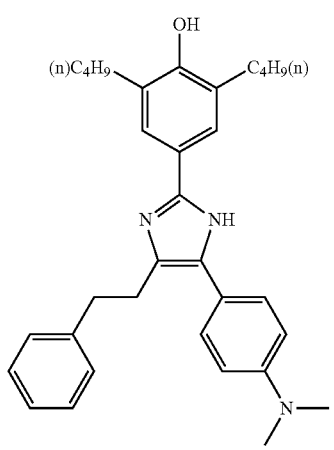 47
26 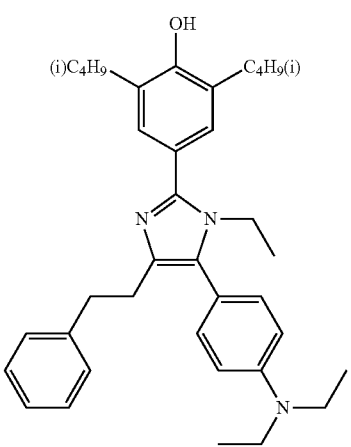 48
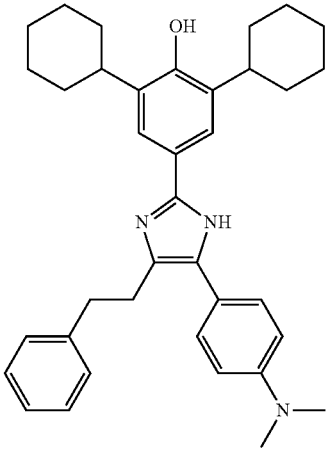 49
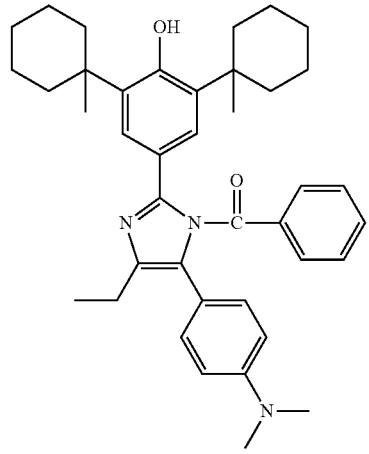 50

27
-continued
51
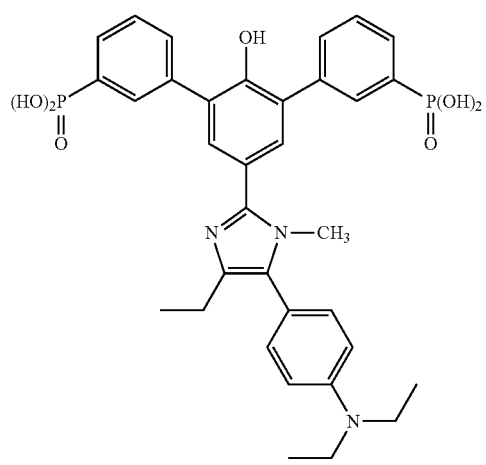
28
-continued
54
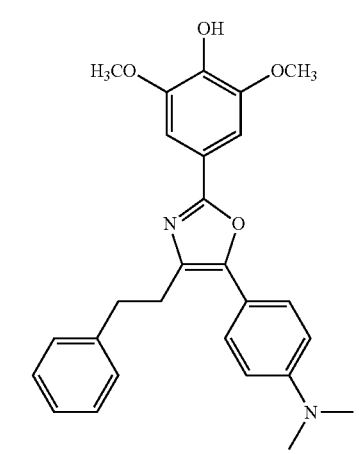
52
55
53
56

29 | 30
-continued | -continued
57
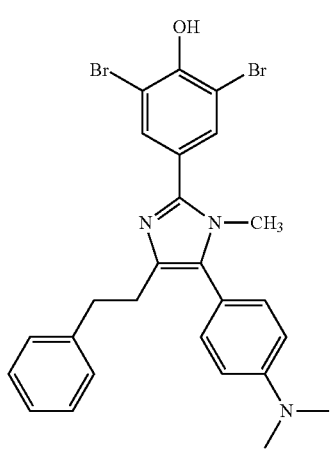
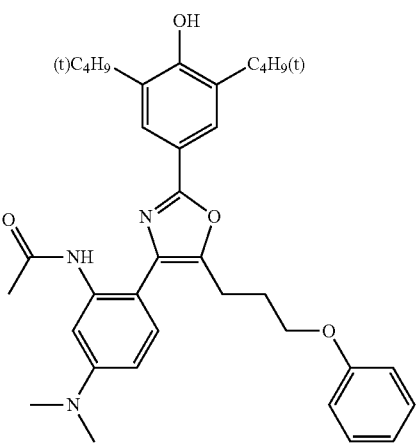
58
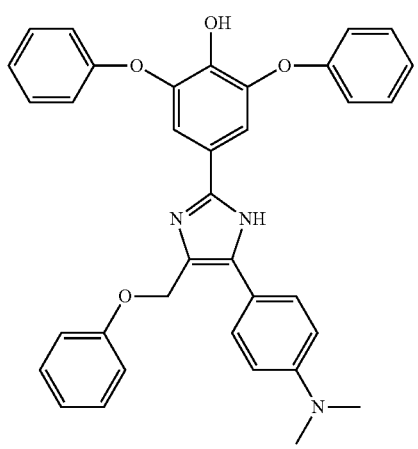
61
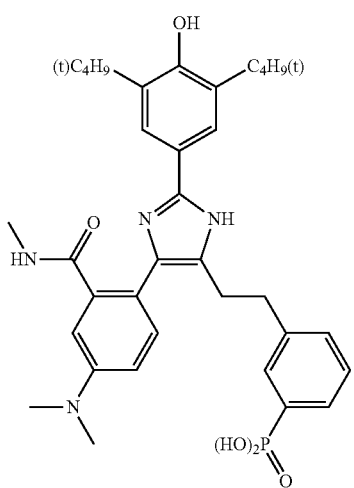
59
62
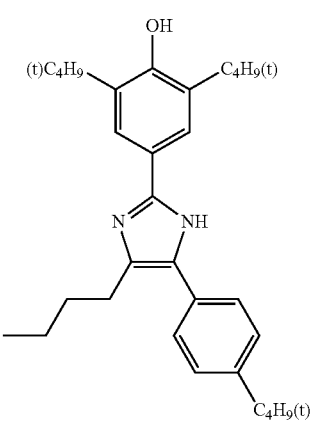

-continued
63
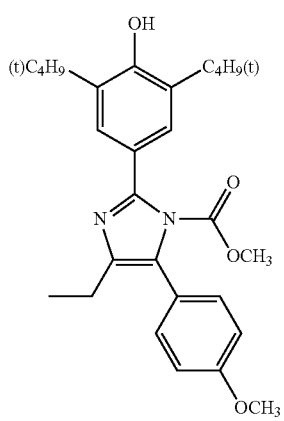
64
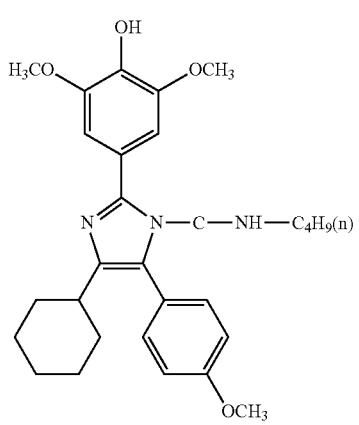
65
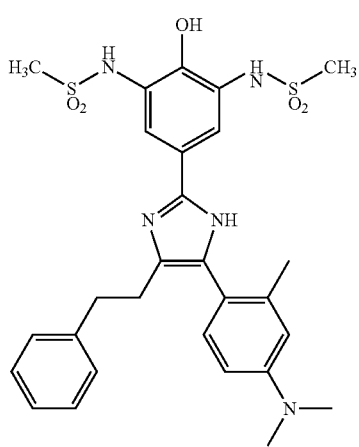
66
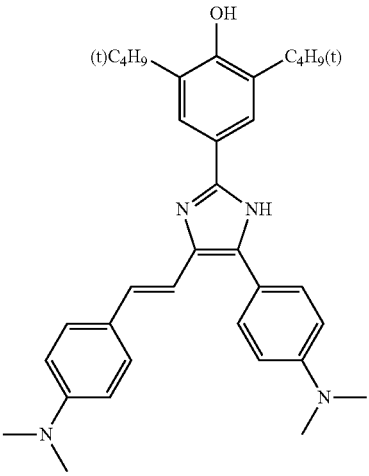
67
68
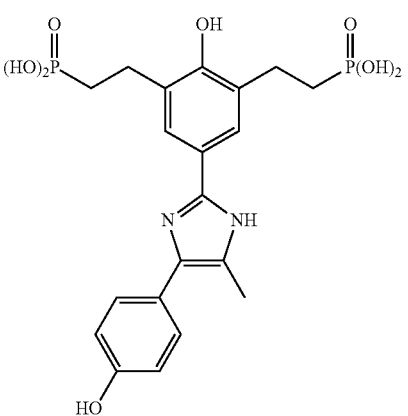

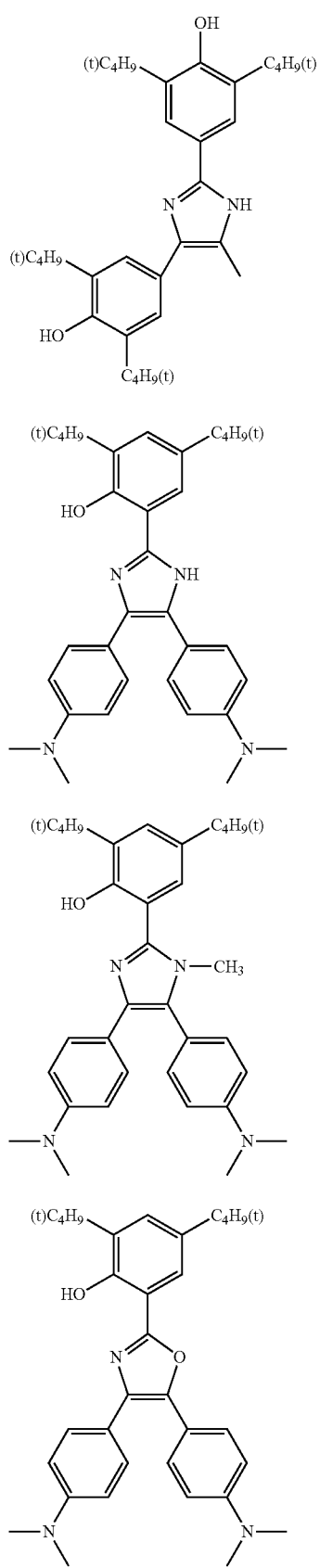
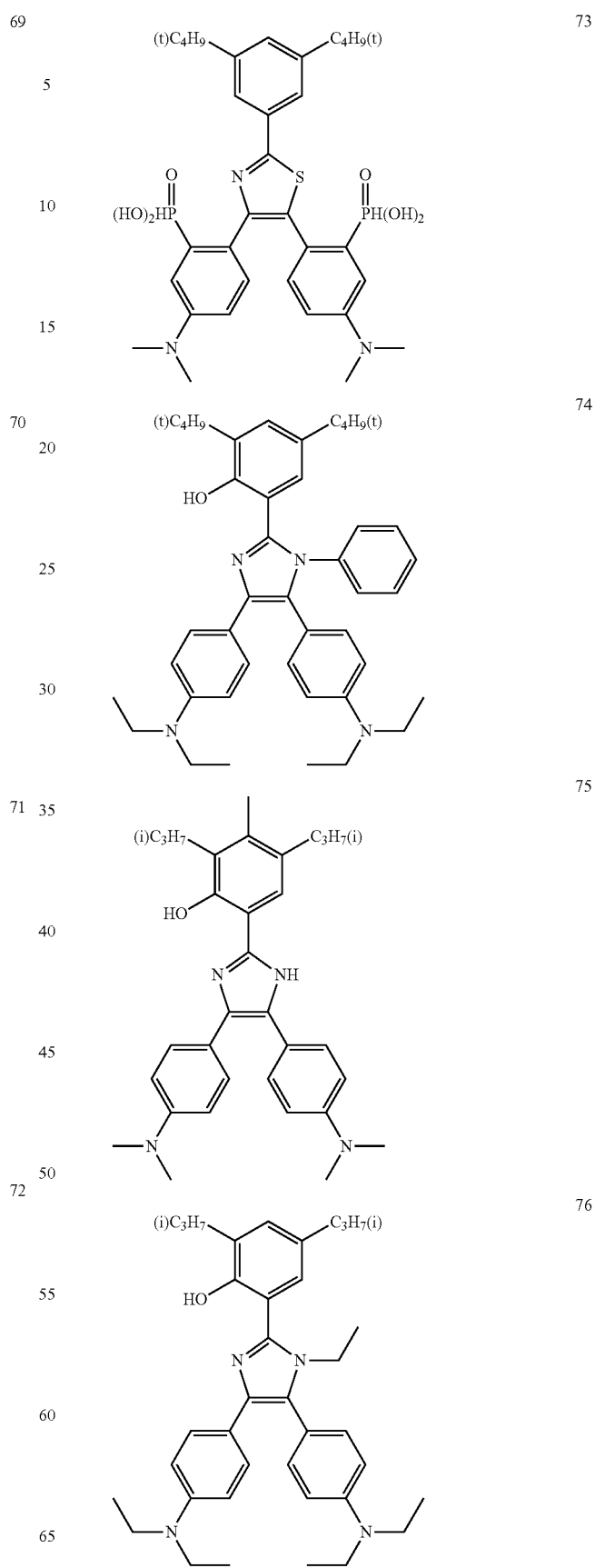

-continued
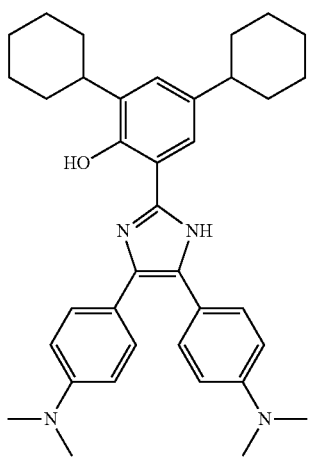
77
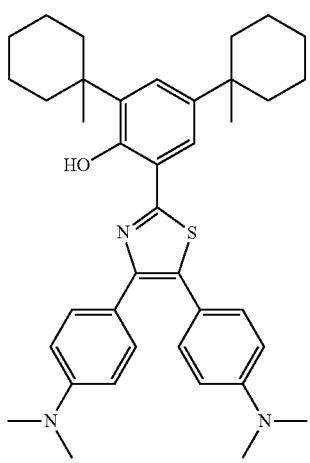
78
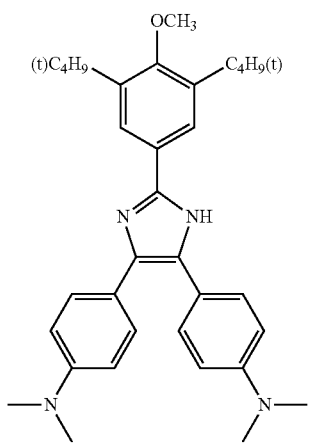
79
-continued
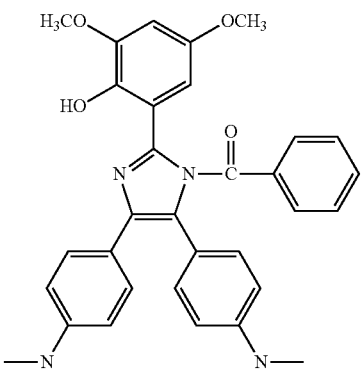
80
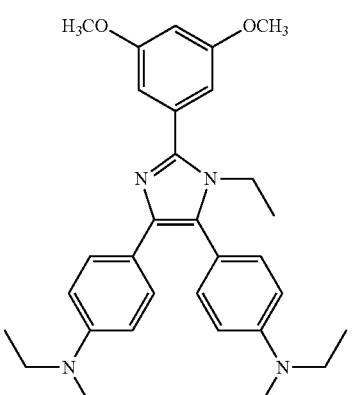
81
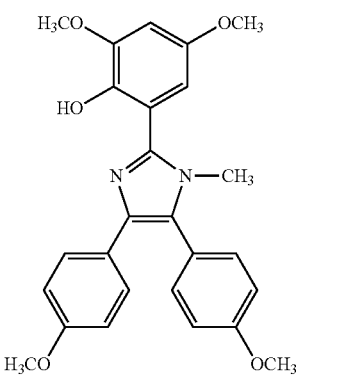
82
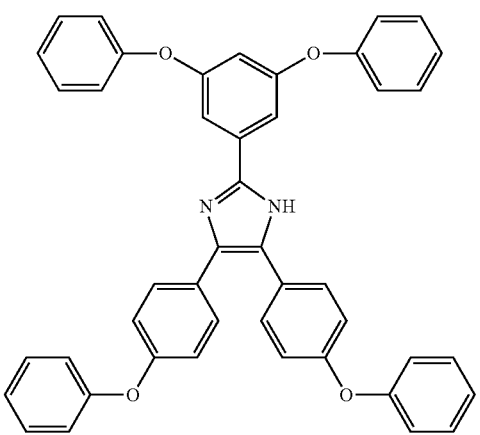
83

84
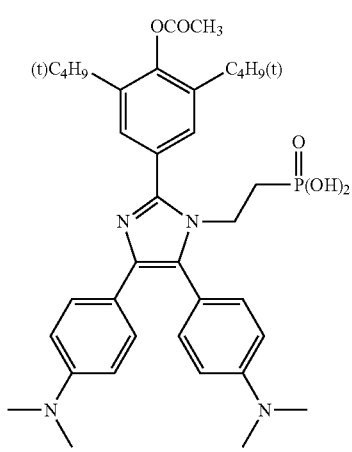
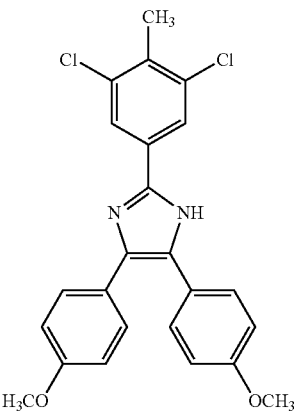
85
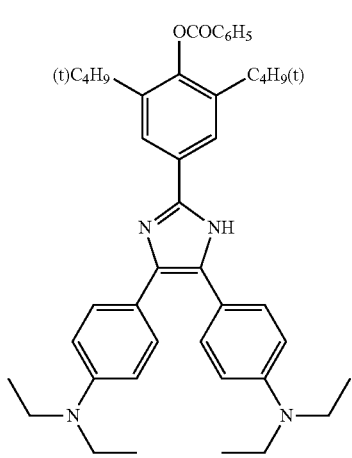
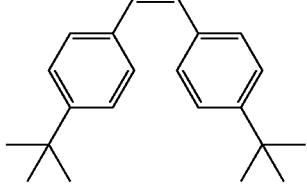
86
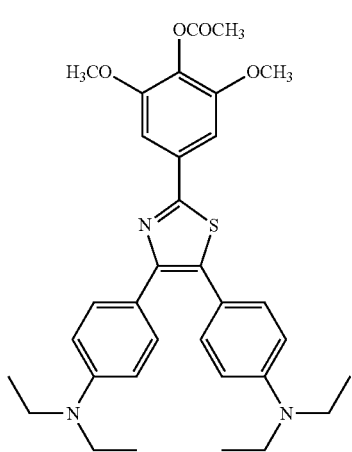
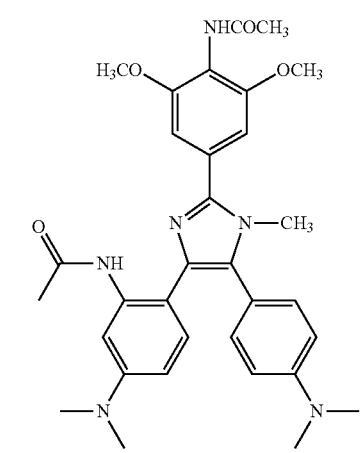

90
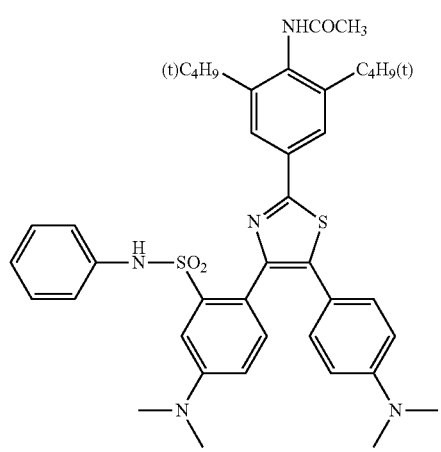
91
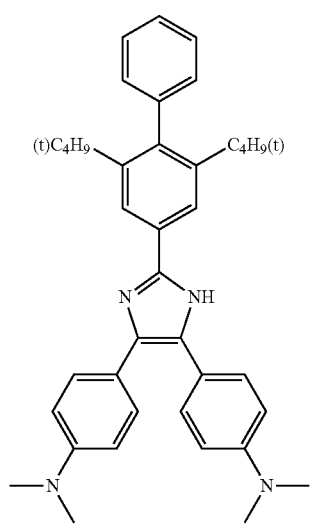
92
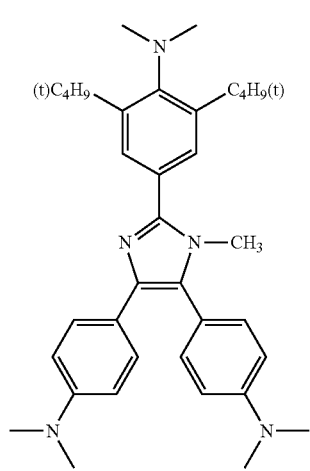
93
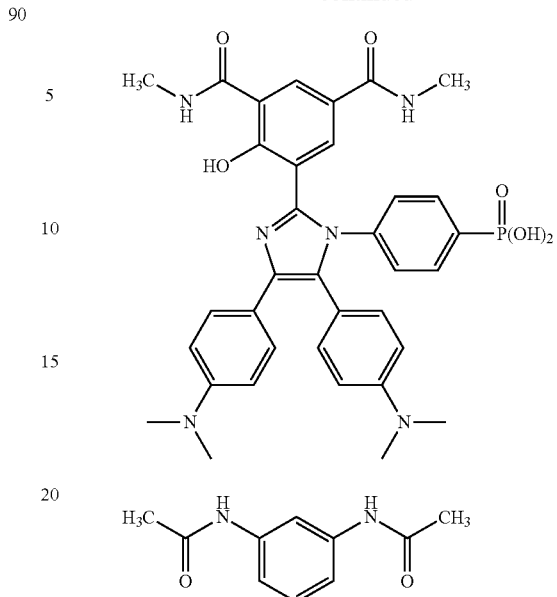
94
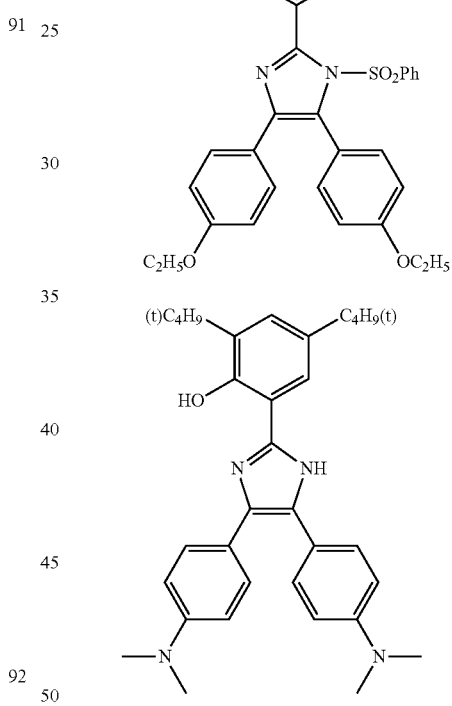
95
96
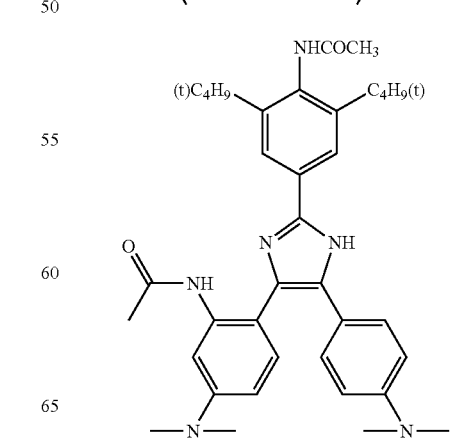

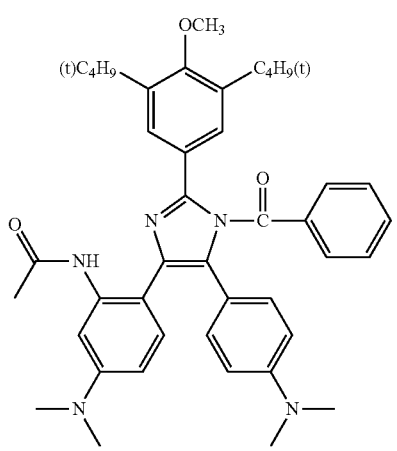
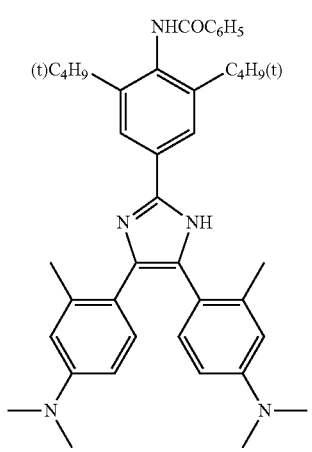
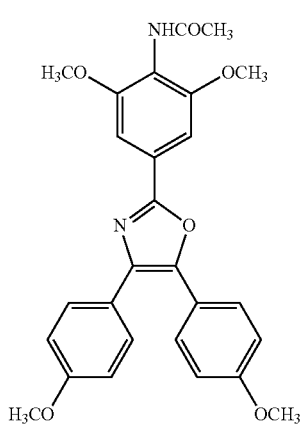
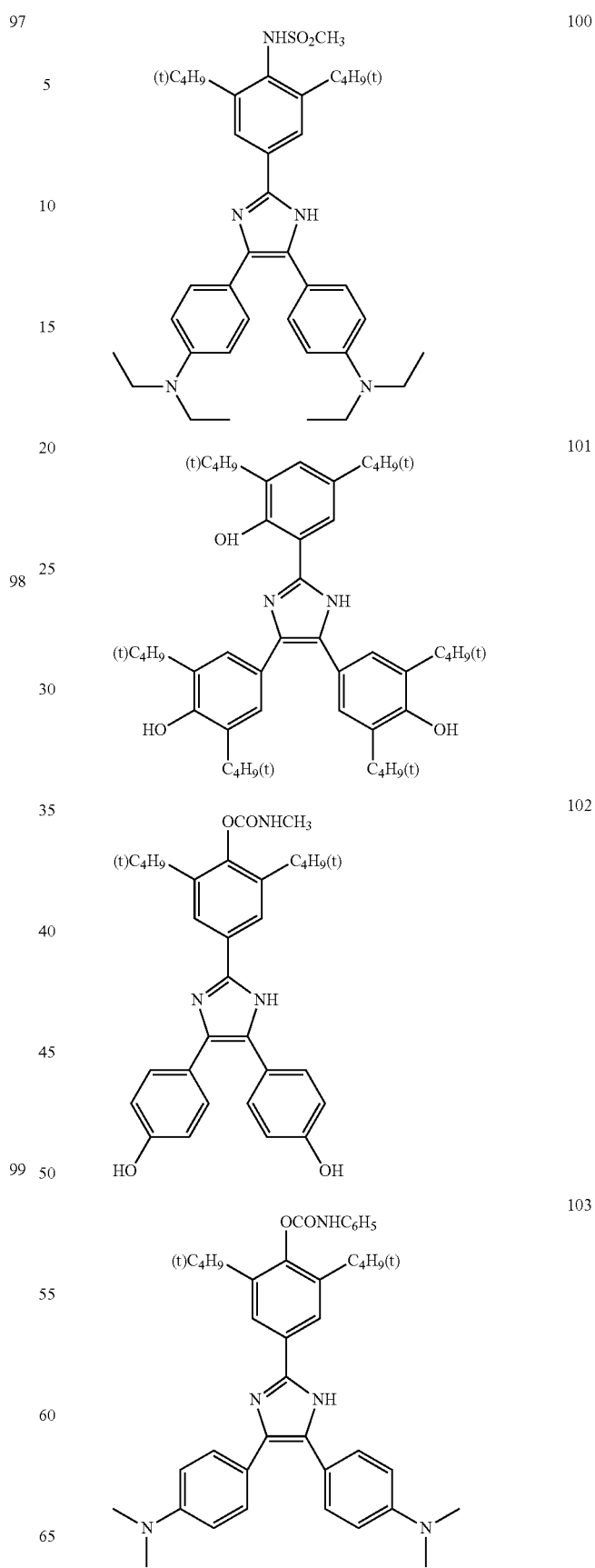

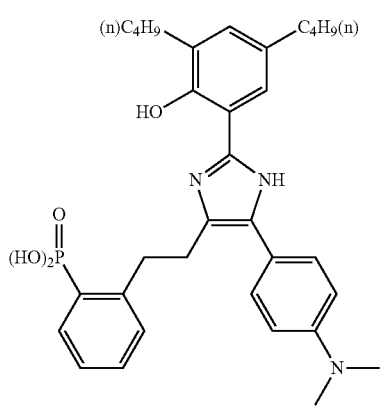
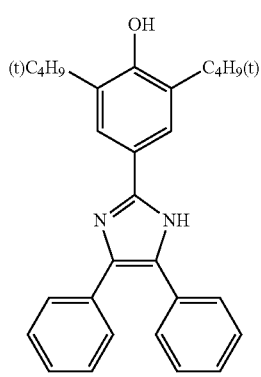
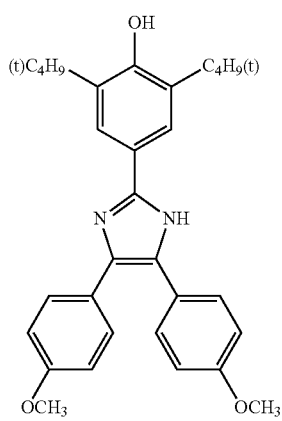
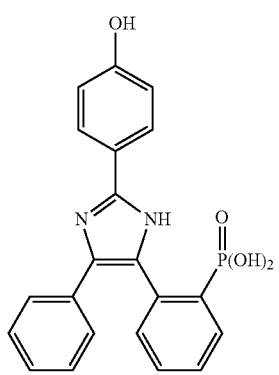
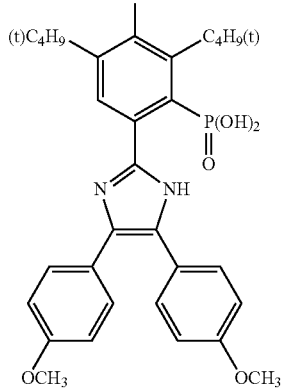
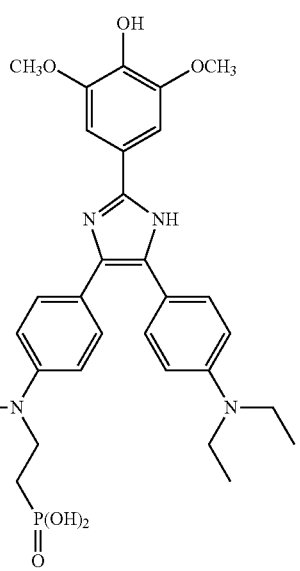
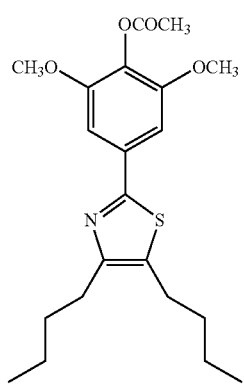

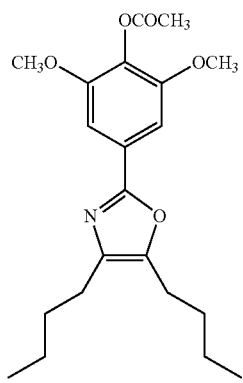
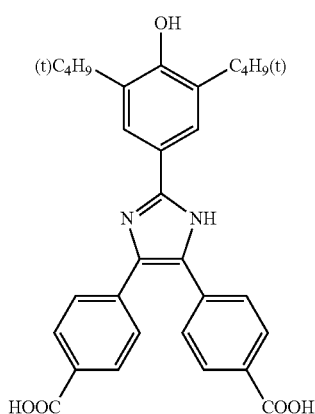

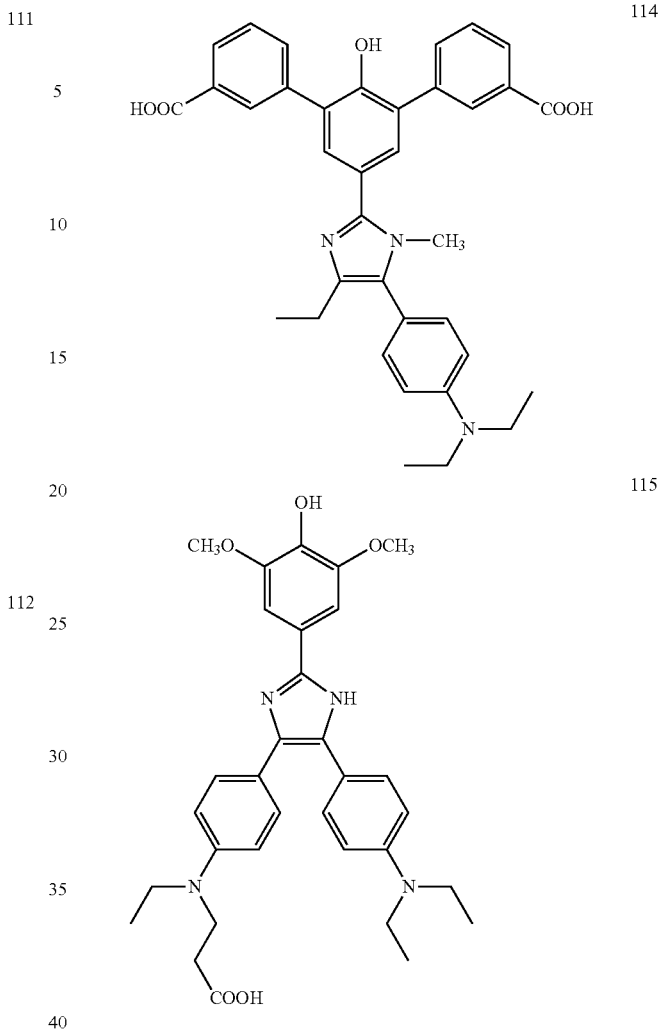

[Compound Represented by Formula (1) and Formula (2)]

viologen compound represented by Formula (1) which is preferably utilized in the present invention will now be described.

In Formula, $R^1$ and $R^2$ each represents a hydrogen atom, an aryl group or a heteroaryl group each having 14 or less carbon atoms; a branched alkylene group or an alkenylene group each having 10 or less carbon atoms; or a cycloalkylene group; n1 and m1 each represents an integer of 0 to 10; and X represents an ion which neutralizes the charge.

An aryl group, a heteroaryl group, a branched alkyl group, an alkenylene group or a cycloalkyl group each having 10 or less carbon atoms each may further have a substituent. Examples of the substituent include: a lower alkyl group, a lower alkenyl group, a phenyl-substituted lower alkyl group, a diphenyl-substituted lower alkyl group, a phenyl group, a phenoxy group, a lower alkanoyloxy group, a halogen atom, an amino group, a cyano group, a nitro group, a lower alkylamino group, a di-(lower alkyl)amino group, a phenylamino group, a lower alkanolamino group, a benzoylamino group, a lower alkylsulfonylamino group, a phenylsulfonylamino group, a lower alkanoyl group, a benzoyl group, a carboxyl group, a lower alkoxycarbonyl group, a carbamoyl group, an N-lower alkylcarbamoyl group, an N,N-di-(lower alkyl)carbamoyl group, an ureido group, an N-lower alkylureido group, a lower alkylsulfonyl group, a phenylsulfonyl group, a hydroxyl group, a lower alkoxy group, an amino group, a lower alkylamino group, a di-(lower alkyl)amino group, a halogen atom, a carboxyl group, or a lower alkoxy group substituted with a lower alkoxycarbonyl group, an alkoxy group having 3-7 carbon atoms, and a divalent methylenedioxy group.

The compound represented by Formula (1) includes a compound represented by Formula (2) to be described later. Herein, as specific compound examples, examples of compounds other than the compound represented by Formula (2) will now be listed.

(1-1) 1,1'-Di-n-octyl-4,4'-bipyridinium dibromide
(1-2) 1,1'-Di-n-octyl-4,4'-bipyridinium bis-hexafluorophosphate
(1-3) 1,1'-Di-n-octyl-4,4'-bipyridinium dichloride
(1-6) 1-Methyl-1'-n-octyl-4,4'-bipyridinium dichloride
(1-7) 1-Methyl-1'-(4-methylphenyl)-4,4'-bipyridinium dichloride
(1-8) 1-n-Octyl-1'-(4-cyanophenyl)-4,4'-bipyridinium dichloride
(1-9) 1-n-Octyl-1'-(4-fluorophenyl)-4,4'-bipyridinium dichloride
(1-10) 1,1'-Bis(3-propylphenyl)-4,4'-bipyridinium dichloride
(1-12) 1,1'-Bis(3-propylphenyl)-4,4'-bipyridinium bis-hexafluorophosphate
(1-13) 1,1'-Bis(2,4,6-trimethylphenyl)-4,4'-bipyridinium dichloride
(1-14) 1,1'-Bis(2,4,6-trimethylphenyl)-4,4'-bipyridinium bis-hexafluorophosphate
(1-15) 1,1'-Bis(naphthyl)-4,4'-bipyridinium dichloride
(1-16) 1,1'-Bis(4-cyanonaphthyl)-4,4'-bipyridinium dichloride
(1-17) 1,1'-Bis(4-methylphenyl)-4,4'-bipyridinium dichloride
(1-18) 1,1'-Bis(4-cyanophenyl)-4,4'-bipyridinium dichloride
(1-19) 1,1'-Bis(4-fluorophenyl)-4,4'-bipyridinium dichloride
(1-10) 1,1'-Bis(4-phenoxyphenyl)-4,4'-bipyridinium dichloride
(1-21) 1,1'-Bis(4-t-butylphenyl)-4,4'-bipyridinium dichloride
(1-22) 1,1'-Bis(2,6-dimethylphenyl)-4,4'-bipyridinium dichloride
(1-23) 1,1'-Bis(3,5-dimethylphenyl)-4,4'-bipyridinium dichloride
(1-24) 1,1'-Bis(4-benzophenone)-4,4'-bipyridinium dichloride
(1-25) 1-Benzyl-1'-(3-propylphenyl)-4,4'-bipyridinium dichloride
(1-26) 1-Benzyl-1'-(3-propylphenyl)-4,4'-bipyridinium bis-hexafluorophosphate
(1-27) 1-Benzyl-1'-ethyl-4,4'-bipyridinium dichloride
(1-28) 1-Benzyl-1'-(2,4-dinitrophenyl)-4,4'-bipyridinium dichloride
(1-29) 1-Benzyl-1'-(2,4-dinitrophenyl)-4,4'-bipyridinium bis-hexafluorophosphate
(1-30) 1-Benzyl-1'-(4-phenoxyphenyl)-4,4'-bipyridinium dichloride
(1-31) 1-Benzyl-1'-(4-phenoxyphenyl)-4,4'-bipyridinium bis-hexafluorophosphate
(1-32) 1-Benzyl-1'-(4-fluorophenyl)-4,4'-bipyridinium dichloride
(1-33) 1-Benzyl-1'-(4-methylphenyl)-4,4'-bipyridinium dichloride
(1-34) 1-Benzyl-1'-(2,4,6-trimethylphenyl)-4,4'-bipyridinium dichloride
(1-35) 1-Benzyl-1'-(benzyl)-4,4'-bipyridinium dichloride
(1-36) 1-Benzyl-1'-(naphthyl)-4,4'-bipyridinium dichloride
(1-37) 1-Benzyl-1'-(phenyl)-4,4'-bipyridinium dichloride
(1-38) 1-Benzyl-1'-(4-cyanophenyl)-4,4'-bipyridinium dichloride
(1-39) 1-Benzyl-1'-(4-benzophenone)-4,4'-bipyridinium dichloride
(1-41) 1-Benzyl-1'-(2,6-dimethylphenyl)-4,4'-bipyridinium dichloride
(1-42) 1-Benzyl-1'-(3,5-dimethylphenyl)-4,4'-bipyridinium dichloride
(1-43) 1-Benzyl-1'-(2,4,6-trimethylphenyl)-4,4'-bipyridinium trifluoromethanesulfonimide Next, a viologen compound represented by Formula (2) preferably used in the present invention will now be described.

The viologen compound represented by Formula (2) has a phosphono group in the molecular structure and can be supported and fixed on the surface of transparent conductive inorganic fine particles to be described later, whereby an electron-injectable constituent layer having no memory capability in a non-observation side electrode can be provided.

In Formula (2), $R^3$ represents $-(CH_2)_m-$ wherein m represents an integer of 0 to 10; an arylene group or a heteroarylene group each having 14 or less carbon atoms, a branched alkylene group or an alkenylene group each having 10 or less carbon atoms or a cycloalkylene group; each of the arylene group, heteroarylene group, branched alkylene group, branched alkenylene group or cycloalkylene group may have a $-P(O)(OH)_2$ group through a $-(CH_2)_n-$ group or may be arbitrarily substituted, wherein n represents an integer of 0 to 10.

$R^4$ represents a group represented by $R^5R^6$, wherein $R^5$ represents $-(CH_2)_p-$ wherein p represents an integer of 0 to 10, and $R^6$ represents $-P(O)(OH)_2$ group or an aryl group or a heteroaryl group each having 14 or less carbon atoms, and an alkyl group or an alkenyl group each having 10 or less carbon atoms or a cycloalkyl group or a hydrogen atom.

$X_2^-$ represents an ion which neutralize the charge.

Further, the above arylene group or heteroarylene group each having not more than 14 carbon atoms; branched alkylene group, branched alkenylene group, aralkylene group and the cycloalkylene group each having not more than 10 carbon atoms, which are each represented by $R^1$, may be arbitrarily substituted, or may be substituted by one substituent or two or more substituents, and, when they are substituted by two or more substituents, the substituents may be the same or different from each other.

Examples of the substituent include:

a lower alkyl group, a lower alkenyl group, a phenyl-substituted lower alkyl group, a diphenyl-substituted lower alkyl group, a phenyl group, a phenoxy group, a lower alkanoyloxy group, a halogen atom, an amino group, a cyano group, a nitro group, a lower alkylamino group, a di-(lower alkyl)amino group, a phenylamino group, a lower alkanolamino group, a benzoylamino group, a lower alkylsulfonylamino group, a phenylsulfonylamino group, a lower alkanoyl group, a benzoyl group, a carboxyl group, a lower alkoxycarbonyl group, a carbamoyl group, an N-lower alkylcarbamoyl group, an N,N-di-(lower alkyl)carbamoyl group, an ureido group, an N-lower alkylureido group, a lower alkylsulfonyl group, a phenylsulfonyl group, a hydroxyl group, a lower alkoxy group, an amino group, a lower alkylamino group, a di-(lower alkyl)amino group, a halogen atom, a carboxyl group, or a lower alkoxy group substituted with a lower alkoxycarbonyl group, an alkoxy group having 3-7 carbon atoms, and a divalent methylenedioxy group.

The phenyl group contained in such as the above phenyl group, benzoyl group, and a phenylamino group may be substituted with, for example, a lower alkyl group, a lower alkoxy group, a hydroxy group, a halogen atom and/or a nitro group.

Moreover, for example, the aryl group, heteroaryl group, branched alkyl group, alkenyl group or cycloalkyl group represented by $R^4$ may be non-substituted, however, may be substituted with one or more groups defined as substituents of above $R^1$.

In abovementioned Formula (2), a preferable compound is: $R^3$ is $-(CH_2)_m$ (wherein m is 1, 2 or 3), a phenyl group (through $-(CH_2)_n-$ group and p-position is substituted with $-P(O)(OH)_2$, wherein n is 1 or 2)); and, in $R^4$ (represented by $R^5R^6$), $R^5$ represents $-(CH_2)_p-$ (wherein p is 0, 1, 2, or 3), $R^6$ is non-substituted phenyl or naphthyl, an alkyl group having 1-4 carbon atoms, a halogen atom, a cyano group, a nitro group, a phenoxy group, or a phenyl or naphthyl group mono-, di- or tri-substituted with a benzoyl group.

Further, $X_2^-$ is $Cl^-$, $Br^-$, $ClO_4^-$, $PF_6^-$, $BF_4^-$, $C_2F_6NO_4S_2^-$ or $CF_3SO_3^-$ and is specifically preferably $Cl^-$ and $PF_6^-$.

In abovementioned Formula (2), a preferable compound is: $R^3$ is $-(CH_2)_m$ (wherein m is 1, 2 or 3), a phenyl group (through $-(CH_2)_n-$ group and p-position is substituted with $-P(O)(OH)_2$, wherein n is 1 or 2)); in $R^4$ (represented by $R^5R^6$), $R^5$ represents $-(CH_2)_p-$ (wherein p is 0, 1, 2, or 3), $R^6$ is $-P(O)(OH)_2$ group, and $X_2^-$ is $Cl^-$, $Br^-$, $ClO_4^-$, $PF_6^-$, $BF_4^-$, $C_2F_6NO_4S_2^-$ or $CF_3SO_3^-$ and is specifically preferably $Cl^-$ and $PF_6^-$.

Among the above compounds, preferable examples include:

(2-1) 1-phosphonoethyl-1'-methyl-4,4'-bipyridinium dibromide
(2-2) 1-phosphonoethyl-1'-(3-propylphenyl)-4,4'-bipyridinium bis-hexafluorophosphate
(2-3) 1-phosphonoethyl-1'-(2,4,6-trimethylphenyl)-4,4'-bipyridinium dichloride
(2-4) 1-phosphonoethyl-1'-(2,4,6-trimethylphenyl)-4,4'-bipyridinium bis-hexafluorophosphate
(2-5) 1-phosphonoethyl-1'-(naphthyl)-4,4'-bipyridinium dichloride
(2-6) 1-phosphonoethyl-1'-(4-cyanonaphthyl)-4,4'-bipyridinium dichloride
(2-7) 1-phosphonoethyl-1'-(4-methylphenyl)-4,4'-bipyridinium dichloride
(2-8) 1-phosphonoethyl-1'-(4-cyanophenyl)-4,4'-bipyridinium dichloride
(2-9) 1-phosphonoethyl-1'-(4-fluorophenyl)-4,4'-bipyridinium dichloride
(2-10) 1-phosphonoethyl-1'-(4-phenoxyphenyl)-4,4'-bipyridinium dichloride
(2-11) 1-phosphonoethyl-1'-(4-t-butylphenyl)-4,4'-bipyridinium dichloride
(2-12) 1-phosphonoethyl-1'-(2,6-dimethylphenyl)-4,4'-bipyridinium dichloride
(2-13) 1-phosphonoethyl-1'-(3,5-dimethyl phenyl)-4,4'-bipyridinium dichloride
(2-14) 1-phosphonoethyl-1'-(4-benzophenone)-4,4'-bipyridinium dichloride
(2-15) 1-phosphonobenzyl-1'-(3-propyl phenyl)-4,4'-bipyridinium dichloride
(2-16) 1-phosphonobenzyl-1'-(3-propyl phenyl)-4,4'-bipyridinium bis-hexafluorophosphate
(2-17) 1-phosphonobenzyl-1'-(phosphonoethyl)-4,4'-bipyridinium dichloride
(2-18) 1-phosphonobenzyl-1'-(2,4-dinitrophenyl)-4,4'-bipyridinium dichloride
(2-19) 1-phosphonobenzyl-1'-(2,4-dinitrophenyl)-4,4'-bipyridinium bis-hexafluorophosphate
(2-20) 1-phosphonobenzyl-1'-(4-phenoxyphenyl)-4,4'-bipyridinium dichloride
(2-21) 1-phosphonobenzyl-1'-(4-phenoxyphenyl)-4,4'-bipyridinium bis-hexafluorophosphate
(2-22) 1-phosphonobenzyl-1'-(4-fluoro phenyl)-4,4'-bipyridinium dichloride
(2-23) 1-phosphonobenzyl-1'-(4-methylphenyl)-4,4'-bipyridinium dichloride
(2-24) 1-phosphonobenzyl-1'-(2,4,6-trimethylphenyl)-4,4'-bipyridinium dichloride
(2-25) 1-phosphonobenzyl-1'-(benzyl)-4,4'-bipyridinium dichloride
(2-26) 1-phosphonobenzyl-1'-(naphthyl)-4,4'-bipyridinium dichloride
(2-27) 1-phosphonobenzyl-1'-(phenyl)-4,4'-bipyridinium dichloride
(2-28) 1-phosphonobenzyl-1'-(4-cyanophenyl)-4,4'-bipyridinium dichloride
(2-29) 1-phosphonobenzyl-1'-(4-benzophenone)-4,4'-bipyridinium dichloride
(2-30) 1-phosphonobenzyl-1'-(4-cyanophenyl)-4,4'-bipyridinium dichloride
(2-31) 1-phosphonobenzyl-1'-(2,6-dimethyl phenyl)-4,4'-bipyridinium dichloride
(2-32) 1-phosphonobenzyl-1'-(3,5-dimethylphenyl)-4,4'-bipyridinium dichloride
(2-33) 1-phosphonobenzyl-1'-(2,4,6-trimethylphenyl)-4,4'-bipyridinium trifluoromethanesulfonimide The manufacturing methods of these compounds are disclosed in abovementioned WO 2004/067673.

[Compounds Represented by Formula (I)-Formula (VI)]

Electrochromic compounds represented by Formula (I)-Formula (VI) according to the present invention described above will now be described.

In Formula (I)-Formula (VI), $R^1$ and $R^2$ each represent a hydrogen atom or a substituent; $R^3$ and $R^4$ each represent a hydrogen atom or a substituent; X represents an oxygen atom or a sulfur atom; m and p each represent an integer of 0-4; and $A^-$ represents an ion to balance charge.

$R^1$-$R^4$ each represent a hydrogen atom or a substituent. Specific examples of the substituent represented by $R^1$-$R^4$ includes, for example, an alkyl group (e.g., a methyl group, ethyl group, propyl group, isopropyl group, tert-butyl group, pentyl group, or hexyl group), a cycloalkyl group (e.g., a cyclohexyl group or cyclopentyl group), an alkenyl group, a cycloalkenyl group, an alkynyl group (e.g., a propargyl group), a glycidyl group, an acrylate group, a methacrylate group, an aromatic group (e.g., a phenyl group, naphthyl group, or anthracenyl group), a heterocyclic group (e.g., a pyridyl group, thiazolyl group, oxazolyl group, imidazolyl group, furyl group, pyrrolyl group, pyrazinyl group, pyrimidinyl group, pyridazinyl group, selenazolyl group, suliforanyl group, piperidinyl group, pyrazolyl group, or tetrazolyl group), an alkoxy group (e.g., a methoxy group, ethoxy group, propyloxy group, pentyloxy group, cyclopentyloxy group, hexyloxy group, or cyclohexyloxy group), an aryloxy group (e.g., a phenoxy group), an alkoxycarbonyl group (e.g., a methyloxycarbonyl group, ethyloxycarbonyl group, or butyloxycarbonyl group), an aryloxycarbonyl group (e.g., a phenyloxycarbonyl group), a sulfonamide group (e.g., a methanesulfonamide group, ethanesulfonamide group, butanesulfonamide group, hexanesulfonamide group, cyclohexanesulfonamide group, or benzenesulfonamide group), a sulfamoyl group (e.g., an aminosulfonyl group, methylaminosulfonyl group, dimethylaminosulfonyl group, butylaminosulfonyl group, hexylaminosulfonyl group, cyclohexylaminosulfonyl group, phenylaminosulfonyl group, or 2-pyridylaminosulfonyl group), a urethane group (e.g., a methylureido group, ethylureido group, pentylureido group, cyclohexylureido group, phenylureido group, or 2-pyridylureido group), an acyl group (e.g., an acetyl group, propionyl group, butanoyl group, hexanoyl group, cyclohexanoyl group, benzoyl group, or pyridinoyl group), a carbamoyl group (e.g., an aminocarbonyl group, methylaminocarbonyl group, dimethylaminocarbonyl group, propylaminocarbonyl group, pentylaminocarbonyl group, cyclohexylaminocarbonyl group, phenylaminocarbonyl group, or 2-pyridylaminocarbonyl group), an acylamino group (e.g., an acetylamino group, benzoylamino group, or methylureido group), an amide group (e.g., an acetamide group, propionamide group, butanamide group, hexanamide group, or benzamide group), a sulfonyl group (e.g., a methylsulfonyl group, ethylsulfonyl group, butylsulfonyl group, cyclohexylsulfonyl group, phenylsulfonyl group, or 2-pyridylsulfonyl group), a sulfonamide group (e.g., a methylsulfonamide group, octylsulfonamide group, phenylsulfonamide group, or naphthylsulfonamide group), an amino group (e.g., an amino group, ethylamino group, dimethylamino group, butylamino group, cyclopentylamino group, anilino group, or 2-pyridylamino group), a halogen atom (e.g., a chlorine atom, bromine atom, or iodine atom), a cyano group, a nitro group, a sulfo group, a carboxyl group, a hydroxyl group, a phosphono group (e.g., a phosphonoethyl group, phosphonopropyl group, or phosphonooxyethyl group), and an oxamoyl group. These groups may be further substituted with any thereof.

Further, as the substituent represented by $R^1$, the following substituents are preferable.

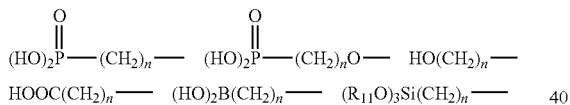

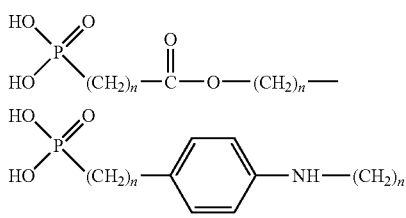

wherein $R_{11}$ represents an alkyl group of a carbon number of 1-10 and n represents an integer of 1-10.

Further, m and p each represent an integer of 0-4, and when m or p represents at least 2, adjacent $R_3$ and $R_4$ each represent —CH═CH—CH═CH— of a valence of 2.

X represents an oxygen atom or a sulfur atom.

As an ion represented by $A^-$ to balance charge, for example, a halogen ion, $BF_4^-$, $PH_6^-$, $ClO_4^-$, $CH_3SO_4^-$, and $C_2H_5SO_4^-$ can be listed.

Specific compound examples of the electrochromic compounds represented by Formula (I)-Formula (VI) will now be listed, but the present invention is not limited by these exemplified compounds only.

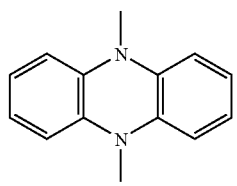

(1)

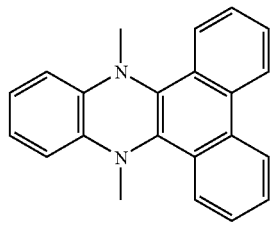

(2)

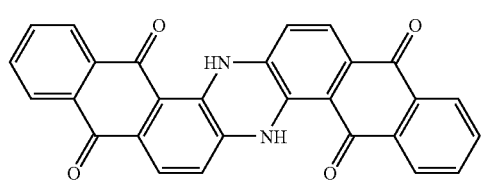

(3)

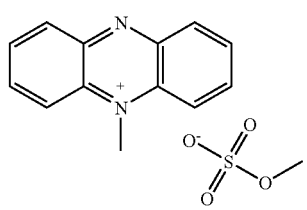

(4)

(5)

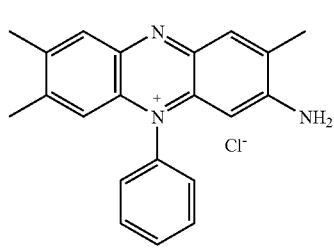

(6)

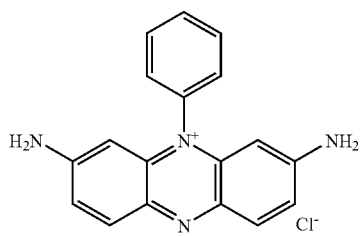

(7)

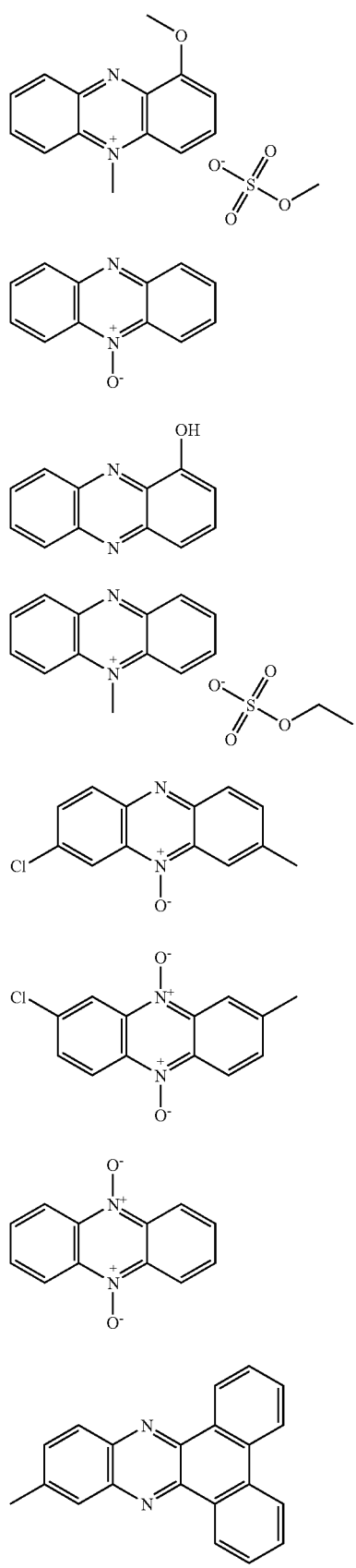
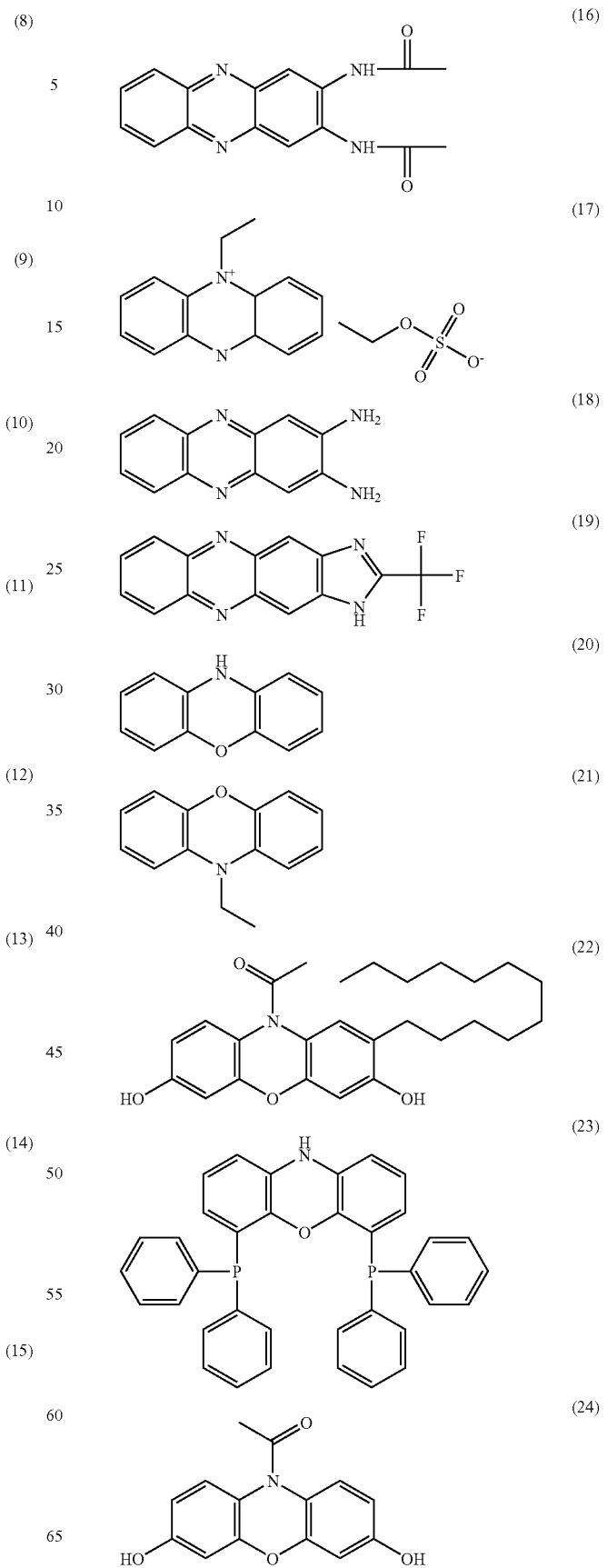

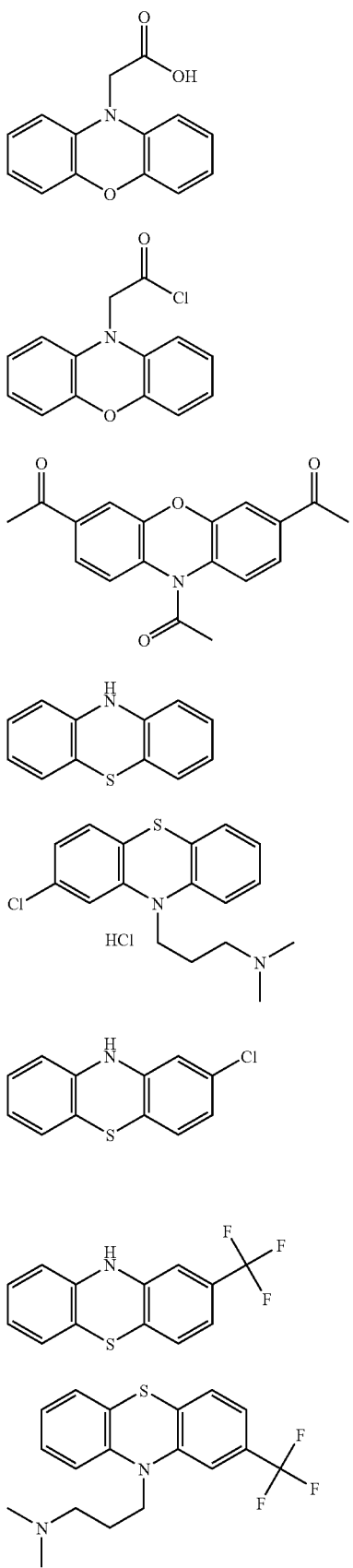
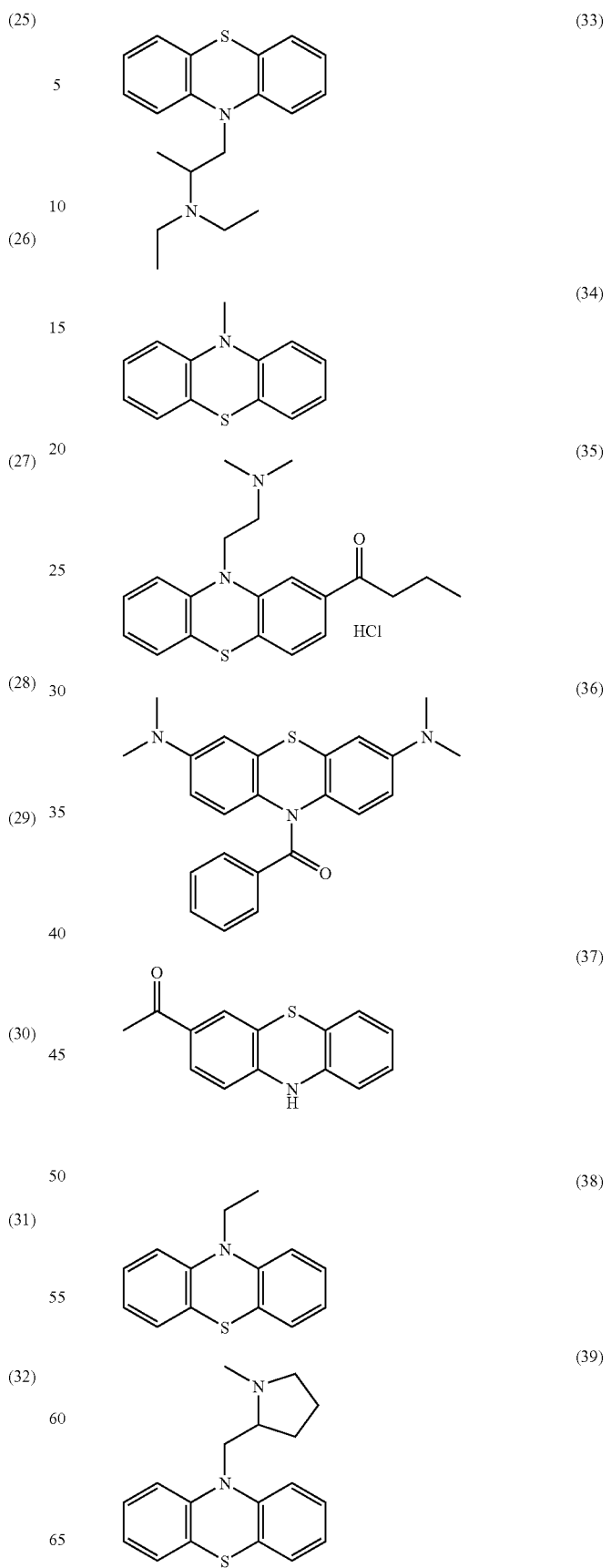

-continued

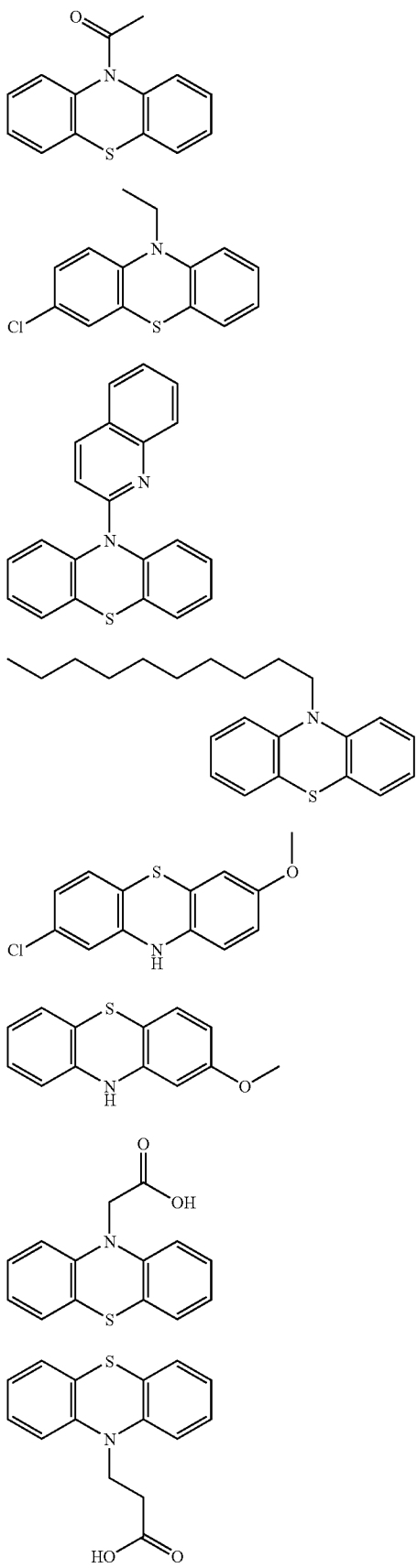

(40)
(41)
(42)
(43)
(44)
(45)
(46)
(47)

-continued

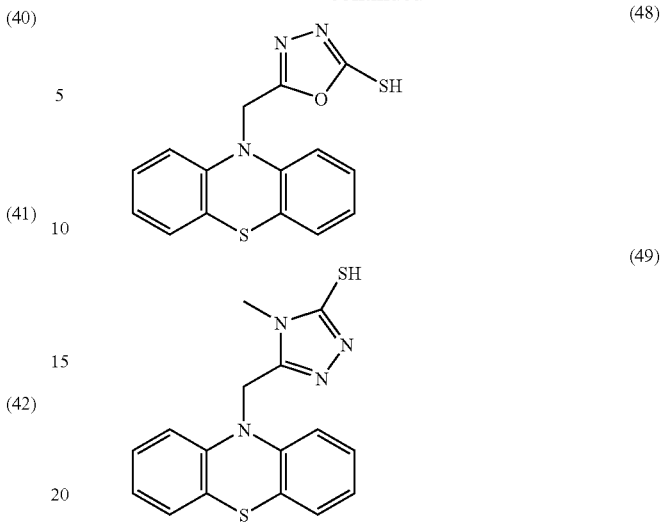

(48)
(49)

Any of the electrochromic compounds represented by Formula (I)-Formula (VI) of the present invention can be synthesized by conventionally known methods. Methods described in the following references are exemplified: Topics in Current Chemistry, Vol. 92, pp 1-44 (1980); Angrew. Chem., 90, 927 (1978); Adv. Mater., 3, 225 (1991); German Offenlegungsschrift, 3 917 323, J. Am. Chem. Soc., 117, 8528 (1995); J. C. S. Perkin II 1990, 1777; German Offenlegungsschrift, 4 435 211; EP-A 476 456; EP-A 476 457; German Offenlegungsschrift, 4 007 058; J. Org. Chem., 57, 1849 (1992); and J. Am. Chem. Soc., 99, 6120 and 6122 (1977).

[Compounds Represented by Formula [1]-Formula [8]]

Next, electrochromic compounds represented by Formula [1]-Formula [8] according to the present invention will now be described.

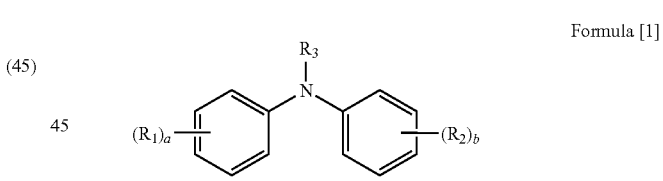

Formula [1]

In Formula [1], $R_1$ and $R_2$ each represent a substituent. Examples of the substituent include a halogen atom (e.g., a fluorine atom, chlorine atom, bromine atom, or iodine atom), an alkyl group (e.g., a methyl group, ethyl group, propyl group, isopropyl group, tert-butyl group, pentyl group, hexyl group, octyl group, dodecyl group, tridecyl group, tetradecyl group, pentadecyl group, chloromethyl group, trifluoromethyl group, trichloromethyl group, tribromomethyl group, pentafluoroethyl group, or methoxyethyl group), a cycloalkyl group (e.g., a cyclopentyl group or cyclohexyl group), an alkenyl group (e.g., a vinyl group or allyl group), an alkynyl group (e.g., an ethynyl group or propargyl group), an aryl group (e.g., a phenyl group, naphthyl group, p-nitrophenyl group, p-fluorophenyl group, or p-methoxyphenyl group), a heterocyclic group (e.g., a furyl group, thienyl group, pyridyl group, pyridazyl group, pyrimidyl group, pyrazyl group, triazyl group, imidazolyl group, pyrazolyl group, thiazolyl group, benzimidazolyl group, benzoxazolyl group, quinazolyl group, phthalazyl group, pyrrolidyl group, imidazolidyl group, morpholyl group, or oxazolidyl group), an alkoxy group (e.g., a methoxy group, ethoxy group, propoxy group, isopropoxy group, butoxy group, tert-butoxy group, or sec-butoxy group), an alkoxycarbonyl group (e.g., a methyloxycarbonyl group, ethyloxycarbonyl group, butyloxycarbonyl group, octyloxycarbonyl group, or dodecyloxycarbonyl group), an aryloxycarbonyl group (e.g., a phenyloxycarbonyl group or naphthyloxycarbonyl group), a sulfamoyl group (e.g., an aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group, or 2-pyridylaminosulfonyl group), an acyl group (e.g., an acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group, or pyridylcarbonyl group), a carbamoyl group (e.g., an aminocarbonyl group, methylaminocarbonyl group, dimethylaminocarbonyl group, propylaminocarbonyl group, pentylaminocarbonyl group, cyclohexylaminocarbonyl group, octylaminocarbonyl group, 2-ethylhexylaminocarbonyl group, dodecylaminocarbonyl group, phenylaminocarbonyl group, naphthylaminocarbonyl group, or 2-pyridylaminocarbonyl group), a sulfinyl group (e.g., a methylsulfinyl group, ethylsulfinyl group, butylsulfinyl group, cyclohexylsulfinyl group, 2-ethylhexylsulfinyl group, dodecylsulfinyl group, phenylsulfinyl group, naphthylsulfinyl group, or 2-pyridylsulfinyl group), an alkylsulfonyl group (e.g., a methylsulfonyl group, ethylsulfonyl group, butylsulfonyl group, cyclohexylsulfonyl group, 2-ethylhexylsulfonyl group, or dodecylsulfonyl group), an arylsulfonyl group (e.g., a phenylsulfonyl group, naphthyl sulfonyl group, or 2-pyridylsulfonyl group), a cyano group, an amino group (e.g., an amino group, methylamino group, dimethylamino group, ethylamino group, diethylamino group, butylamino group, or dibutylamino group), an acylamino group (e.g., an acetamide group, propionamide group, isopropionamide group, butanamide group, or pivaloylamide group). Of these, an alkyl group, an alkylene group, an alkoxy group, and an amino group are preferable.

$R_3$ represents a hydrogen atom, aryl group, or heterocyclic group, being preferably a hydrogen atom or aryl group. When $R_3$ represents a hydrogen atom, either $R_1$ or $R_2$ represents an amino group.

The symbols a and b each independently represent an integer of 0-4. When a and b are at least 2, at least 2 $R_1$'s or at least 2 $R_2$'s each may be the same or differ. Adjacent $R_1$'s or $R_2$'s each may join to form a ring.

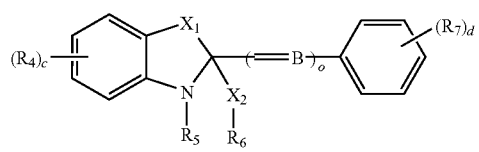

Formula [2]

In Formula [2], $R_4$ and $R_7$ each represent a substituent. Examples of the substituent include those similar to the examples listed as $R_1$ and $R_2$ in above Formula [1]. $R_4$ preferably represents a halogen atom, an alkyl group, an alkoxy group, an amino group, or an alkylsulfonyl group. $R_7$ preferably represents a halogen atom, an alkyl group, an alkoxy group, or an amino group.

$R_5$ and $R_6$ each represent an alkyl group. $R_5$ and $R_6$ each may join to form a ring, preferably to form a 5-membered ring. Further, the o-position of the phenyl group joining B and $X_2$ may directly join to form a ring, preferably to form a 5-membered ring.

$X_1$ represents —$CR_{34}R_{35}$—, —$NR_{36}$—, —O—, or —S—, preferably —$CR_{34}R_{35}$—. $R_{34}$, $R_{35}$, and $R_{36}$ each represent an alkyl group.

B represents =CH— or =N—, being preferably =CH—.

The symbol c represents an integer of 0-4. When c represents at least 2, at least 2 $R_4$'s each may be the same or differ, and further adjacent $R_4$'s may join to form a ring.

The symbol d represents an integer of 0-5. When d represents at least 2, at least 2 $R_7$'s each may be the same or differ, and further adjacent $R_7$'s may join to form a ring.

The symbol o represents an integer of 1 or 2, being preferably 1.

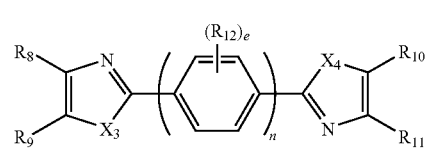

Formula [3]

In Formula [3], $R_8$-$R_{11}$ each represent a hydrogen atom or a substituent. Examples of the substituent include those similar to the examples listed as $R_1$ and $R_2$ in Formula [1]. $R_8$-$R_{11}$ preferably represent a hydrogen atom, an alkyl group, an aryl group, or a heterocyclic group. $R_{12}$ represents a substituent. Examples of the substituent include those similar to the examples listed as $R_1$ and $R_2$ in Formula [1]. $R_{12}$ preferably represents a halogen atom, an alkyl group, or an alkoxy group.

The symbol e represents an integer of 0-4. When e represents at least 2, at least 2 $R_{12}$'s each may be the same or differ, and further adjacent $R_{12}$'s may join to form a ring.

$X_2$ and $X_3$ represent —$CR_{34}R_{35}$—, —$NR_{36}$—, —O—, or —S—, being preferably —$NR_{36}$—, or —O—. Further, $X_2$ and $X_3$ may be the same or differ, being preferably the same. The symbol n represents 0 or 1.

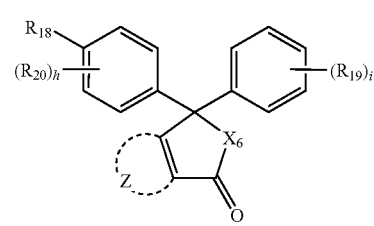

Formula [4]

In Formula [4], $R_{18}$ represents a hydroxyl group, an alkoxy group, or an amino group, being preferably an amino group. $R_{19}$ and $R_{20}$ each represent a substituent. Examples of the substituent include those similar to the examples listed as $R_1$ and $R_2$ in Formula [1], preferably including a halogen atom, an alkyl group, an alkoxy group, and an amino group. In the phenyl groups substituted with $R_{19}$ and $R_{20}$, a 5-membered ring may be formed via direct bonding to the next position of a carbon atom joining a quaternary carbon. Further, in each of the phenyl groups substituted with $R_{19}$ and $R_{20}$, when the next position of a carbon atom joining a quaternary carbon is substituted with each of $R_{19}$ and $R_{20}$, $R_{19}$ and $R_{20}$ may join to form a ring, preferably to form a 6-membered ring via an oxygen atom.

The symbol h represents an integer of 0-3. When h represents at least 2, at least 2 $R_{20}$'s each may be the same or differ, and further adjacent $R_{20}$'s may join to form a ring.

The symbol i represents an integer of 0-4. When i represents at least 2, at least 2 $R_{19}$'s each may be the same or differ, and further adjacent $R_{19}$'s may join to form a ring.

$X_5$ represents —O— or —$NR_{36}$—, being preferably —O—. Z represents a residual group needed to form an aromatic or heterocyclic ring.

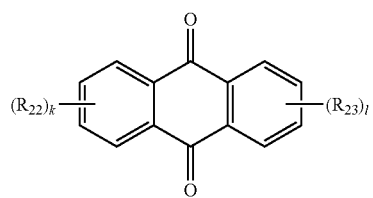

Formula [5]

In Formula [5], $R_{22}$ and $R_{23}$ each represent a substituent. Examples of the substituent include those similar to the examples listed as $R_1$ and $R_2$ in Formula [1], preferably including a halogen atom, an alkyl group, an alkoxy group, a hydroxycarbonyl group, and an alkoxycarbonyl group, more preferably an alkyl group and a hydroxycarbonyl group.

The symbols k and l each independently represent an integer of 0-4. When k and l represent at least 2, at least 2 $R_{22}$'s or at least 2 $R_{23}$'s may be the same or differ, and further adjacent $R_{22}$'s or $R_{23}$'s may join to form a ring.

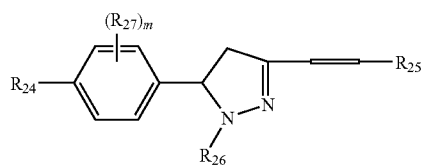

Formula [6]

In Formula [6], $R_{24}$ represents a hydroxyl group, an alkoxy group, or an amino group, being preferably an amino group.

$R_{25}$ represents an aryl group or a heterocyclic group, being preferably an aryl group.

$R_{26}$ represents a hydrogen atom, an alkyl group, an aryl group, a heterocyclic group, an acyl group, or a carbamoyl group, being preferably an aryl group.

$R_{27}$ represents a substituent. Examples of the substituent include those similar to the examples listed as $R_1$ and $R_2$ in Formula [1], preferably including a halogen atom, an alkyl group, and an alkoxy group, more preferably an alkyl group.

The symbol m represents an integer of 0-4. When m represents at least 2, at least 2 $R_{27}$'s each may be the same or differ, and further adjacent $R_{27}$'s may join to form a ring.

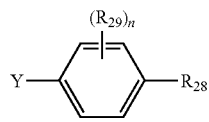

Formula [7]

In Formula [7], $R_{28}$ and $R_{29}$ each represent a substituent. Examples of the substituent include those similar to the examples listed as $R_1$ and $R_2$ in Formula [1]. $R_{29}$ preferably includes a halogen atom, an alkyl group, an aryl group, a heterocyclic group, an alkoxycarbonyl group, an acyl group, an alkylsulfonyl group, and a cyano group, more preferably an aryl group, an alkoxycarbonyl group, an acyl group, and a cyano group. $R_{29}$ preferably includes a halogen atom, an alkyl group, and alkoxy group, more preferably an alkyl group.

The symbol n represents an integer of 0-4. When n represents at least 2, at least 2 $R_{29}$'s each may be the same or differ, and further adjacent $R_{29}$'s may join to form a ring.

Y represents an electron-attracting group. The electron-attracting group refers to a substituent able to have a positive Hammett substituent constant σp. The Hammett substituent constant is defined as σ in the following Hammett equation satisfied when in a meta- or para-substituted compound of an aromatic compound, the reaction rate constants of the unsubstituted compound and the substituted compound are designated as k0 and k, respectively.

Log(k/k0)=ρσ wherein in the above Hammett equation, ρ=1 for dissociation reaction of benzoic acid and a derivative thereof performed in an aqueous solution of 25° C.

Journal of Medicinal Chemistry, 1973, Vol. 16, No. 11, 1207-1216 can be referred to for the Hammett substituent constant.

Examples of the electron-attracting group include a substituted alkyl group (e.g., a halogen-substituted alkyl), a substituted alkenyl group (e.g., cyanovinyl), a substituted or unsubstituted alkynyl group (e.g., trifluoromethylacetylenyl or cyanoacetylenyl), a substituted aryl group (e.g., cyanophenyl), a substituted or unsubstituted heterocyclic group (e.g., pyridyl, triazinyl, or benzoxazolyl), a halogen atom, a cyano group, an acyl group (e.g., acetyl, trifluoroacetyl, or formyl), a thioacetyl group (e.g., thioacetyl or thioformyl), an oxalyl group (e.g., methyloxalyl), an oxyoxalyl group (e.g., ethoxalyl), a thiooxalyl group (e.g., ethylthiooxalyl), an oxamoyl group (e.g., methyloxamoyl), an oxycarbonyl group (e.g., ethoxycarbonyl), a carboxyl group, a thiocarbonyl group (e.g., ethylthiocarbonyl), a carbamoyl group, a thiocarbamoyl group, a sulfonyl group, a sulfinyl group, an oxysulfonyl group (e.g., ethoxysulfonyl), a thiosulfonyl group (e.g., ethylthiosulfonyl), a sulfamoyl group, an oxysulfinyl group (e.g., methoxysulfinyl), a thiosulfinyl group (e.g., methylthiosulfinyl), a sulfinamoyl group, a phosphoryl group, a nitro group, an imino group, an N-carbonylimino group (e.g., N-acetylimino), an N-sulfonylimino group (e.g., N-methanesulfonylimino), a dicynoethylene group, an ammonium group, a sulfonium group, a phosphonium group, a pyrilium group, and an immonium group. A cyano group, an acyl group, and an oxycarbonyl group are preferable.

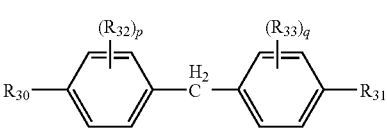

Formula [8]

In Formula [8], $R_{30}$ and $R_{31}$ represent a hydrogen atom, a hydroxyl group, an alkoxy group, or an amino group. $R_{30}$ and $R_{31}$ do not represent a hydrogen atom simultaneously. Either $R_{30}$ or $R_{31}$ preferably represents an amino group, and both $R_{30}$ and $R_{31}$ preferably represent an amino group simultaneously.

$R_{32}$ and $R_{33}$ represent a substituent. Examples of the substituent include those similar to the examples listed as $R_1$ and $R_2$ in Formula [1], preferably including a halogen atom, an alkyl group, an aryl group, and an alkoxy group.

The symbols p and q each independently represent an integer of 0-4. When p and q are at least 2, at least 2 $R_{32}$'s or at least 2 $R_{33}$'s each may be the same or differ. Adjacent $R_{32}$'s or $R_{33}$'s each may join to form a ring.

Of the electrochromic compounds represented by above Formulas [1]-[8], those of Formulas [2], [4], [5], and [7] are preferable.

(Chemical Adsorption and Physical Adsorption)

In the present invention, it is preferable that an electrochromic compound be chemically or physically adsorbed on the surface of at least one of the opposite electrodes. In the present invention, chemical adsorption refers to, of adsorption phenomena of a solid surface, one wherein the cause is a chemical bonding force. Adsorption heat is commonly about 20-100 kcal/mol. In contrast, physical adsorption refers to a phenomenon wherein the cause of the adsorption phenomenon is a van der Waals force and the adsorption is concentrated on the solid surface. Adsorption heat is commonly at most 10 kcal/mol.

In the present invention, the meaning that an EC compound is chemically or physically adsorbed on the surface of an electrode refers to a state wherein the EC compound is adsorbed on the electrode via a chemical bonding force or van der Waals force. Chemical adsorption via ionic bonding force or coordinate bonding force is preferable.

In a preferable configuration of the chemical adsorption via ionic bonding force or coordinate bonding force, the electrochromic compound preferably has at least one adsorption group selected from —$CO_2H$, —$PO(OH)_2$, —$OPO(OH)_2$, —$SO_3H$, and —$Si(OR)_3$ (R represents a hydrogen atom or an alkyl group), more preferably having —$PO(OH)_2$ as the adsorption group.

Specific examples of the electrochromic compounds represented by Formulas [1]-[8] of the present invention will now be listed that by no means limit the scope of the present invention.

1-1
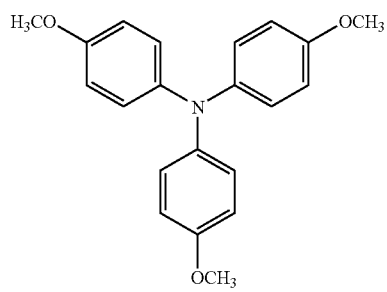

1-2
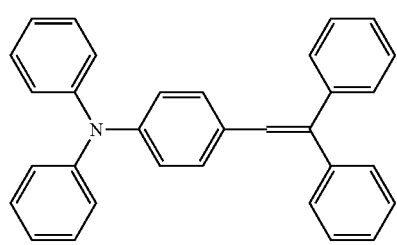

1-3
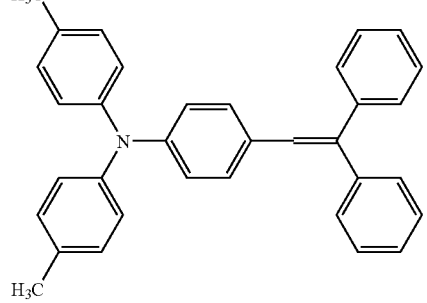

1-4
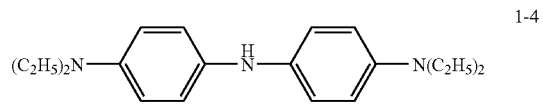

1-5
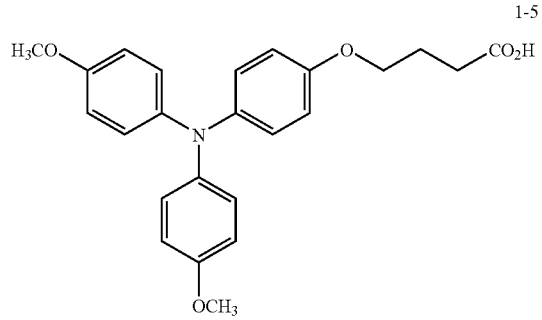

1-6
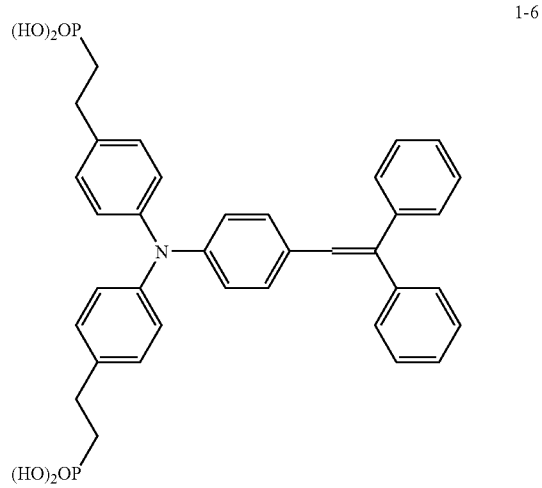

1-7
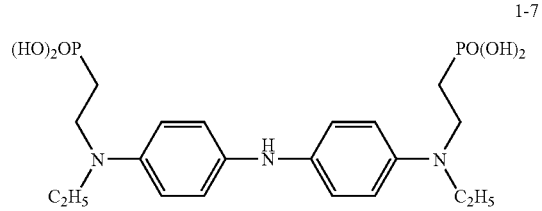

2-1
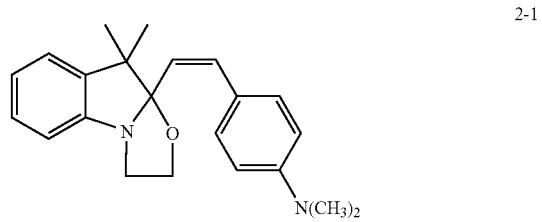

2-2
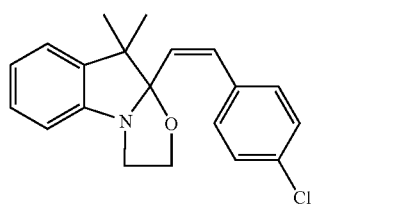
2-3
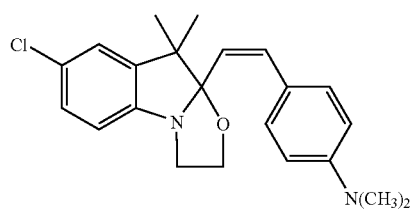
2-4
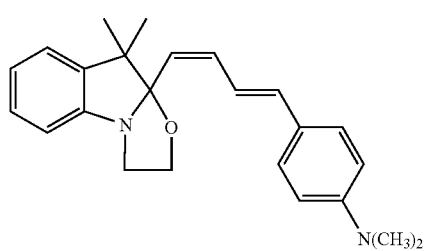
2-5
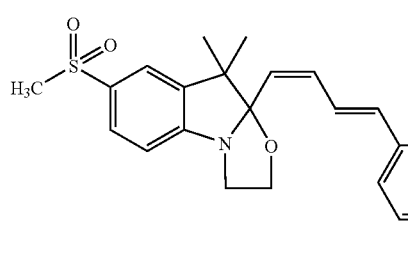
2-6
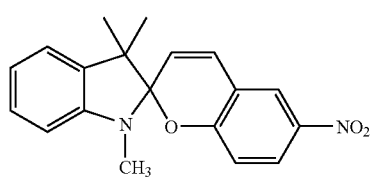
2-7
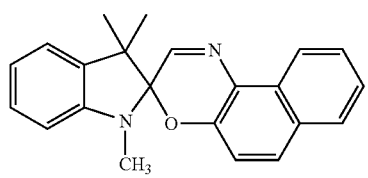
2-8
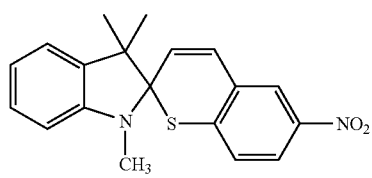
2-9
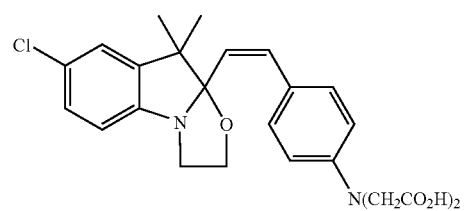
2-10
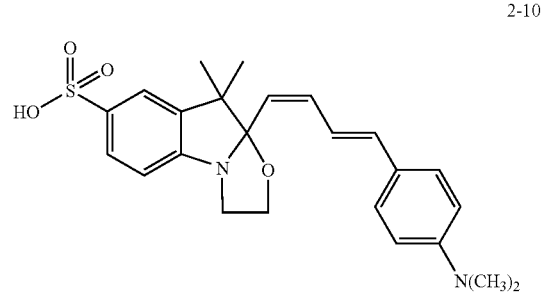
2-11
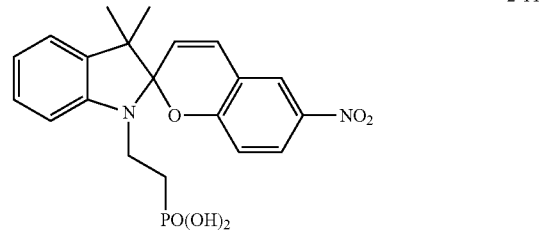
2-12
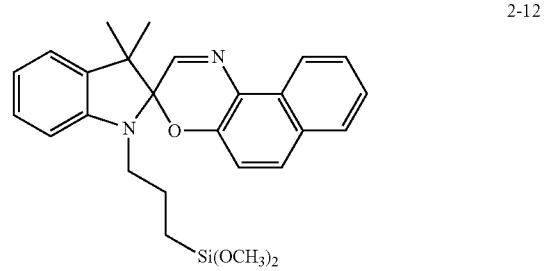
3-1
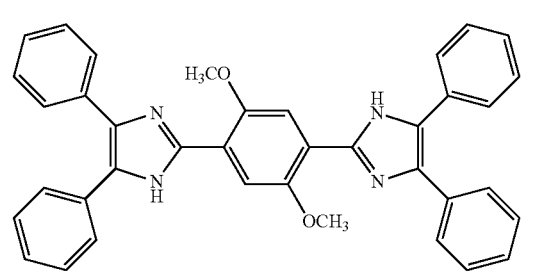
3-2
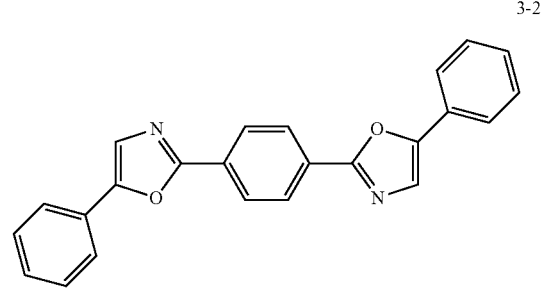

-continued
3-3
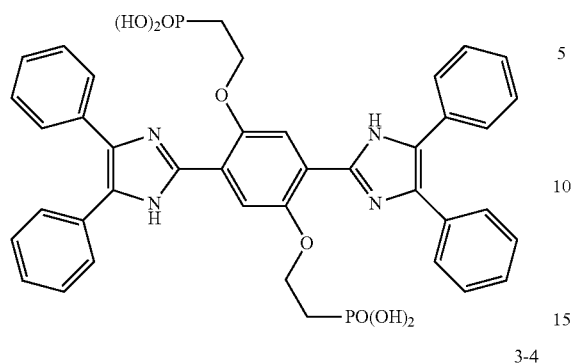
3-4
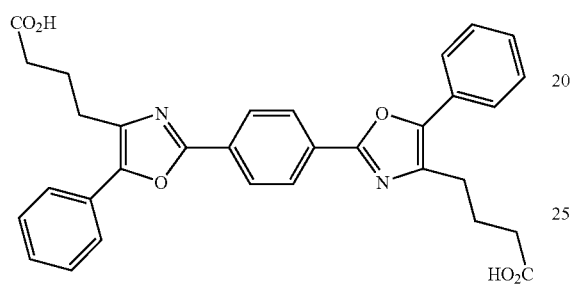
3-5
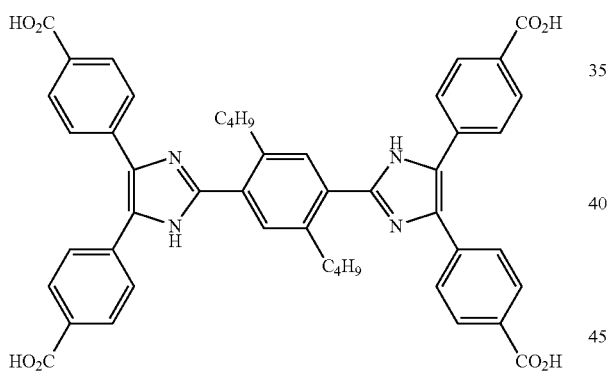
3-6
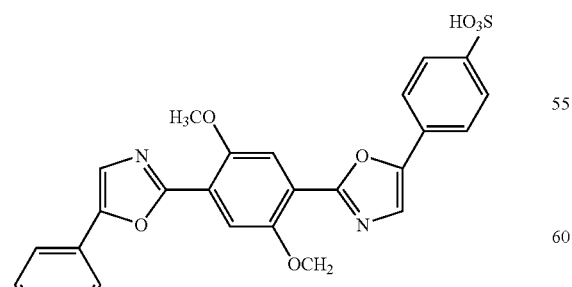
-continued
3-7
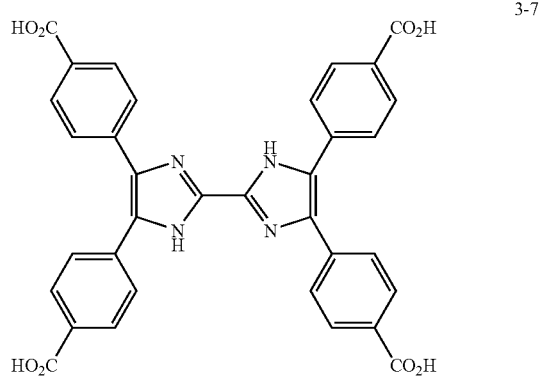
3-8
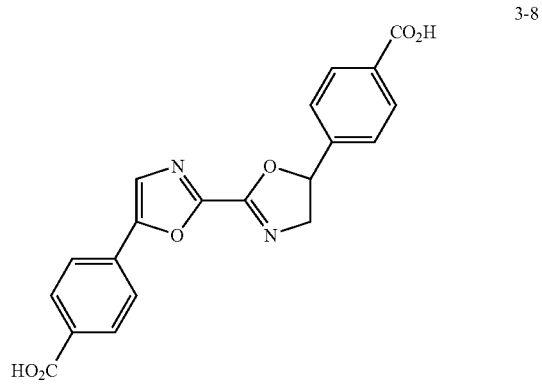
3-9
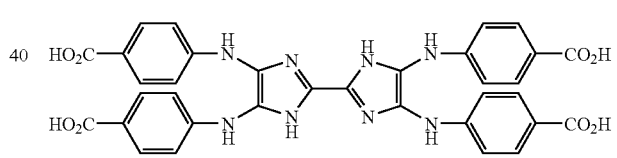
4-1
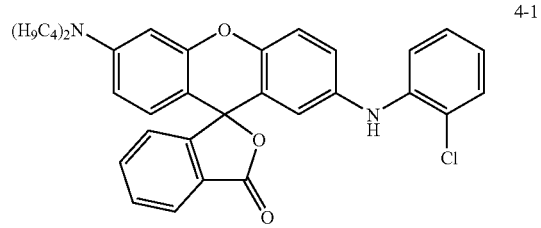
4-2
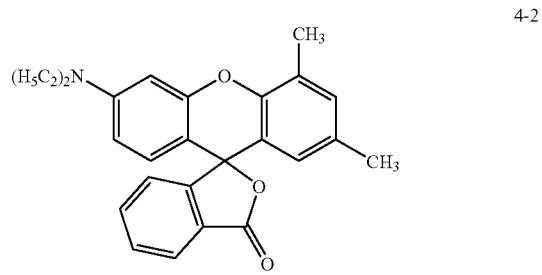

4-3
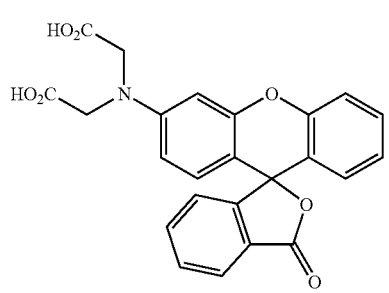
4-4
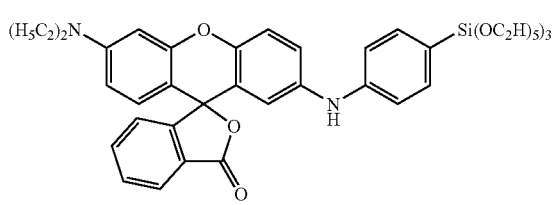
5-1
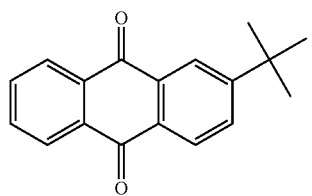
5-2
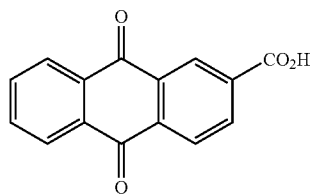
6-1
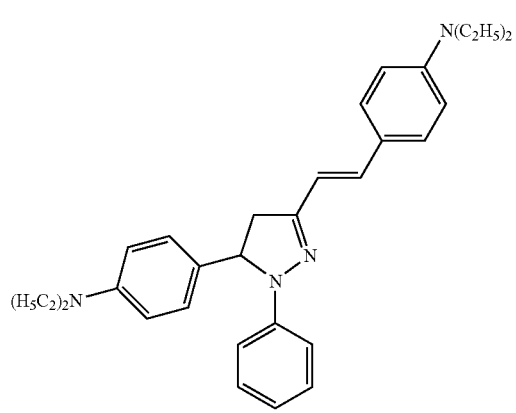
6-2
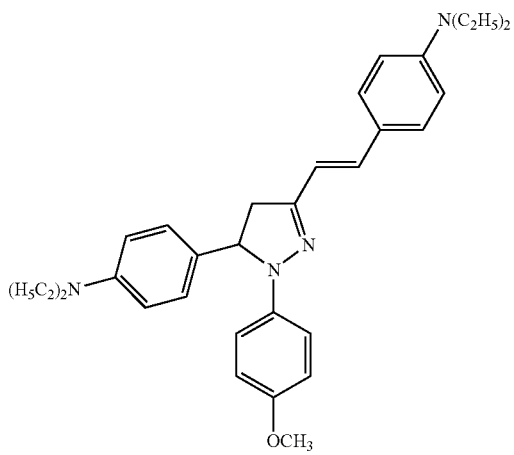
6-3
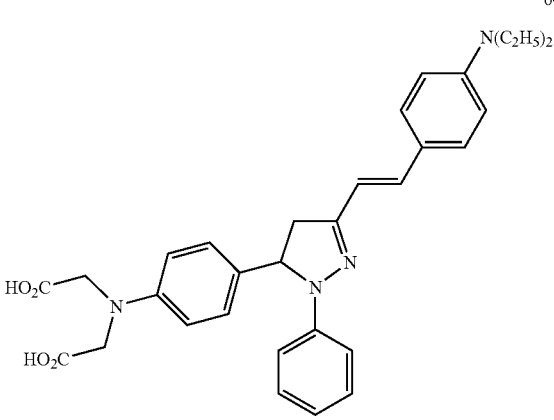
6-4
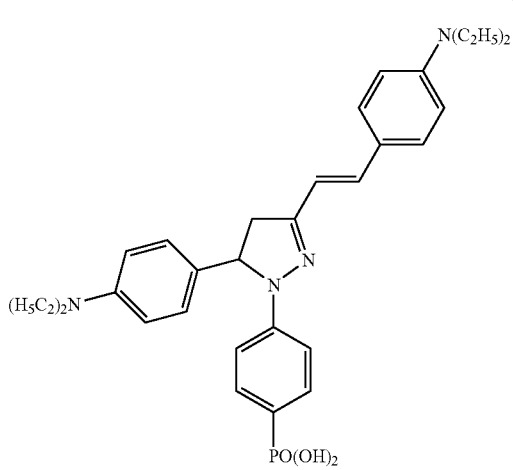
7-1
7-2
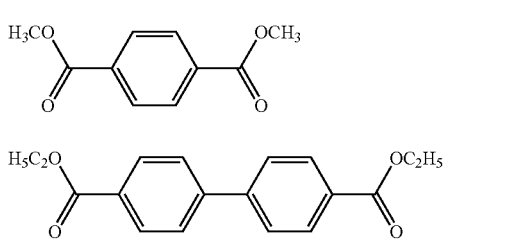

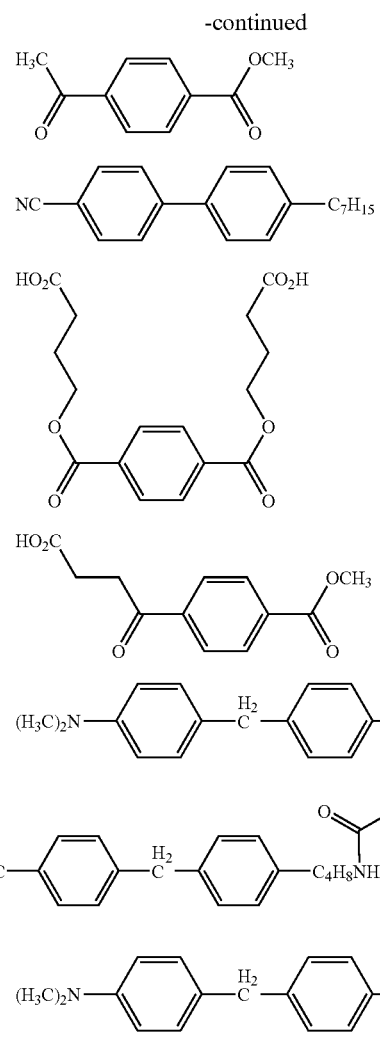

In the display element of the present invention, there are also usable, as appropriate, electrochromic compounds other than those represented by above Formulas, for example, organic or inorganic electrochromic compounds. The inorganic electrochromic compounds include metal oxides such as tungsten oxide, iridium oxide, vanadium oxide, or nickel oxide and complex salts such as Prussian blue, while the organic electrochromic compounds include viologen, imidazole, and rare-earth diphthalocyanine.

An electrochromic compound in the display element of the present invention is characterized by the change from a colorless state to a colored state via redox reaction. The change is preferably generated in the range of −3.5 V-3.5 V, more preferably −1.5 V-1.5 V.

[White Scattering Material]

The display element of the present invention may incorporate a porous white scattering material by forming a porous white scattering layer from the viewpoint of enhancing display contrast and white display reflectance.

The porous white scattering layers which can be applied to the present invention are formed by coating and drying an aqueous mixture of aqueous polymers substantially insoluble in the electrolyte solvents and white pigment.

Examples of white pigments which can be used in the present invention include: titanium dioxide (anatase or rutile type), barium sulfate, calcium carbonate, aluminum oxide, zinc oxide, magnesium oxide, zinc hydroxide, magnesium hydroxide, magnesium phosphate, magnesium hydrogen phosphate, alkaline earth metallic salts, talc, kaolin, zeolite, acid clay, glass, and organic compounds such as polyethylene, polystyrene, acryl resins, ionomers, ethylene-vinyl acetate copolymeric resins, benzoguanamine resins, urea-formaldehyde resins, melamine-formaldehyde resins, or polyamide resins. These substances may be uses individually or in combination, or in the form in which voids, capable of varying the refractive index, are contained in the particles.

In the present invention, titanium dioxide, zinc oxide and zinc hydroxide are preferably employed among the-above described white particles. Further, titanium oxide may be titanium oxide which has been subjected to a surface treatment employing an inorganic oxide (such as $Al_2O_3$, AlO (OH), or $SiO_2$), or titanium oxide which has been subjected to a treatment employing an organic compound such as trimethylolethane, triethanolamine acetic acid salts, or trimethylcyclosilane, in addition to the above surface treatment.

Among these white particles, it is preferable to use titanium oxide or zinc oxide in view of minimization of coloration at high temperature and reflectance of elements due to refractive index.

Listed as an aqueous polymer which is substantially insoluble in electrolyte solvent according to the present invention may be water-soluble polymer and polymer which dispersed in water based solvent.

As water-soluble polymers applicable to the present invention, there can be listed, for example, protein such as gelatin, or gelatin derivatives; cellulose derivatives; natural compounds including polysaccharides such as starch, gum arabic, dextran, pullulan, carrageenan; and synthetic polymers such as polyvinyl alcohol, polyethylene glycol, polyvinyl pyrrolidone, acrylamide polymers, or derivatives thereof. The gelatin derivatives include acetyl gelatin and phthalic gelatin. The polyvinyl alcohol derivatives include terminal alkyl group-modified polyvinyl alcohol and terminal mercapto group-modified polyvinyl alcohol. The cellulose derivatives include hydroxyethyl cellulose, hydroxypropyl cellulose, and carboxymethyl cellulose. In addition, there are also usable those described in Research Disclosure and on pages 71-75 of Unexamined Japanese Patent Application Publication (hereinafter referred to as JP-A) No. 64-13546; highly water-absorbing polymers, described in U.S. Pat. No. 4,960,681 and JP-A No. 62-245260, that is, homopolymers of vinyl monomers containing —COOM or —$SO_3M$ (wherein M is a hydrogen atom or an alkali metal), or copolymers of these monomers or copolymers of the same with other monomers (for example, sodium methacrylate, ammonium methacrylate, or potassium acrylate). These binders may be used in combinations of at least 2 types.

In the present invention, preferably employed may be gelatin and derivatives thereof, or polyvinyl alcohol and derivatives thereof.

Listed as polymers dispersed in water based solvents may be latexes such as natural rubber latex, styrene butadiene rubber, butadiene rubber, nitrile rubber, chloroprene rubber, heat curable resins which are prepared by dispersing, in water based solvents, polyisocyanate based, epoxy based, acryl based, silicone based, polyurethane based, urea based, phenol based, formaldehyde based, epoxy-polyamide based, melamine based, or alkyd based resins, or vinyl based resins. Of these polymers, it is preferable to employ water based polyurethane resins described in JP-A No. 10-76621.

"Being substantially insoluble in electrolyte solvents", as described in the present invention, is defined as a state in which the dissolved amount per kg of the electrolyte solvents is 0-10 g in the temperature range of −20 to 120° C. It is possible to determine the above dissolved amount employing the methods known in the art, such as a weight measuring method, or a component quantitative method utilizing liquid chromatogram and gas chromatogram.

In the present invention, a preferred embodiment of the aqueous mixture of water based compounds and white pigments is dispersed in water with the dispersion methods known in the art. The mixing ratio of water based compounds/titanium oxide is preferably in the range of 1-0.01 in terms of volume ratio, but is more preferably in the range of 0.3-0.05.

In the present invention, a media on which the aqueous mixture of the water based compounds and white pigments is coated may be located anywhere as long as they are located on the structural components between the counter electrodes of the display element. However, it is preferable that they are provided on at least one of the above counter electrodes. Examples of media providing methods include a coating system, a liquid spraying system, a spraying method via a gas phase, such as a system which jets liquid droplets employing vibration of a piezoelectric element such as a piezoelectric system ink-jet head, a BUBBLE JET (registered trade name) ink-jet head which ejects liquid droplets employing a thermal head utilizing bumping, and a spray system in which liquid is sprayed via air or liquid pressure.

An appropriate coating system may be selected from any of the coating systems known in the art, and examples thereof include an air doctor coater, a blade coater, a rod coater, a knife coater, a squeeze coater, an impregnation coater, a reverse roller coater, a transfer roller coater, a curtain coater, a double roller coater, a slide hopper coater, a gravure coater, a kiss roller coater, a bead coater, a spray coater, a calender coater, and an extrusion coater.

Methods to dry the aqueous mixture of water based compounds and white pigments provided on the medium are not particularly limited as long as they facilitate water evaporation. Examples thereof include heating employing a heating source, a heating method employing infrared radiation, and a heating method utilizing electromagnetic induction. Further, water evaporation may be performed under reduced pressure.

The term "porous" referred to in the present invention is of a penetrating state capable of inducing silver dissolution and deposition reaction and enabling ion species to move between electrodes, wherein a porous white scattering substance is formed by coating and drying the dispersion on an electrode, and an electrolyte liquid incorporating silver or a compound containing silver in its chemical structure is applied on the scattering substance, followed by being sandwiched with opposed electrodes to produce a potential difference between the opposed electrodes.

In the display element of the present invention, during coating and drying of the aforesaid water based dispersion or after drying thereof, the above water based dispersion is preferably hardened using a hardener.

As examples of hardeners used in the present invention, there are listed, for example, hardeners described in column 41 of U.S. Pat. No. 4,678,739, ibid. No. 4,791,042, and JP-A Nos. 59-116655, 62-245261, 61-18942, 61-249054, 61-245153, and 4-218044. More specifically, there are exemplified aldehyde based hardeners (e.g. formaldehyde), aziridine based hardeners, epoxy based hardeners, vinyl sulfone based hardeners (e.g., N,N'-ethylene-bis(vinylsulfonylacetamido)ethane), N-methylol based hardeners (e.g., dimethylol urea), boric acid, metaboric acid, or polymer hardeners (compounds described, for example, in JP-A No. 62-234157). When gelatin is used as a polymer, of these hardeners, a vinyl sulfone based hardener and a chlorotriazine based hardener are preferably used individually or in combination. Further, when a polyvinyl alcohol is used, a boron-containing compound such as boric acid or metaboric acid is preferably used.

There are used 0.001-1 g of, preferably 0.005-0.5 g of these hardeners per 1 g of the water based compound. Further, to enhance film strength, it is optionally possible to carry out heat treatment or moisture controlling during hardening reaction.

In the display element of the invention, various constituent layers other than above mentioned constituents may be provided as appropriate.

[Opposite Electrode (for Display)]

In the display element of the invention, at least one of the opposite electrodes is preferably a metallic electrode. For the metallic electrode, known metal species such as platinum, gold, silver, copper, aluminum, zinc, nickel, titanium, bismuth, and their alloys are usable. Metals having work function near the redox potential of silver in the electrolyte are preferable as the metallic electrode. The electrode is produced by a known method such as a vapor deposition method, printing method, inkjet method, spin coat method and CVD method, for example.

In the display element of the invention, at least one of the opposite electrodes is preferably a transparent electrode. There is no limitation as to the transparent electrode as long as that is transparent and electro conductive. For example, indium tin oxide (ITO), indium zinc oxide (IZO), fluorine-doped tin oxide (FTO), indium oxide, zinc oxide, platinum, gold, silver, rhodium, copper, chromium, carbon, aluminum, silicon, amorphous silicon, bismuth silicon oxide (BOS) are cited. Such the electrode can be formed, for example, by vapor depositing an ITO layer on the substrate through a mask by a spattering method or patterning by a photolithographic method after uniformly forming an ITO layer. The surface conductivity is preferably not more than $100\Omega/\square$ and more preferably not more than $10\Omega/\square$. The thickness of the transparent electrode is usually from 0.1 to 20 μm though there is no limitation.

[Porous Electrode Containing Metal Oxide]

In the display of the invention, a porous electrode containing a metal oxide can also be used.

It is found that the redox reaction of silver or the silver-containing compound on the side not for image viewing is caused on or in the porous layer containing metal oxide when the surface of the electrode on the side not for image viewing among the opposite electrodes is protected by the porous electrode containing metal oxide. As a result of that, the selective range of the kind of the electrode on the side not for image viewing can be expanded and the durability can be improved about.

As the metal oxide constituting the porous electrode relating to the invention, titanium dioxide, silicon oxide, zinc oxide, tin oxide, Sn-doped indium oxide (ITO), antimony-doped tin oxide (ATO), fluorine-doped tin oxide (FTO), aluminum-doped zinc oxide and a mixture of the above are cited.

The porous electrode is constituted by bonding or contacting plural fine particles of the above metal oxide. The average diameter of the metal fine particles is preferably from 5 nm to 10 μm, and more preferably from 20 nm to 1 μm. The specific surface area measured by simplified BET method of the metal oxide fine particles is preferably from $1\times10^{-3}$ to $1\times10^{2}$ $m^{2}/g$, and more preferably from $1\times10^{-2}$ to $10$ $m^{2}/g$. The metal oxide fine particle having optional shape such as irregular, needle like and sphere may be used.

As the method for forming or bonding the metal oxide fine particles, known sol-gel method and sintering method can be applied; for example, the methods described in 1) Journal of the Ceramic Society of Japan, 102, 2, p. 200, (1994), 2) The Yogyo Kyokai Shi, 90, 4, p. 157, and 3) J. of Non-Cryst. Solids, 82, 400, (1986) are cited. A method can be applied, in which titanium dioxide dendrimer prepared by a fuming method is dispersed on a liquid and coated on the substrate and dried at a temperature about 120 to 150° C. for removing the solvent to obtain the porous electrode. The metal oxide particles are preferably in a bonded state and has a tolerance of not less than 0.1 g, more preferably not less than 1 g, measured by a continuous weighting type surface property measuring apparatus such as a scratch tester.

The "porous" in the invention is a state having penetrating pores through which the ion species can be moved in the porous electrode and deposition of silver can be caused when the porous electrode is provided and potential difference is applied between the opposite electrodes.

[Electron Insulation Layer]

In the display of the invention, an electron insulation layer can be provided.

The electron insulation layer applicable to the invention may be a layer having both of ion insulation ability and electron insulation ability. For instance, a solid electrolyte layer formed by filming a polymer having polarity or a salt thereof, a suspected solid layer constituted by a porous layer having high electron insulation ability which carries an electrolyte in the pores thereof, a porous polymer layer having pores and a porous inorganic material having relatively low dielectric constant such as a silicon-containing compound are cited.

As the method for forming the porous layer, the known methods such as the followings can be applied; a sintering (fusion bonding) method in which polymer fine particles or inorganic particles are added to a binder so as to be partially bonded with together and pores formed between the particles are utilized, an extraction method in which a layer constituted by an organic or inorganic substance soluble in a solvent and a binder insoluble in the solvent is formed and then the organic or inorganic substance is dissolved by the solvent so as to form fine pores, a foaming method in which a polymer is heated or degassed to form foams, a phase conversion method in which a polymer is subjected to phase separation by operating a good solvent and a poor solvent and a radiation irradiating method in which one or more radiations are irradiated for forming fine pores. In concrete, the electron insulation layers described in JP-A H10-30181, JP-A 2003-107626, JP-A H7-95403 and U.S. Pat. Nos. 2,636,715, 2,849,523, 2,987,474, 3,066,426, 3,464,513, 3,483,644, 3,535,942 and 3,062,203 can be cited.

[Electrolyte]

"Electrolyte" generally refers to a compound which dissolves in a solvent such as water and the solution exhibits an ionic conductivity (hereafter it is called as "an electrolyte in a narrow definition"). However, in the description of the present invention, a mixture of an electrolyte in a narrow definition and other metal or compound (regardless of electrolytic or non-electrolytic) may be also called as an electrolyte (such a mixture is called as "an electrolyte in a broad definition".)

To the electrolyte of the present invention, any solvents may be used together with the electrolyte to the extent that the targeted effects of the present invention are not adversely affected. Specifically, there can be listed tetramethylurea, sulfolane, dimethylsulfoxide, 1,3-dimethyl-2-imidazolidinone, 2-(N-methyl)-2-pyrrolidinone, hexamethylphospholtriamide, N-methylpropioneamide, N,N-dimethylacetamide, N-methylacetamide, N,N-dimethylformamide, N-methylformamide, butylonitrile, propionitrile, acetonitrile, acetylacetone, 4-methyl-2-pentanone, 2-butanol, 1-butanol, 2-propanol, 1-propanol, ethanol, methanol, acetic anhydride, ethyl acetate, ethyl propionate, dimethoxyethane, diethoxyfuran, tetrahydrofuran, ethylene glycol, diethylene glycol, triethylene glycol monobutyl ether, and water. Of these solvents, at least one type of solvent, featuring a freezing point of at most −20° C. and a boiling point of at least 120° C., is preferably contained.

[Compounds Represented by Formulas (3) and (4)]

In the display element of the present invention, an electrolyte may contain a compound represented by following Formula (3) or (4).

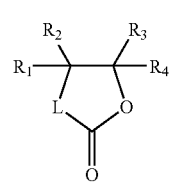

Formula (3)

In Formula (3), L represents an oxygen atom or CH$_2$, and R$_1$-R$_4$ each represent a hydrogen atom, an alkyl group, an alkenyl group, an aryl group, a cycloalkyl group, an alkoxyalkyl group, or an alkoxy group.

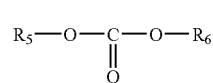

Formula (4)

In Formula (4), R$_5$ and R$_6$ each represent a hydrogen atom, an alkyl group, an alkenyl group, an aryl group, a cycloalkyl group, an alkoxyalkyl group, or an alkoxy group.

Initially, the compound represented by Formula (3) of the present invention will now be described.

In Formula (3), L represents an oxygen atom or CH$_2$, and R$_1$-R$_4$ each represent a hydrogen atom, an alkyl group, an alkenyl group, an aryl group, a cycloalkyl group, an alkoxyalkyl group, or an alkoxy group.

The alkyl group includes, for example, a methyl group, ethyl group, propyl group, isopropyl group, tert-butyl group, pentyl group, hexyl group, octyl group, dodecyl group, tridecyl group, tetradecyl group, and pentadecyl group. The aryl group includes, for example, a phenyl group and naphthyl group. The cycloalkyl group includes, for example, a cyclopentyl group and cyclohexyl group. The alkoxyalkyl group includes, for example, a β-methoxyethyl group and γ-methoxypropyl group. The alkoxy group includes, for example, a methoxy group, ethoxy group, propyloxy group, pentyloxy group, hexyloxy group, octyloxy group, and dodecyloxy group.

Specific examples of the compound represented by Formula (3) will now be listed, but the present invention is not limited only by the following compounds.

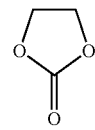

3-1

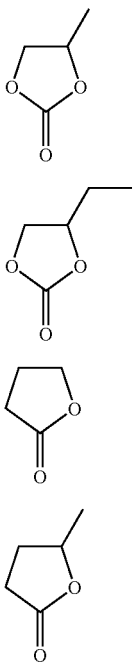

3-2

3-3

3-4

3-5

Secondly, the compound represented by Formula (4) will now be described.

In Formula (4), $R_5$ and $R_6$ each represent a hydrogen atom, an alkyl group, an alkenyl group, an aryl group, a cycloalkyl group, an alkoxyalkyl group, or an alkoxy group.

The alkyl group includes, for example, a methyl group, ethyl group, propyl group, isopropyl group, tert-butyl group, pentyl group, hexyl group, octyl group, dodecyl group, tridecyl group, tetradecyl group, and pentadecyl group. The aryl group includes, for example, a phenyl group and naphthyl group. The cycloalkyl group includes, for example, a cyclopentyl group and cyclohexyl group. The alkoxyalkyl group includes, for example, a β-methoxyethyl group and γ-methoxypropyl group. The alkoxy group includes, for example, a methoxy group, ethoxy group, propyloxy group, pentyloxy group, hexyloxy group, octyloxy group, and dodecyloxy group.

Specific examples of the compound represented by Formula (4) will now be listed, but the present invention is not limited only by the following compounds.

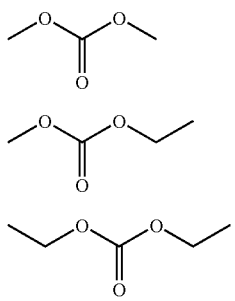

4-1

4-2

4-3

Of the exemplified compounds represented by Formula (3) and Formula (4), exemplified compounds (3-1), (3-2), and (4-3) are specifically preferable.

Any of the compounds represented by above Formulas (3) and (4) is a kind of electrolyte solvent. In the display element of the present invention, the above-described electrolyte solvent can further be used together within the range where no targeted effects of the present invention are impaired.

Solvents employable in the present invention further include compounds described in J. A. Riddick, W. B. Bunger, T. K. Sakano, "Organic Solvents", 4th ed., John Wiley & Sons (1986); Y. Marcus, "Ion Solvation", John Wiley & Sons (1985); C. Reichardt, "Solvents and Solvent Effects in Chemistry", 2nd ed., VCH (1988); and G. J. Janz, R. P. T. Tomkins, "Nonaquaeous Electrolytes Handbook", Vol. 1., Academic Press (1972).

In the present invention, the electrolyte solvent may be used in alone or in mixture. A solvent mixture containing ethylene carbonate is preferably used. Preferable content of ethylene carbonate is 10% or more and 90% or less by mass based on a total mass of electrolyte solvent. Especially preferable electrolyte solvent is a mixture solvent having a mass ratio of propylene carbonate to ethylene carbonate between 7/3 and 3/7. When the mass ratio of propylene carbonate to ethylene carbonate is larger than 7/3, an ion conductivity becomes lower and a response time becomes lower. When the mass ratio of propylene carbonate to ethylene carbonate is less than 3/7, an electrolyte may occur precipitation at low temperature.

[Concentration Ratio of Halogen Ions and Silver Ions]

In the display of the invention, it is preferable that the mole concentration of halogen ions or halogen atoms contained in the electrolyte [α](mol/kg) and the mole concentration of sum of silver or silver contained in the chemical structure of the silver-containing compound [Ag] (mole/kg) satisfy the condition represented by the following Expression 1.

$$0 \leq [X]/[Ag] \leq 0.01$$ Expression 1

In the invention, the halogen atom is an iodine atom, a chlorine atom, a bromine atom or a fluorine atom. When [X]/[Ag] is 0.01 or more, $X^- \rightarrow X_2$ is caused on the occasion of redox reaction of silver and $X_2$ easily causes cross-oxidation of blacken silver so as to dissolve the silver and makes a cause of lowering in the memorizing ability. Therefore, the mole number of the halogen atom is as lower as possible than that of silver. In the invention, the condition of $0 \leq [X]/[Ag] \leq 0.001$ is more preferable. As to the kind of halogen, the sum of each of the kinds of halogen is preferably [I]<[Br]<[Cl]<[F] when halogen ions are added.

In the display of the invention, a silver solvent other than halogen may be utilized for solving a silver compound. Preferable silver salt solvent includes a compound described in Formulas (1) to (7) in JP-A 2005-266652. Among them, compounds represented by Formula (2) and (6) are especially preferable. [Electrolyte material]

In the display of the invention, when the electrolyte is a liquid, the following compounds may be contained in the electrolytes; examples of such the compound include a potassium compound such as KCl, KI and KBr, a lithium compound such as $LiBF_4$, $LiClO_4$, $LiPF_6$ and $LiCF_3SO_3$, and a tetralakylammonium compound such as tetraethylammonium perchlorate, tetrabutylammonium perchlorate, tetraethylammonium borofluoride and a terabutylammonium halide. The melted electrolyte compositions described in JP-A 2003-187881, [0062] to [0081] are also preferably usable. Moreover, a compound formable a redox pair such as $I^-/I_3^-$, $Br^-/Br_3^-$ and quinine/hydroquinone can be used.

When the supported electrolyte is solid, a compound below which exhibits an electron conductivity or an ionic conductivity may be included in the electrolyte, such as fluorovinyl polymer having perfluorosulfonic acid, polythiophene, polyaniline, polypyrrole, triphenylamines, polyvinylcarbazoles, polymethylphenylsilanes, carcogenides such as $Cu_2S$, $Ag_2S$, $Cu_2Se$, $AgCrSe_2$; compound containing fluorine atom such as $CaF_2$, $PbF_2$, $SrF_2$, $LaF_3$, $TlSn_2F_5$, $CeF_3$; lithium salt such as $Li_2SO_4$, $Li_4SiO_4$, $Li_3PO_4$; and $ZrO_2$, CaO, $Cd_2O_3$, $HfO_2$, $Y_2O_3$, $Nb_2O_5$, $WO_2$, $Bi_2O_3$, AgBr, AgI, CuCl, CuBr, CuBr, CuI, LiI, LiBr, LiCl, $LiAlCl_4$, $LiAlF_4$, AgSBr, $C_5H_5NHAg_5I_6$, $Rb_4Cu_{16}I_7Cl_{13}$, $Rb_2Cu_7Cl_{10}$, LiN, $Li_5NI_2$ and $Li_6NBr_3$.

Further an electrolyte in a gel state may be used. When an electrolyte is non-aqueous, an oil gelling agent described in paragraph [0057]-[0059] of JP-A 11-185836 can be used.

[Thickener To be Added To Electrolyte]

In the display of the invention, a thickener can be used in the electrolyte. For example, gelatin, gum arabic, poly(vinylalcohol), hydroxyethylcellulose, hydroxypropylcellulose, cellulose acetate, cellulose acetate butylate, poly(vinyl pyrolidone), a poly(alkylene glycol), casein, starch, poly(acrylic acid), poly(methyl methacrylate), poly(vinyl chloride), poly(methacrylic acid), styrene-maleic anhydride copolymer, styrene-acrylonitrile copolymer, styrene-butadiene copolymer; poly(vinyl acetals) such as poly(vinylformal) and poly(vinyl butylal); polyesters, polyurethanes, phenoxy resin, poly(vinylidene chloride), polyepoxides, polycarbonates, polyvinylacetate, cellulose esters, polyamides, and a hydrophobic transparent binder such as polyvinyl butylal, cellulose acetate, cellulose acetate butylate, polyester, polycarbonate, poly(acrylic acid) and polyurethane are usable.

These thickeners can be used in either alone or in combination of two or more thereof. Further compounds described in Page 71-75 in JP-A 64-13546 can be used as the thickener. Among them, preferable compound includes polyvinylalcohols, polyvinylpyrrolidones, hydroxypropylcelluloses, polyalkyleneglycols, from the standpoint of compatibility with other additives and dispersion stability of white particles.

[Another additive]

As the constituting layer of the display of the invention, auxiliary layers such as a protection layer, filter layer, antihalation layer, crossover light cutting layer and backing layer are cited. In such the auxiliary layers, various chemical sensitizers, noble metal sensitizers, optical sensitizing dyes, super sensitizers, couplers, high-boiling solvents, antifoggants, stabilizers, development inhibitors, bleach accelerators, fixing accelerators, color mixing preventing agents, formalin scavengers, tone controlling agents, hardeners, surfactants, thickeners, plasticizers, lubricants, UV absorbents, irradiation preventing agent, light absorbing filter dyes, anti-mold agent, polymer latexes, heavy metals, antistatic agent and matting agent can be contained according to necessity.

The above additives are described in detail in Research Disclosure, hereinafter referred to as $R^D$, vol. 176, Item/17643 (December 1978), vol. 184, Item/18431 (August 1979), vol. 187, Item/18716 (November 1979), and vol. 308, Item/308119 (December 1989).

The kinds of compounds and the description position thereof in the above three Research Disclosures are shown below.

| Additive | RD17643 Page | Class | RD18716 Page | RD308119 Page | Class |
|---|---|---|---|---|---|
| Chemical sensitizer | 23 | III | 648UR | 96 | III |
| Sensitizing dye | 23 | IV | 648-649 | 996-8 | IV |
| Desensitizing dye | 23 | IV | | 998 | IV |
| Dye | 25-26 | VIII | 649-650 | 1003 | VIII |
| Developing accelerator | 29 | XXI | 648UR | | |
| Antifoggant/Stabilizer | 24 | IV | 649UR | 1006-7 | VI |
| Whitening agent | 24 | V | | 998 | V |
| Hardener | 26 | X | 651L | 1004-5 | X |
| Surfactant | 26-27 | XI | 650R | 1005-6 | XI |
| Antistatic agent | 27 | XII | 650R | 1006-7 | XIII |
| Plasticizer | 27 | XII | 650R | 1006 | XII |
| Lubricant | 27 | XII | | | |
| Matting agent | 28 | XVI | 650R | 1008-9 | XVI |
| Binder | 26 | XXII | | 1003-4 | IX |
| Support | 28 | XVII | | 1009 | XVII |

In the above, UR, R and L is each upper right, right and left, respectively.

[Metallocene Compound]

A metallocene derivative can be used in a constitution layer of the display element of the present invention. A ferrocene derivative is preferably used as an example of a metallocene derivative. Specific examples of a ferrocene derivative are: ferrocene, methylferrocene, dimethylferrocene, ethylferrocene, propylferrocene, n-butylferrocene, t-butylferrocene, and 1,1-dicarboxylferrocene. A metallocene derivative can be used singly or used as a mixture of two or more metallocene derivatives.

[Layer Structure]

The layer structure between the opposite electrodes in the display of the invention is further described below.

The display element of the present invention is characterized in that black display, white display, and multi-color display of at least 3 colors which is colored display other than black are practically carried out by a driving operation of the opposite electrodes.

In the display element of the present invention, one opposite electrode facing the other is provided in the display section. A transparent electrode such as an ITO electrode is provided for electrode 1 which is the one opposite electrode near the display section, and a metal electrode such as a silver electrode is provided for electrode 2 which is the other one. Between electrode 1 and electrode 2, an electrolyte containing a silver (salt) compound is held. By applying a voltage of positive and negative polarities between the opposite electrodes, redox reaction of silver and oxidation-reduction of an electrochromic compound are carried out on electrode 1 and electrode 2. Thereby, utilizing the difference in colored state between the oxidation-reduction states of the both compounds, as well as a white scattering material arranged between the electrodes, it is possible to realize a black silver image in the reduced state and white display or color colored display in the oxidized state.

Further, in colored display other than black, color display and black and white display are preferably conducted via level arrangement of display areas creating hues practically differing from one another. In the method of the level arrangement of display areas creating different hues, electrochromic compounds of different type are preferably held in a metal oxide porous layer. With regard to such holding of the electrochromic compounds in the metal oxide porous layer, a method of separate coating formation using an ink-jet method is specifically preferably applied.

In the case of full-color display performed in the display element of the present invention, there are listed a method of level arrangement wherein a pair of opposite electrodes are divided by partition walls and electrolytic solutions for different coloring (electrolytes containing different types of electrochromic compounds) are encapsulated in each partition wall; and a method wherein using no partition walls, different electrochromic compounds are separately coated and held on a metal oxide porous layer. Such a separate coating method includes a printing method and an ink-jet method. In the present invention, the ink-jet method is specifically preferably used.

[Substrate]

As a substrate usable in the present invention, there are also preferably used a synthetic plastic film including a polyolefin such as polyethylene or polypropylene, a polycarbonate, cellulose acetate, polyethylene terephthalate, polyethylene dinaphthalene dicarboxylate, a polystyrene naphthalate, polyvinyl chloride, polyimide, a polyvinyl acetal, and polystyrene. A syndiotactic structure polystyrene is also preferable. These can be prepared via the methods described, for example, in each of JP-A Nos. 62-117708, 1-46912, and 1-178505. Further, there are exemplified metal substrates such as stainless steel; paper supports such as baryta paper or resin coated paper; supports prepared by arranging a reflection layer on any of the above plastic films; and those which are described in JP-A No. 62-253195 (pages 29-31) as supports. There can also preferably be used those described on page 28 of RD No. 17643; from the right column of page 647 to the left column of page 648 of RD No. 18716; and on page 879 of RD No. 307105. As these substrates, there can be used those heat-treated at a temperature of at most Tg so that core-set curl is decreased, as described in U.S. Pat. No. 4,141, 735. Further, any of these supports may be surface-treated to enhance adhesion of the support to other constituent layers. In the present invention, there may be employed, as surface treatment, glow discharge treatment, ultraviolet irradiation treatment, corona discharge treatment, and flame treatment. Further, the supports described on pages 44-149 of Kochi Gijutsu (Known Techniques), No. 5 (issued on Mar. 22, 1991, published by Aztech Corp.) may be used. Still further, there are listed those described on page 1009 of RD, No. 308119, and in "Supports" of Product Licensing Index, Vol. 92, Page 108. In addition, glass substrates, and epoxy resins kneaded with glass powder are employable.

[Another Constituent of Display]

In the display element of the invention, a sealing agent, columnar structural material and spacer particle can be used according to necessity.

The sealing agent is a material for preventing leak of the contents and is also called as a sealant, and a curable resin such a thermal curable type, photo curable type, a moisture curable type and an anaerobic curable resins, for example, an epoxy resin, a urethane type resin, an acryl type resin, a vinyl acetate type resin, an ene-thiol type resin, a silicone type resin and a modified-polymer resin are usable.

The columnar structural material gives strong self hold ability (strength) between the substrates, for example, structural materials having shape of columnar, prism, oval columnar, trapezoidal prism each arranged at a certain space to form a designated pattern such as a lattice orientation can be applied. The structural material may also be a stripe-shaped material arranged at a certain interval. It is preferable that the arrangement of the columnar materials is considered so that the space between the substrates is suitably held and the image display is not disturbed, such the arrangement includes an arrangement having the equal interval, the gradually varying interval and that in which a designated patter is repeated at a certain cycle without random arrangement. Practically suitable strength for the display can be obtained when the ratio of the area occupied by the columnar structural material is from 1 to 40% of the area of the display.

A spacer may be provided for keeping uniformity of the gap between the pair of the substrates. As the spacer, a sphere of resin or inorganic material can be exemplified. A fixing spacer having a thermoplastic resin coating layer on the surface thereof is also suitably usable. For uniformly holding the gap between the substrates, the columnar structural material may be used solely or together with the spacer or the spacer is solely used instead of the columnar structural material. The diameter of the spacer is lower than or preferably the same as the height of the columnar structural material when such the structural material is formed. When no columnar structural material is formed, the diameter of the spacer corresponds to the thickness of the cell gap.

[Screen Printing]

In the invention, the sealing agent, columnar structural material and electrode can be pattered by the screen printing. In the screen printing, a screen having designated patterns formed thereon is overlapped on the electrode surface of the substrate and the material to be printed (a composition for forming the columnar structure such as photo curable resin) is put on the screen and a squeezer is moved at a designated pressure, angle and speed. Thus the material to be printed is transferred on to the substrate through the patterns on the screen, and then the transferred material is thermally cured and dried. When the columnar structural material is formed by the screen printing, the resin material is not limited to the photo curable resin and a thermally curable resin such as epoxy resin and acryl resin and a thermoplastic resin are also applicable. As the thermoplastic resin, poly(vinyl chloride) resin, poly(vinylidene chloride) resin, poly(vinyl acetate) resin, polymethacrylate resin, polyacrylate resin, polystyrene resin, polyamide resin, polyethylene resin, polypropylene resin, fluoro resin, polyurethane resin, polyacrylonitrile resin, poly(vinyl ether) resin, poly(vinyl ketone) resin, polyether resin, polyvinylpyrrolidone resin, saturated polyester resin, polycarbonate resin and poly(ether chloride) resin are cited. The resin is preferably used in a paste state by dissolving a suitable solvent.

After the columnar structural material is formed on the substrate as above, the spacer is provided onto at least one of the substrate according to necessity and one of the pair of the substrates is placed on the other so as to be faced the electrode forming surface to prepare an empty cell. The piled pair of the substrates is pasted by heating while pressing from both sides to form a display cell. For completing the display element, the electrolyte composition is injected between the substrates by a vacuum injection method. In otherwise, it is allowed that the electrolyte composition is previously dropped on one of the substrate on the occasion of pasting so that the liquid crystal composition is enclosed together with the pasting at the same time.

[Driving Method of Display Element]

In the display element of the invention, the driving method is preferably applied, in which the deposition of blacken silver is carried out by applying a voltage higher than the deposition overpotential and the deposition is continued by applying a voltage lower than the deposition overpotential. In the display element of the present invention, it is preferable to perform a driving operation such that blackened silver is deposited by applying a voltage of at least the deposition overpotential and the deposition of blackened silver is continued by applying a voltage of at most the deposition overpotential. Performance of such a driving operation results in reduced writing energy, reduced load of the drive circuit, and enhanced writing speed as an image screen. Existence of overpotential in electrode reaction is generally known in the electrochemistry field. The overpotential is detailed, for example, on page 121 of "Denshi-ido no Kagaku/Denkikagaku Nyumon (Chemistry of Electron Transfer/Introduction to Electrochemistry)" (1996, published by Asakura Shoten). The display element of the present invention is also regarded as electrode reaction of an electrode with silver in an electrolyte so that existence of an overpotential in silver dissolution and deposition is readily understood. Since the magnitude of an overpotential is controlled by an exchange current density, from the fact that after formation of blackened silver, deposition of blackened silver can be continued via application of a voltage of at most a deposition overpotential, it is presumed that the surface of blackened silver has less excess energy, resulting in easy electron injection.

The driving operation of the display element of the invention may be simple matrix derive or active matrix drive. The simple matrix drive in the invention is a driving method in which electric current is successively applied to a circuit constituted by an anode line containing plural anodes and a cathode line containing plural cathodes which are faced so that the lines are crossed at a right angle. The use of the simple matrix drive has merits that the circuit configuration and the driving IC can be simplified and the cost can be lowered. The active matrix is a method in which the driving is carried out by TFT circuits each formed at the crossing point of lattice constituted by scanning lines, data lines and electric current supplying lines. Such the method has merits of gradation and memory function since switching can be performed by every pixel, for example, the circuit described in JP-A 2004-29327, FIG. 5 can be used. In the present invention, as a driving method to display plural colors between a pair of opposite electrodes in the display element of the present invention, there are listed 1) a method wherein the overvoltages during oxidation and reduction are varied among each of the redox compounds and an operation for the magnitude of the voltage is conducted to cover between the upper level and lower level of the overvoltages; 2) a method wherein the redox rate of each of the redox compounds is varied and an operation for voltage application duration is conducted; and 3) a method wherein an operation for the resistance value of the circuit portions except for the display section between the opposite electrodes is conducted, and then, for example, an operation is conducted utilizing the difference between the characteristics of being decolored and the characteristics of being not decolored from the colored state via short-circuiting of the both electrodes.

In a method for driving the display element of the present invention, the driving is preferably carried out under conditions where the coloring overvoltage (VECW) and the decoloring overvoltage (VECE) of an electrochromic dye, and the deposition overvoltage (VAgW) and the dissolution overvoltage (VAgE) of silver of a silver salt compound satisfy all the conditions defined by following Relational Expression (X).

VECW absolute value>VECE absolute value

VECW absolute value>VAgE absolute value

VAgW absolute value>VECE absolute value

VAgW absolute value>VAgE absolute value    Relational Expression (X)

In the display element of the present invention, when the observation-side electrode functions as an anode, the color colored state is realized, and when the electrode functions as a cathode, the black colored state is realized. The intermediate state is realized as white display. It is possible that returning from the color colored state to white display or from the black colored state to white display is conducted by a decoloring operation for an amount depending on the degree of each of color coloring and black coloring.

In this case, it is necessary that the display element should hold information on the degree of each coloring. In a method for driving the display element of the present invention, the driving is preferably carried out under conditions where the voltage (VW) between the opposite electrodes during the white display driving operation satisfies all the conditions defined by following Relational Expression (Y).

VECW absolute value>VW>VECE absolute value

VECW absolute value>VW>VAgE absolute value

VAgW absolute value>VW>VECE absolute value

VAgW absolute value>VW>VAgE absolute value    Relational Expression (Y)

In Relational Expression (Y), VECW, VECE, VAgE, and VAgW have the same meanings as in above Relational Expression (X).

With regard to the method for driving the display element of the present invention, when the driving is carried out so as to satisfy all the conditions defined by Relational Expression (Y), it is unnecessary to hold information on the degree of coloring, whereby the display element can unambiguously be returned from any colored state to white display, which is advantageous.

[Commercial Application]

The display element of the invention can be applied in the fields relating to electronic book, ID card, public, transport, broad casting, accounting and commodity distribution. In concrete, the followings are cited; a door key, student identification card, staff identification card, various member's card, convenience store card, department store card, automatic selling machine card, gasoline station card, subway or rail way card, bus card, cash card, credit card, highway card, driving license, medical consultation ticket, clinical record, health insurance certificate, residence registration ledger, passport and electronic book.

EXAMPLES

The present invention will now specifically be described with reference to Examples that by no means limit the scope of the present invention. Herein, "part" or "%" referred to in Examples represents "part by mass" or "% by mass" unless otherwise specified.

Example 1

Production of Display Element 1

(Preparation of Electrolytic Solution 1)

There were dissolved 0.1 g of silver iodide, 0.15 g of sodium iodide, 0.05 g of polyethylene glycol (average molecular weight: 500,000), and 0.1 g of 3,3,-dimethyl-2-(p-dimethylaminostyryl)indolino[2,1-b]oxazoline (hereinafter referred to as IRPDM) in 2.5 g of dimethyl sulfoxide to obtain electrolytic solution 1.

(Production of Electrode 1)

An ITO (indium tin oxide) film of a pitch of 145 μm and an electrode width of 130 μm was formed on a glass substrate of 2 cm×4 cm having a thickness of 1.5 mm via a conventionally known method to obtain electrode 1 which was a transparent one.

(Production of Electrode 2)

A silver-palladium electrode having an electrode thickness of 0.8 μm, a pitch of 145 μn, and an electrode width of 130 μm was formed on a glass substrate of 2 cm×4 cm having a thickness of 1.5 mm via a conventionally known method. This electrode was designated as electrode 2.

(Production of Electrode 3)

There was coated, for a length of 100 μm, a mixed liquid prepared by dispersing 20% by mass of titanium oxide in an isopropanol solution containing polyvinyl alcohol (average polymerization degree: 3500; and saponification degree: 87%) at 2% by mass using an ultrasonic homogenizer on electrode 2 whose peripheral portion was edged with an olefin-based sealing agent containing glass spherical beads of an average particle diameter of 40 μm at 10% by volume, and then drying was carried out at 15° C. for 30 minutes to evaporate the solvent, followed by drying under an ambience of 45° C. for 1 hour to produce electrode 3.

(Production of Display Elements)

Electrode 3 and electrode 1 were bonded together at right angles to each stripe electrode, followed by being heat-pressed to produce a vacant cell. Electrolytic solution 1 was vacuum-injected into the vacant cell, and then the injection inlet was sealed with an epoxy-based UV curable resin to produce display element 1.

[Evaluation of Display Element 1]

Both electrodes of display element 1 were connected to both terminals of a constant voltage power supply and a voltage of ±1.5 V was applied. The colored state of the display element was observed and reflectance was measured using the D65 light source of spectrophotometer CM-3700d (produced by Konica Minolta Sensing, Inc.). Display element 1 realized white display stemming from the reduction state of IRPDM and the oxidation state of silver during no voltage application; magenta display (maximum absorption wavelength: 547 nm) stemming from the oxidation state of IRPDM during +1.5 V application on the transparent electrode side; and black display stemming from the reduction state of silver during −1.5 V application on the transparent electrode side. Accordingly, the results showed that multi-color display of 3 colors was realized using one type of electrolyte between a pair of opposite electrodes.

Example 2

Production of Display Element 2

Electrolytic solution 2 was prepared in the same manner as for electrolytic solution 1 used in production of above display element 1 except that IRPDM was changed to an equimolar amount of exemplified compound 13 of Formula (A). Subsequently, display element 2 was produced in the same manner as in production of display element 1 except that electrolytic solution 1 was changed to electrolytic solution 2.

Evaluation of Display Element 2

Display element 2 was evaluated in the same manner as for display element 1 as described above. Display element 2 realized white display during no voltage application; cyan display (maximum absorption wavelength: 645 nm) during +1.5 V application; and black display during −1.5 V application. Accordingly, the results showed that multi-color display of 3 colors was realized using one type of electrolyte between a pair of opposite electrodes.

In display element 2, the overvoltage for cyan coloring was 0.8 V and the overvoltage for cyan decoloring was −0.3 V. The overvoltage for black coloring was −0.6 V and the overvoltage for black decoloring was +0.3 V. When an alternating voltage of ±0.4 V was applied at 10 Hz to display element 2 having varied degrees of cyan coloring and black coloring, returning to white display was confirmed regardless of the degree of coloring.

Example 3

Production of Display Element 3

Electrolytic solutions 4 and 5 were prepared in the same manner as for electrolytic solution 2 used in production of display element 2 described in Example 2 except that 0.3 g of titanium oxide was added and further exemplified compound 13 of Formula (A) was changed to an equimolar amount of exemplified compound 105 and exemplified compound 4 of Formula (A), respectively.

The peripheral portion of electrode 2 described in Example 1 was edged with an olefin-based sealing agent containing glass spherical beads of an average particle diameter of 20 μm at 10% by volume. And then a partition wall having 100 μm square windows was formed on the pixel portions intersecting with electrode 1 via photolithography to produce electrode 4. Electrolytic solutions 3, 4, and 5 were injected into the individual windows separately via Bayer arrangement using a dispenser. Further, electrode 1 was bonded at right angles to each stripe electrode to produce display element 3.

Evaluation of Display Element 3

Display element 3 was subjected to simple matrix driving by varying the applied voltage of each pixel.

Observation of the tone of the display element showed that each color of white, black, yellow, magenta, cyan, blue, green, and red was able to be displayed. Further, the reflectance during white display and the reflectance during black display of the display element at 550 nm were 62% and 4%, respectively. The display element of the present invention was confirmed to be able to realize enhanced white reflectance, high black and white contrast, and color display with a simple member constitution.

Example 4

Production of Display Element 4

Inks 1-3 were prepared by dissolving 0.3 g of each of exemplified compounds 42, 108, and 115 of Formula (A) in 2.5 g of ethanol. Electrolytic solution 6 was prepared by dissolving 0.1 g of silver iodide, 0.15 g of sodium iodide, and 0.05 g of polyethylene glycol (average molecular weight: 500) in 2.5 g of dimethyl sulfoxide.

An ITO film of a pitch of 145 μm and an electrode width of 130 μm was formed on a glass substrate of 2 cm×4 cm having a thickness of 1.5 mm via a conventionally known method. Titanium oxide (average particle diameter: 25 nm) was coated thereon at a ratio of 10 g/m², followed by firing at 350° C. for 1 hour. Electrode 5 with the thus-formed metal oxide porous film was obtained. Using a commercially available ink-jet coating apparatus, inks 1-3 were separately coated on electrode 5 via Bayer arrangement to produce electrode 6. Electrode 6 and electrode 1 were bonded together at right angles to each stripe electrode, followed by being heat-pressed to produce a vacant cell. Electrolytic solution 6 was vacuum-injected into the vacant cell, and then the injection inlet was sealed with an epoxy-based UV curable resin to produce display element 4.

Evaluation of Display Element 4

Display element 4 was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 68% and 3%, respectively. The display element of the present invention was confirmed to be able to realize enhanced white reflectance, high black and white contrast, and color display with a simple member constitution.

Example 5

Production of Display Element 1a (Preparation of Electrolytic Solution 1a)
There were dissolved 0.1 g of silver iodide, 0.15 g of sodium iodide, 0.05 g of polyethylene glycol (average molecular weight: 500,000), and 0.1 g of 4,4'-biphenyldicarboxylic acid (hereinafter referred to as BCE) in 2.5 g of dimethyl sulfoxide to obtain electrolytic solution 1a.

(Production of Electrode 1a)
An ITO (indium tin oxide) film of a pitch of 145 μm and an electrode width of 130 μm was formed on a glass substrate of 2 cm×4 cm having a thickness of 1.5 mm via a conventionally known method to obtain electrode 1a which was a transparent one.

(Production of Electrode 2a)
A silver-palladium electrode having an electrode thickness of 0.8 μm, a pitch of 145 μn, and an electrode width of 130 μm was formed on a glass substrate of 2 cm×4 cm having a thickness of 1.5 mm via a conventionally known method. This electrode was designated as electrode 2a.

(Production of Electrode 3a)
There was coated, for a length of 100 μm, a mixed liquid prepared by dispersing 20% by mass of titanium oxide in an isopropanol solution containing polyvinyl alcohol (average polymerization degree: 3500; and saponification degree: 87%) at 2% by mass using an ultrasonic homogenizer on electrode 2 whose peripheral portion was edged with an olefin-based sealing agent containing glass spherical beads of an average particle diameter of 40 μm at 10% by volume, and then drying was carried out at 15° C. for 30 minutes to evaporate the solvent, followed by drying under an ambience of 45° C. for 1 hour to produce electrode 3a.

(Production of Display Element 1a)
Electrode 3a and electrode 1a were bonded together at right angles to each stripe electrode, followed by being heat-pressed to produce a vacant cell. Electrolytic solution 1a was vacuum-injected into the vacant cell, and then the injection inlet was sealed with an epoxy-based UV curable resin to produce display element 1a.

Evaluation of Display Element 1a

Both electrodes of display element 1a were connected to both terminals of a constant voltage power supply and a voltage of ±1.5 V was applied. The colored state of the display element was observed and reflectance was measured using the D65 light source of spectrophotometer CM-3700d (produced by Konica Minolta Sensing, Inc.). Display element 1a realized white display stemming from the oxidation state of BCE and the oxidation state of silver during no voltage application; black display stemming from the oxidation state of BCE and the oxidation state of silver during +1.5 V application; and black display stemming from the reduction state of silver during −1.5 V application on the transparent electrode side, as well as realizing mix-colored display of yellow stemming from the reduction state of BCE and black stemming from the reduction state of silver during −2.5 V application on the transparent electrode side; and yellow display stemming from the reduction state of BCE via application of +1.5 V for 300 msec after −2.5 V application. Accordingly, the results showed that multi-color display of 3 colors was realized using one type of electrolyte between a pair of opposite electrodes.

Example 6

Production of Display Element 2a

Electrolytic solution 3a and electrolytic solution 4a were prepared in the same manner as for electrolytic solution 1a used in production of display element 1a described in Example 5 except that 0.3 g of titanium oxide was added and further BCE was changed to an equimolar amount of dimethyl terephthalate and 1,4-diacetylbenzene, respectively.

The peripheral portion of electrode 2a described in Example 5 was edged with an olefin-based sealing agent containing glass spherical beads of an average particle diameter of 20 μm at 10% by volume. And then a partition wall having 100 μm square windows was formed on the pixel portions intersecting with electrode 1a via photolithography to produce electrode 4a. Electrolytic solutions 2a, 3a, and 4a were injected into the individual windows separately via Bayer arrangement using a dispenser. Further, electrode 1a was bonded at right angles to each stripe electrode to produce display element 2a.

[Evaluation of Display Element 2a]
Display element 2a was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 58% and 4%, respectively. The display element of the present invention was confirmed to be able to realize enhanced white reflectance, high black and white contrast, and color display with a simple member constitution.

Example 7

Production of Display Element 3a

Inks 1a-3a were prepared by dissolving 0.3 g of each of exemplified compounds (2-2), (2-4), and (2-15) of Formula (2) in 2.5 g of ethanol. Electrolytic solution 5a was prepared by dissolving 0.1 g of silver iodide, 0.15 g of sodium iodide, and 0.05 g of polyethylene glycol (average molecular weight: 500) in 2.5 g of dimethyl sulfoxide.

An ITO film of a pitch of 145 μm and an electrode width of 130 μm was formed on a glass substrate of 2 cm×4 cm having a thickness of 1.5 mm via a conventionally known method. Titanium oxide (average particle diameter: 25 nm) was coated thereon at a ratio of 10 g/m², followed by firing at 350° C. for 1 hour. Electrode 5a with the thus-formed metal oxide porous film was obtained. Using a commercially available ink-jet coating apparatus, inks 1a-3a were separately coated on electrode 5a via Bayer arrangement to produce electrode 6a. Electrode 6a and electrode 1a were bonded together at right angles to each stripe electrode, followed by being heat-pressed to produce a vacant cell. Electrolytic solution 5a was vacuum-injected into the vacant cell, and then the injection inlet was sealed with an epoxy-based UV curable resin to produce display element 3a.

[Evaluation of Display Element 3a]

Display element 3a was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 62% and 3%, respectively. And the contrast of display element 3a was higher than that of display element 2a. Accordingly, the display element of the present invention was confirmed to be able to realize enhanced white reflectance, high black and white contrast, and color display with a simple member constitution.

Example 8

Production and Evaluation of Display Elements

[Production of Display Element 1b]

(Preparation of Electrolytic Solution 1b)

There were mixed 0.1 g of silver iodide, 0.15 g of sodium iodide, 0.05 g of polyethylene glycol (average molecular weight: 500,000), and 0.07 g of phenothiazine in 2.5 g of dimethyl sulfoxide to obtain electrolytic solution 1b.

(Production of Electrode 1b)

An ITO (indium tin oxide) film of a pitch of 145 µm and an electrode width of 130 µm was formed on a glass substrate of 2 cm×4 cm having a thickness of 1.5 mm via a conventionally known method to obtain a transparent electrode (electrode 1b).

(Production of Electrode 2b)

A silver-palladium electrode having an electrode thickness of 0.8 µm, a pitch of 145 µm, and an electrode width of 130 µm was formed on a glass substrate of 2 cm×4 cm having a thickness of 1.5 mm via a conventionally known method. This electrode was designated as electrode 2b.

(Production of Electrode 3b)

There was coated, for a length of 100 µm, a mixed liquid prepared by dispersing 20% by mass of titanium oxide in an isopropanol solution containing polyvinyl alcohol (average polymerization degree: 3500; and saponification degree: 87%) at 2% by mass using an ultrasonic homogenizer on electrode 2b whose peripheral portion was edged with an olefin-based sealing agent containing glass spherical beads of an average particle diameter of 40 µm at 10% by volume, and then drying was carried out at 15° C. for 30 minutes to evaporate the solvent, followed by drying under an ambience of 45° C. for 1 hour to produce electrode 3b.

(Production of Display Elements)

Electrode 3b and electrode 1b were bonded together at right angles to each stripe electrode, followed by being heat-pressed to produce a vacant cell. Electrolytic solution 1b was vacuum-injected into the vacant cell, and then the injection inlet was sealed with an epoxy-based UV curable resin to produce display element 1b.

(Evaluation of Display Element 1b)

Both electrodes of display element 1b were connected to both terminals of a constant voltage power supply and a voltage of ±1.5 V was applied. The colored state of the display element was observed and reflectance was measured using the D65 light source of spectrophotometer CM-3700d (produced by Konica Minolta Sensing, Inc.). Display element 1b realized white display stemming from the reduction state of phenothiazine and the oxidation state of silver during no voltage application; green display (maximum absorption wavelengths: 450 and 660 nm) stemming from the oxidation state of phenothiazine during +1.5 V application; and black display stemming from the reduction state of silver during −1.5 V application on the transparent electrode side. Accordingly, the results showed that multi-color display of 3 colors was realized using one type of electrolyte between a pair of opposite electrodes.

[Production of Display Element 2b]

Electrolytic solution 2b was prepared in the same manner as for electrolytic solution 1b used in production of above display element 1b except that phenothiazine was changed to an equimolar amount of phenazine.

Subsequently, display element 2b was produced in the same manner as in production of display element 1b except that electrolytic solution 1b was changed to electrolytic solution 2b.

(Evaluation of Display Element 2b)

Display element 2b was evaluated in the same manner as for display element 1b as described above. Display element 2b realized white display during no voltage application; red display (maximum absorption wavelength: 430 nm) during +1.5 V application; and black display during −1.5 V application. Accordingly, the results showed that multi-color display of 3 colors was able to be realized using one type of electrolyte between a pair of opposite electrodes.

Production of Display Element 3b (Preparation of Electrolytic Solutions)

Electrolytic solution 3b was prepared in the same manner as for electrolytic solution 2b used in production of above display element 2b except that 0.3 g of titanium oxide was added.

Further, electrolytic solutions 4b and 5b were prepared in the same manner as in preparation of above electrolytic solution 3b except that phenazine was changed to an equimolar amount of phenothiazine and following compound 1, respectively.

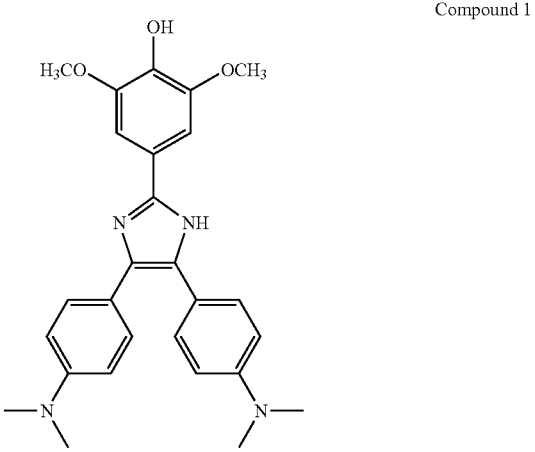

Compound 1

(Production of a Display Element)

The peripheral portion of above electrode 2b was edged with an olefin-based sealing agent containing glass spherical beads of an average particle diameter of 20 µm at 10% by volume. And then a partition wall having 100 μm square windows was formed on the pixel portions intersecting with electrode 1b via photolithography to produce electrode 4b. Electrolytic solutions 3b, 4b, and 5b were injected into the individual windows separately via Bayer arrangement using a dispenser. Further, electrode 1b was bonded at right angles to each stripe electrode to produce display element 3b.

(Evaluation of the Display Element)

Display element 3b was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 62% and 4%, respectively. The display element of the present invention was confirmed to be able to realize enhanced white reflectance, high black and white contrast, and color display with a simple member constitution.

[Production of Display Element 4b]

(Preparation of Inks)

Inks 1b-3b were prepared by dissolving 0.3 g of each of following compounds 2, (A), and (B) in 2.5 g of ethanol.

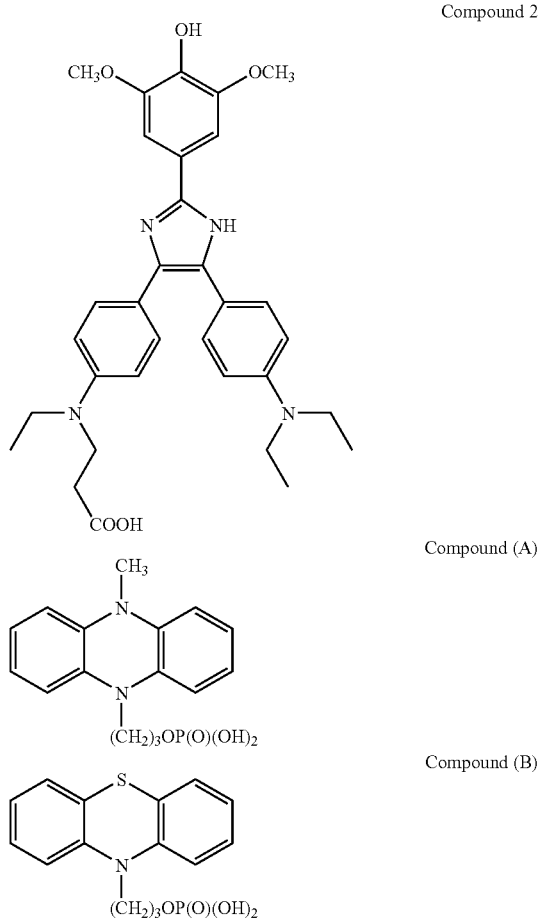

Compound 2

Compound (A)

Compound (B)

(Preparation of an Electrolytic Solution)

Electrolytic solution 6b was prepared by dissolving 0.1 g of silver iodide, 0.15 g of sodium iodide, and 0.05 g of polyethylene glycol (average molecular weight: 500) in 2.5 g of dimethyl sulfoxide.

(Production of a Display Element)

An ITO film of a pitch of 145 μm and an electrode width of 130 μm was formed on a glass substrate of 2 cm×4 cm having a thickness of 1.5 mm via a conventionally known method. Titanium oxide (average particle diameter: 25 nm) was coated thereon at a ratio of 10 g/m$^2$, followed by firing at 350° C. for 1 hour. Electrode 5b with the thus-formed metal oxide porous film was obtained.

Subsequently, using a commercially available ink-jet coating apparatus, inks 1-3 were separately coated on electrode 5 via Bayer arrangement to produce electrode 6b. Electrode 6b and electrode 1 were bonded together at right angles to each stripe electrode, followed by being heat-pressed to produce a vacant cell. Electrolytic solution 6b was vacuum-injected into the vacant cell, and then the injection inlet was sealed with an epoxy-based UV curable resin to produce display element 4b.

(Evaluation of Display Element 4b)

Display element 4b was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 68% and 3%, respectively. The display element of the present invention was confirmed to be able to realize enhanced white reflectance, high black and white contrast, and color display with a simple member constitution.

Example 9

Production of Display Element 1

(Preparation of Electrolytic Solution 1c)

There were dissolved 0.1 g of silver iodide, 0.15 g of sodium iodide, 0.05 g of polyethylene glycol (average molecular weight: 500,000), and 0.1 g of exemplified compound 3-1 in 2.5 g of dimethyl sulfoxide to obtain electrolytic solution 1c.

(Production of Electrode 1c)

An ITO (indium tin oxide) film of a pitch of 145 μm and an electrode width of 130 μm was formed on a glass substrate of 2 cm×4 cm having a thickness of 1.5 mm via a conventionally known method to obtain electrode 1c which was a transparent one.

(Production of Electrode 2c)

Titanium oxide (average particle diameter: 25 nm) was coated on electrode 1c at a ratio of 10 g/m$^2$, followed by firing at 350° C. for 1 hour. Electrode 2c with the thus-formed metal oxide porous film was obtained.

(Production of Electrode 3c)

A silver-palladium electrode having an electrode thickness of 0.8 μm, a pitch of 145 μn, and an electrode width of 130 μm was formed on a glass substrate of 2 cm×4 cm having a thickness of 1.5 mm via a conventionally known method. This electrode was designated as electrode 3c.

(Production of Electrode 4c)

There was coated, for a length of 100 μm, a mixed liquid prepared by dispersing 20% by mass of titanium oxide in an isopropanol solution containing polyvinyl alcohol (average polymerization degree: 3500; and saponification degree: 87%) at 2% by mass using an ultrasonic homogenizer on electrode 2c whose peripheral portion was edged with an olefin-based sealing agent containing glass spherical beads of an average particle diameter of 40 μm at 10% by volume, and then drying was carried out at 15° C. for 30 minutes to evaporate the solvent, followed by drying under an ambience of 45° C. for 1 hour to produce electrode 4c.

(Production of Display Element 1c)

Electrode 4 and electrode 1 were bonded together at right angles to each stripe electrode, followed by being heat-pressed to produce a vacant cell. Electrolytic solution 1c was vacuum-injected into the vacant cell, and then the injection inlet was sealed with an epoxy-based UV curable resin to produce display element 1c.

[Evaluation of Display Element 1c]

Both electrodes of display element 1c were connected to both terminals of a constant voltage power supply and a voltage of ±1.5 V was applied. The colored state of the display element was observed and reflectance was measured using the D65 light source of spectrophotometer CM-3700d (produced by Konica Minolta Sensing, Inc.). Display element 1c realized white display stemming from the reduction state of exemplified compound 3-1 and the oxidation state of silver during no voltage application; cyan display (maximum absorption wavelength: 662 nm) stemming from the oxidation state of exemplified compound 3-1 and the oxidation state of solver during +1.5 V application; and black display stemming from the reduction state of silver during −1.5 V application on the transparent electrode side. Accordingly, the results showed that multi-color display of 3 colors was realized using one type of electrolyte between a pair of opposite electrodes.

Examples 10 and 11

Production of Display Elements 2c and 3c

Electrolytic solutions 2c and 3c were prepared in the same manner as in preparation of electrolytic solution 1c described in Example 9 except that exemplified compound 3-1 was changed to an equimolar amount of exemplified compound 3-3 and exemplified compound 3-5, respectively. Further, display elements 2c and 3c were produced in the same manner as in production of display element 1c described in Example 9 except that electrode 1c was changed to electrode 2c, and electrolyte 1c was changed to electrolytic solutions 2c and 3c, respectively.

Evaluation of Display Elements 2c and 3c

Evaluation was conducted in the same manner as for display element 1c.

Display element 2c realized white display stemming from the reduction state of exemplified compound 3-3 and the oxidation state of silver during no voltage application; cyan display (maximum absorption wavelength: 654 nm) stemming from the oxidation state of exemplified compound 3-3 and the oxidation state of solver during +1.5 V application; and black display stemming from the reduction state of silver during −1.5 V application on the transparent electrode side.

Display element 3c realized white display stemming from the reduction state of exemplified compound 3-5 and the oxidation state of silver during no voltage application; cyan display (maximum absorption wavelength: 649 nm) stemming from the oxidation state of exemplified compound 3-5 and the oxidation state of silver during +1.5 V application; and black display stemming from the reduction state of silver during −1.5 V application on the transparent electrode side. Accordingly, also in display elements 2c and 3c, the results showed that multi-color display of 3 colors was realized using one type of electrolyte between a pair of opposite electrodes.

Example 12

Production of Display Element 4c

Display element 4c was produced in the same manner as in production of display element 1c described in Example 9 except that electrolytic solution 1c was changed to electrolytic solution 2c.

Evaluation of Display Element 4c

Evaluation was conducted in the same manner as for display element 1c. Display element 4c realized white display stemming from the reduction state of exemplified compound 3-3 and the oxidation state of silver during no voltage application; cyan display (maximum absorption wavelength: 658 nm) stemming from the oxidation state of exemplified compound 3-3 and the oxidation state of silver during +1.5 V application; and black display stemming from the reduction state of silver during −1.5 V application on the transparent electrode side.

Example 13

Production of Display Element 5c

Electrolytic solution 4c was prepared in the same manner as for electrolytic solution 1c used in production of display element 1c described in Example 9 except that 0.3 g of titanium oxide was added.

The peripheral portion of electrode 3c described in Example 9 was edged with an olefin-based sealing agent containing glass spherical beads of an average particle diameter of 20 μm at 10% by volume. And then a partition wall having 100 μm square windows was formed on the pixel portions intersecting with electrode 1c via photolithography to produce electrode 5c. Electrolytic solutions 1c, 2c, and 4c were injected into the individual windows separately via Bayer arrangement using a dispenser. Further, electrode 1c was bonded at right angles to each stripe electrode to produce display element 5c.

Evaluation of Display Element 5c

Display element 5c was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 65% and 3%, respectively. The display element of the present invention was confirmed to be able to realize enhanced white reflectance, high black and white contrast, and color display with a simple member constitution.

Example 14

Production of Display Element 6c

Inks 1c-3c were prepared by dissolving 0.3 g of each of exemplified compound 3-5, exemplified compound 3-7, and exemplified compound 3-8 in 2.5 g of ethanol.

Electrolytic solution 5c was prepared by dissolving 0.1 g of silver iodide, 0.15 g of sodium iodide, and 0.05 g of polyethylene glycol (average molecular weight: 500) in 2.5 g of dimethyl sulfoxide.

Using a commercially available ink-jet coating apparatus, inks 1c-3c were separately coated on electrode 4c via Bayer arrangement to produce electrode 6c. Electrode 6c and electrode 1c were bonded together at right angles to each stripe electrode, followed by being heat-pressed to produce a vacant cell. Electrolytic solution 5c was vacuum-injected into the vacant cell, and then the injection inlet was sealed with an epoxy-based UV curable resin to produce display element 6c.

Evaluation of Display Element 6c

Display element 6c was subjected to simple matrix driving by varying the applied voltage of each pixel. Observation of the tone of the display element showed that each color of white, black, yellow, magenta, cyan, blue, green, and red was able to be displayed. Further, the reflectance during white display and the reflectance during black display of the display element at 550 nm were 66% and 3%, respectively. The display element of the present invention was confirmed to be able to realize enhanced white reflectance, high black and white contrast, and color display with a simple member constitution.

What is claimed is:

1. A display element comprising:
an electrochromic compound which is colored or decolored due to oxidation or reduction,
a metallic salt compound,
an electrolyte, and
white scattering material incorporated between opposed electrodes, wherein
the metallic salt compound causes a color variation by dissolution-deposition of a metal element; and
multi-color display of substantially 3 or more colors comprising black display, white display and colored display other than black are carried out by a driving operation of the opposite electrodes, wherein a coloring overvoltage (VECW) and the decoloring overvoltage (VECE) of an electrochromic dye, and the deposition overvoltage (VAgW) and the dissolution overvoltage (VAgE) of silver of a silver salt compound satisfy all the conditions defined by following Relational expression (X):

VECW absolute value>VECE absolute value

VECW absolute value>VAgE absolute value

VAgW absolute value>VECE absolute value

VAgW absolute value>VAgE absolute value.   Relational expression (X).

2. The display element of claim 1, wherein the metallic salt compound comprises a compound containing silver salt.

3. The display element of claim 1, wherein the electrochromic compound is colored due to oxidation and is decolored to be transparent due to reduction.

4. The display element of claim 1, wherein the electrochromic compound is colored due to reduction and is decolored to be transparent due to oxidation.

5. The display element of claim 1, wherein the electrochromic compound comprises a compound represented by Formula (A):

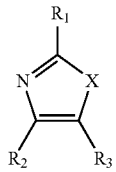

Formula (A)

wherein $R_1$ represents a substituted or unsubstituted aryl group, $R_2$ and $R_3$ each represents a hydrogen atom or a substituent, X represents >N—$R_4$, an oxygen atom or a sulfur atom, and $R_4$ represents a hydrogen atom or a substituent.

6. The display element of claim 1, wherein the electrochromic compound comprises a compound represented by Formula (1) or Formula (2):

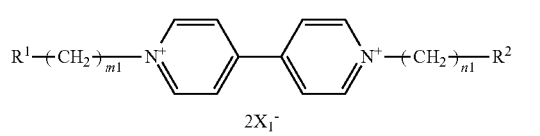

Formula (1)

wherein $R^1$ and $R^2$ each represents a hydrogen atom, an aryl group or a heteroaryl group each having 14 or less carbon atoms; a branched alkylene group or an alkenylene group each having 10 or less carbon atoms; or a cycloalkylene group; n1 and m1 each represents an integer of 0 to 10; and $X_1^-$ represents an ion which neutralizes the charge,

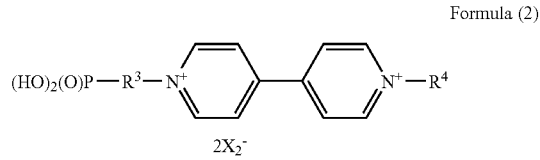

Formula (2)

wherein $R^3$ represents: —$(CH_2)_m$— wherein m represents an integer of 0 to 10; an arylene group or a heteroarylene group each having 14 or less carbon atoms, a branched alkylene group or an alkenylene group each having 10 or less carbon atoms or a cycloalkylene group; each of the arylene group, heteroarylene group, branched alkylene group, branched alkenylene group or cycloalkylene group may have a —P(O)(OH)$_2$ group through a —(CH$_2$)$_n$— group or may be arbitrarily substituted, wherein n represents an integer of 0 to 10; $R^4$ represents a group represented by —(CH$_2$)$_p$—$R^5$ wherein p represents an integer of 0 to 10 and $R^5$ represents —P(O)(OH)$_2$ group or an aryl group or a heteroaryl group each having 14 or less carbon atoms, and an alkyl group or an alkenyl group each having 10 or less carbon atoms or a cycloalkyl group or a hydrogen atom; and $X_2^-$ represents an ion which neutralizes the charge.

7. The display element of claim 1, wherein the electrochromic compound comprises a compound represented by Formula (I) to Formula (VI):

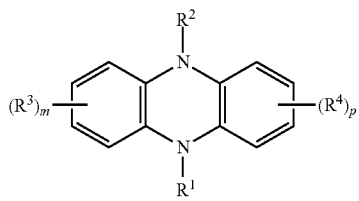
Formula (I)

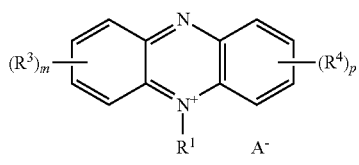
Formula (II)

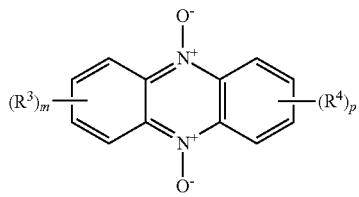
Formula (III)

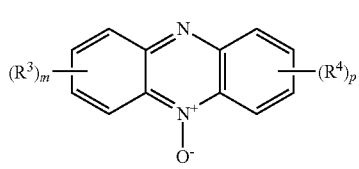
Formula (IV)

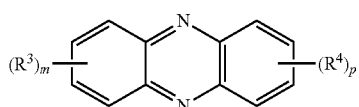
Formula (V)

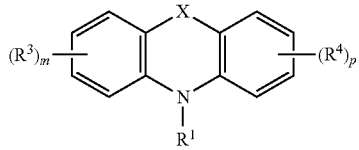
Formula (VI)

wherein $R^1$ and $R^2$ each represents a hydrogen atom or a substituent; $R^3$ and $R^4$ each represents a hydrogen atom or a substituent; m and p each represents an integer of 0 to 4; X represents an oxygen atom or a sulfur atom; and $A^-$ represents a counter ion to balance charge.

8. The display element of claim 1, wherein the electrochromic compound comprises a compound represented by Formula [1] to Formula [8]:

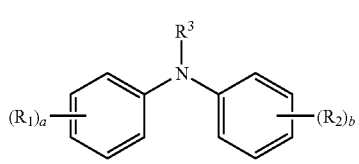
Formula [1]

wherein $R_1$ and $R_2$ each represents a substituent; $R_3$ represents a hydrogen atom or a substituent and when $R_3$ represents a hydrogen atom either $R_1$ or $R_2$ represents amino group; a and b each represents an integer of 0 to 5; when a and b each is 2 or more, 2 or more $R_1$'s or 2 or more $R_2$'s each may be the same or different; and adjacent $R_1$'s or $R_2$'s each may join to form a ring,

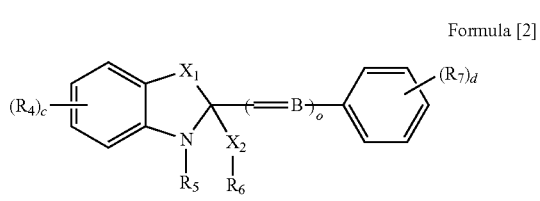
Formula [2]

wherein $R_4$ and $R_7$ each represents a substituent; $R_5$ and $R_6$ each represents a alkyl group; $R_5$ and $R_6$ may join to form a ring or an ortho position of the phenyl group joining B and X2 may directly join to form a ring; $X_1$ represents —$CR_{30}R_{31}$—, —$NR_{32}$, —O— or —S—; $X_2$ represents —O— or —S—; B represents =CH— or =N—; c represents an integer of 0 to 4 and when c is 2 or more, 2 or more $R_4$'s each may be the same or different or adjacent $R_4$'s may join to form a ring; d is an integer of 0 to 5, and when d is 2 or more, 2 or more $R_7$'s each may be the same or different or adjacent $R_7$'s may join to form a ring; and o represents 1 or 2,

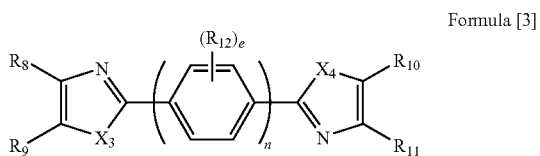
Formula [3]

wherein $R_8$ to $R_{11}$ each represents a hydrogen atom or a substituent; $R_{12}$ represents a substituent; $X_3$ and $X_4$ each represents —$CR_{30}, R_{31}$—, —$NR_{32}$, —O— or —S—; e represents an integer of 0 to 4 and when e is 2 or more, 2 or more $R_{12}$'s each may be the same or different or adjacent $R_{12}$'s may join to form a ring; and n represents 0 or 1,

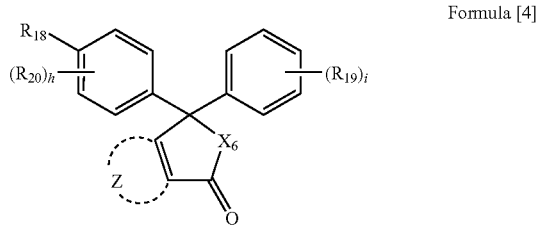
Formula [4]

wherein $R_{18}$ represents a hydroxyl group, an alkoxy group or an amino group; $R_{19}$ and $R_{20}$ each represents a substituent; h is an integer of 0 to 4 and when h is 2 or more, 2 or more $R_{20}$'s each may be the same or different or adjacent $R_{20}$'s may join to form a ring; i is an integer of 0 to 5 and when i is 2 or more, 2 or more $R_{19}$'s each may be the same or different and adjacent $R_{19}$'s may join to form a ring, further adjacent $R_{19}$ and $R_{20}$ may join to form a ring; $X_6$ represents —O— or —$NR_{32}$; and Z represents a residual group needed to form an aromatic or heterocyclic ring,

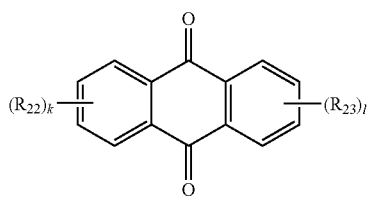

Formula [5]

wherein $R_{22}$ and $R_{23}$ each represent a substituent; k and l each independently represent an integer of 0 to 4; when k and l represent 2 or more, 2 or more $R_{22}$'s or 2 or more $R_{23}$'s may be the same or different, and further adjacent $R_{22}$'s or $R_{23}$'s may join to form a ring,

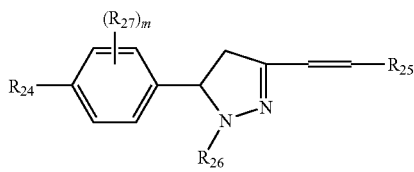

Formula [6]

wherein $R_{24}$ represents a hydroxyl group, an alkoxy group, or an amino group; $R_{25}$ represents an aryl group or a heterocyclic group; $R_{26}$ represents a hydrogen atom, an alkyl group, an aryl group, a heterocyclic group, an acyl group, or a carbamoyl group; $R_{27}$ represents a substituent; m represents an integer of 0 to 4, when m represents 2 or more, 2 or more $R_{27}$'s each may be the same or different, and further adjacent $R_{27}$'s may join to form a ring,

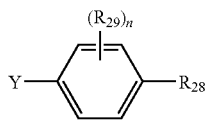

Formula [7]

wherein $R_{28}$ and $R_{29}$ each represent a substituent; n represents an integer of 0 to 4, when n represents 2 or more, 2 or more $R_{29}$'s each may be the same or different, and further adjacent $R_{29}$'s may join to form a ring; and Y represents an electron attractive group,

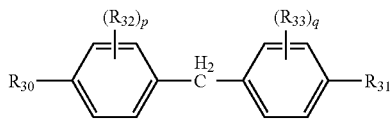

Formula [8]

wherein $R_{30}$ and $R_{31}$ represent a hydrogen atom, a hydroxyl group, an alkoxy group, or an amino group; $R_{30}$ and $R_{31}$ do not represent a hydrogen atom simultaneously; $R_{32}$ and $R_{33}$ each represent a substituent; p and q each independently represent an integer of 0 to 4, when p and q are 2 or more, 2 or more $R_{32}$'s or 2 or more $R_{33}$'s each may be the same or different, adjacent $R_{32}$'s or $R_{33}$'s each may join to form a ring.

9. The display element of claim 1, wherein the electrochromic compound is chemically or physically adsorbed on a surface of at least one of the opposite electrodes.

10. The display element of claim 1, wherein the electrochromic compound comprises at least one of a absorption group containing —$CO_2H$, —$PO(OH)_2$, —$OPO(OH)_2$, —$SO_3H$ or —$Si(OR)_3$, wherein R represents a hydrogen atom or an alkyl group.

11. The display element of claim 1, wherein at least one of the opposite electrodes comprises a metal oxide porous layer and the electrochromic compound is supported on the metal oxide porous layer.

12. The display element of claim 1, wherein the white scattering material comprises $TiO_2$, $ZnO$ or $Al_2O_3$.

13. The display element of claim 1, wherein substantially black state is displayed by a cathode reaction.

14. The display element of claim 1, wherein a colored display other than black is conducted by a level arrangement of display areas which creates hues practically differing from one another.

15. The display element of claim 14, wherein different electrochromic compounds are supported on the metal oxide porous layer.

16. The display element of claim 15, wherein different electrochromic compounds are separately coated on the metal oxide porous layer by an ink jet method.

17. A method of driving the display element of claim 1, wherein a voltage (VW) between the opposite electrodes during a white display driving operation satisfies all the conditions defined by following Relational expression (Y):

VECW absolute value>VW>VECE absolute value

VECW absolute value>VW>VAgE absolute value

VAgW absolute value>VW>VECE absolute value

VAgW absolute value>VW>VAgE absolute value,   Relational expression (Y)

wherein VECW, VECE, VAgE, and VAgW represents a coloring overvoltage and a decoloring overvoltage of an electrochromic dye, and a deposition overvoltage and a dissolution overvoltage of silver of a silver salt respectively.

* * * * *